US009714414B2

(12) United States Patent
Jaenisch et al.

(10) Patent No.: US 9,714,414 B2
(45) Date of Patent: *Jul. 25, 2017

(54) REPROGRAMMING OF SOMATIC CELLS

(71) Applicant: Whitehead Institute for Biomedical Research, Cambridge, MA (US)

(72) Inventors: Rudolf Jaenisch, Brookline, MA (US); Yaqub Hanna, Boston, MA (US); Marius Wernig, Woodside, CA (US); Christopher J. Lengner, Wellesley, MA (US); Alexander Meissner, Cambridge, MA (US); Oliver Tobias Brambrink, Cambridge, MA (US); G. Grant Welstead, Cambridge, MA (US); Ruth Foreman, Somerville, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/473,250

(22) Filed: Aug. 29, 2014

(65) Prior Publication Data

US 2015/0118755 A1    Apr. 30, 2015

Related U.S. Application Data

(63) Continuation of application No. 12/595,041, filed as application No. PCT/US2008/004516 on Apr. 7, 2008.

(60) Provisional application No. 60/922,121, filed on Apr. 7, 2007, provisional application No. 60/959,341, filed on Jul. 12, 2007, provisional application No. 61/036,065, filed on Mar. 12, 2008.

(51) Int. Cl.
    C12N 5/074      (2010.01)
    C07K 14/47      (2006.01)
    A01K 67/027     (2006.01)
    C12N 15/85      (2006.01)
    C12N 15/877     (2010.01)
    G01N 33/50      (2006.01)

(52) U.S. Cl.
    CPC ........ *C12N 5/0696* (2013.01); *C07K 14/4702* (2013.01); *A01K 67/0273* (2013.01); *A01K 67/0275* (2013.01); *A01K 2217/05* (2013.01); *A01K 2227/105* (2013.01); *C12N 15/8509* (2013.01); *C12N 15/8775* (2013.01); *C12N 2501/602* (2013.01); *C12N 2501/603* (2013.01); *C12N 2501/604* (2013.01); *C12N 2501/605* (2013.01); *C12N 2501/606* (2013.01); *C12N 2506/11* (2013.01); *C12N 2506/13* (2013.01); *C12N 2800/30* (2013.01); *C12N 2830/003* (2013.01); *C12N 2830/006* (2013.01); *G01N 33/5023* (2013.01); *G01N 2333/91011* (2013.01)

(58) Field of Classification Search
    CPC .................. C12N 5/0696; C07K 14/4702
    See application file for complete search history.

(56) References Cited

U.S. PATENT DOCUMENTS

| | | | |
|---|---|---|---|
| 5,824,837 | A  | 10/1998 | Chen et al. |
| 5,843,780 | A  | 12/1998 | Thomson |
| 6,200,806 | B1 | 3/2001  | Thomson |
| 7,015,037 | B1 | 3/2006  | Furcht et al. |
| 7,524,677 | B2 | 4/2009  | Stockman et al. |
| 7,601,699 | B2 | 10/2009 | Eilertsen |
| 7,682,828 | B2 | 3/2010  | Jaenisch et al. |
| 7,687,266 | B2 | 3/2010  | Chambers et al. |
| 8,071,369 | B2 | 12/2011 | Jaenisch et al. |
| 2002/0168660 | A1 | 11/2002 | Chen et al. |
| 2004/0137460 | A1 | 7/2004  | Yamanaka et al. |
| 2005/0287547 | A1 | 12/2005 | Seligman |
| 2006/0084172 | A1 | 4/2006  | Muller et al. |
| 2007/0032447 | A1 | 2/2007  | Eilersten |
| 2008/0066197 | A1 | 3/2008  | Ying et al. |
| 2008/0280362 | A1 | 11/2008 | Jaenisch et al. |
| 2009/0047263 | A1 | 2/2009  | Yamanaka et al. |
| 2009/0068742 | A1 | 3/2009  | Yamanaka |
| 2009/0227032 | A1 | 9/2009  | Yamanaka et al. |
| 2010/0062533 | A1 | 3/2010  | Yamanaka |
| 2010/0144031 | A1 | 6/2010  | Jaenisch et al. |
| 2010/0221827 | A1 | 9/2010  | Jaenisch et al. |
| 2010/0310525 | A1 | 12/2010 | Chevalier et al. |
| 2011/0076678 | A1 | 3/2011  | Jaenisch et al. |

(Continued)

FOREIGN PATENT DOCUMENTS

| | | | |
|---|---|---|---|
| AU | 2006325975 A1 | 6/2007 |
| CN | 101855350     | 10/2010 |

(Continued)

OTHER PUBLICATIONS

Fawell et al. PNAS 91:664-668, 1994.*

(Continued)

*Primary Examiner* — Marcia S Noble

(74) *Attorney, Agent, or Firm* — Lisa M. Warren, Esq.; Morse, Barnes-Brown & Pendleton, P.C.

(57) ABSTRACT

The disclosure relates to a method of reprogramming one or more somatic cells, e.g., partially differentiated or fully/terminally differentiated somatic cells, to a less differentiated state, e.g., a pluripotent or multipotent state. In further embodiments the invention also relates to reprogrammed somatic cells produced by methods of the invention, to uses of said cells, and to methods for identifying agents useful for reprogramming somatic cells.

9 Claims, 4 Drawing Sheets

(56) References Cited

U.S. PATENT DOCUMENTS

| | | | |
|---|---|---|---|
| 2011/0151447 A1* | 6/2011 | Park | C07K 14/4702 435/6.1 |
| 2012/0028821 A1 | 2/2012 | Jaenisch et al. | |
| 2012/0034192 A1 | 2/2012 | Young et al. | |
| 2012/0282229 A1 | 11/2012 | Kannemeier et al. | |
| 2013/0017596 A1 | 1/2013 | Townes et al. | |
| 2013/0065311 A1 | 3/2013 | Yamanaka et al. | |

FOREIGN PATENT DOCUMENTS

| | | |
|---|---|---|
| EP | 1 970 446 | 9/2008 |
| WO | WO 99/55841 | 11/1999 |
| WO | WO 00/27995 | 5/2000 |
| WO | WO 02/097090 | 12/2002 |
| WO | WO 2005/080598 | 9/2005 |
| WO | WO 2005/090557 | 9/2005 |
| WO | WO 2007/069666 A1 | 6/2007 |
| WO | WO 2008/001391 A2 | 1/2008 |
| WO | WO 2008/118820 | 10/2008 |
| WO | WO 2008/118820 A2 | 10/2008 |
| WO | WO 2008/124133 A1 | 10/2008 |
| WO | WO 2009/117439 A2 | 9/2009 |
| WO | WO 2009/133971 | 11/2009 |
| WO | WO 2009/152529 A2 | 12/2009 |
| WO | WO 2010/033920 A2 | 3/2010 |

OTHER PUBLICATIONS

Cavaleri, et al., "Nanog: A New Recruit to the Embryonic Stem Cell Orchestra", Cell 113: 551-557 (2003).
Stevanovic, et al., The cDNA sequence and chromosomal location of the human SOX2 gene:, Mammalian Genome 5: 640-642 (1994).
Non-Final Office Action for U.S. Appl. No. 12/997,815, dated May 19, 2015.
Notice of Allowance for U.S. Appl. No. 13/646,430, dated Jun. 18, 2015.
Notice of Allowance for U.S. Appl. No. 12/595,041, mailed Mar. 7, 2016.
Grinnell, et al., "De-Differentiation of Mouse Interfollicular Keratinocytes by the Embryonic Transcription Factor Oct-4", Journal of Investigative Dermatology, 127; 372-380 (2007).
Kim et al., "Oct4-Induced Pluripotency in Adult Neural Stem Cells," Cell, 136:411-419 (2009).
Patel et al., "Advances in Reprogramming Somatic Cells to Induced Pluripotent Stem Cells," NIH Public Access Author Manuscript, Jan. 1, 2011 (online) [retrieved from internet May 3, 2015] URL:http://ncbi.nih.gov/pmc/articles/PMC2924949/pdf/nihms-219126.pdf published in final edited form as: Stem Cell Reviews 6(3):367-380 (Sep. 2010).
Final Office Action for U.S. Appl. No. 12/997,815, dated Feb. 19, 2016.
Final Office Action for U.S. Appl. No. 12/595,041, dated Oct. 30, 2015.
Final Office Action for U.S. Appl. No. 14/923,321, mailed Jan. 4, 2017.
Notice of Allowance for U.S. Appl. No. 12/997,815, mailed Jun. 30, 2016.
Non-final Office Action for U.S. Appl. No. 14/923,321, mailed Aug. 2, 2016.
Aoi, et al., "Generation of Pluripotent Stem Cells from Adult Mouse Liver and Stomach Cells", Science, 321: 699-702 (2008).
Avilion, et al., "Multipotent cell lineages in early mouse development depend on SOX2 function", Genes & Development, 17:126-140 (2003).
Ben-Shushan, et al., "Extinction of Oct-3/4 gene expression in embryonal carcinoma x fibroblast somatic cell hybrids is accompanied by changes in the methylation status, chromatin structure, and transcriptional activity of the Oct-3/4 upstream region", Molecular and Cellular Biology, 13(2):891-901 (1993).
Bortvin, et al., "Incomplete Reactivation of Oct4-related in Mouse Embryos Cloned from Somatic Nuclei", Development, 130:1673-1680 (2003).
Boyer, et al,, "Polycomb complexes repress developmental regulators in murine embryonic stem cells", Nature, 441(7091):349-353 (2006).
Brambrink, et al., "Sequential Expression of Pluripotency Markers During Direct Reprogramming of Mouse Somatic Cells", Cell Stem Cell, 2(2): 151-159 (2008).
Bronson, et al., "Single-copy transgenic mice with chosen-site integration", Proc. Natl. Acad. Sci. USA, 93:9067-9072 (1996).
Bru, et al., "Rapid induction of pluripotency genes after exposure of human somatic cells to mouse ES cell extracts", Experimental Cell Research, 314:2634-2642 (2008).
Buske, et al., "Overexpression of HOXA10 perturbs human lymphomyelopoiesis in vitro and in vivo", Blood, 97(8):2286-2292 (2001).
Carey, et al., "Reprogramming of murine and human somatic cells using a single polycistronic vector", Proceedings of the National Academy of Science, 106:157-162 (2008).
Chambers, et al., "Functional expression cloning of nanog, a pluripotency sustaining factor in embryonic stem cells", Cell, 113:643-655 (2003).
Chen, et al., "Establishment and Maintenance of Genomic Methylation Patterns in Mouse Embryonic Stem Cells by Dnmt3a and Dnmt3b", Molecular and Cellular Biology, 23(16):5594-5605 (2003).
Daniels, et al., "Analysis of Gene Transcription in Bovine Nuclear Transfer Embryos Reconstructed with Granulosa Cell Nuclei", Biology of Reproduction, 63:1034-1040 (2000).
Eminli, et at., "Reprogramming of Neural Progenitor Cells into iPS Cells in the Absence of Exogenous Sox2 Expression", Stem Cells, 26:2467-2474 (2008).
Gossen, et al., "Transcriptional activation by tetracyclines in mammalian cells", Science, 268(5218):1766-1769 (1995).
Greiner, et al., "Identification of a specific inhibitor of the histone methyltransferase SU(VAR)3-9", Nature Chemical Biology, 1:143-145 (2005).
Hanna, et al. "Direct reprogramming of terminally differentiated mature B lymphocytes to pluripotency", Cell 133, 250-264 (2008).
Hansis, et al., "Analysis of Oct-4 expression and ploidy in individual human blastomeres", Molecular Human Reproduction, 7: 155-161 (2001).
Hasegawa, et al., "Efficient multicistronic expression of a transgene in human embryonic stem cells," Stem Cells, 25(7): 1707-1712 (2007).
Helgason, et al., "Overexpression of HOXB4 enhances the hematopoietic potential of embryonic stem cells differentiated in vitro", Blood, 87(7):2740-2749 (1996).
Ho, et al. "Synthetic Protein Transduction Domains: Enhanced Transduction Potential in Vitro and in Vivo," Cancer Research, 61: 474-477 (2001).
Hochedlinger, et al., "Monoclonal mice generated by nuclear transfer from mature B and T donor cells", Nature, 415:1035-1038 (2002).
Hochedlinger, et al., "Nuclear transplantation, embryonic stem cells, and the potential for cell therapy", The New England Journal of Medicine, 349(3):275-286 (2003).
Ihle, et al., "STATs: Signal Transducers and Activators of Transcription", Cell, 84: 331-334 (1996).
Jackson-Grusby, et al., "Loss of Genomic Methylation Cases p53-Dependent Apoptosis and Epigenetic Deregulation", Nature Genetics, 27: 31-39 (2001).
Jaenisch, Rudolf, Abstract "In vitro reprogramming of somatic cells into pluripotent ES-like cells", National Institutes of Health Grant No. 5 R37 HD045022-06, Funding Date 2008.
Jaenisch, Rudolf, Abstract "Nuclear Closing and the Reprogramming of the Genome" National Institutes of Health Grant No. 5 R37 HD045022-01 through 5 R37 HD045022-05, Funding Dates 2003 through 2007.
Jaenisch, Rudolf, Abstract "Genomic Imprinting and the Cloning of Mice" National Institutes of Health Grant No. 5 R01 CA084198-01 through 5R01 CA084198-09, Funding Dates 2000 through 2008.

(56) References Cited

OTHER PUBLICATIONS

Jaenisch, Rudolf, Abstract *"Epigenetics, stem cells, and cancer"* National Institutes of Health Grant Nos. 5 RO1 CA087869-06 through 5 RO1 CA087869-08, Funding Dates 2006 through 2008.
Jaenisch, Rudolf, Abstract *"DNA Methylation, Gene Regulation, and Cancer"* National Institutes of Health Grant Nos. 5 RO1 CA087869-01 through 5 RO1 CA087869-05, Funding Dates 2001 through 2005.
Jaenisch, et al., "Nuclear cloning, stem cells, and genomic reprogramming", *Cloning and Stem Cells*, 4(4):389-396 (2002).
Jaenisch & Young, "Stem Cells, the Molecular Circuitry of Pluripotency and Nuclear Reprogramming", *Cell*, 132, 567-582 (2008).
Kaufman, et al., "Hematopoietic colony-forming cells derived from human embryonic stem cells", *PNAS*, 98(19):10716-10721 (2001).
Kubicek, et al., "Reversal of H3K9me2 by a small-molecule inhibitor for the G9a histone methyltransferase", *Molecular Cel*, 25(3)1473-81 (2007).
Kyba et al., "HoxB4 confers definitive lymphoid-myeloid engraftment potential on embryonic stem cell and yolk sac hematopoietic progenitors", *Cell*, 109:29-37 (2002).
Lenardo et al., "Repression of the IgH Enhancer in Teratocarcinoma Cells Associated with a Novel Octamer Factor", *Science, New Series*, 243(4890):544-546 (1989).
Li, et al., "Murine embryonic stem cell differentiation is prompted by SOCS-3 and inhibited by the zinc finger transcription factor Klf4", *Blood*, 105:635-637 (2005).
Loh, et al., "The Oct4 and Nanog transcription network regulates pluripotency in mouse embryonic stem cells", *Nature Genetics*, 38(4): 431-440 (2006).
Lowry, et al. Generation of human induced pluripotent stem cells from dermal fibroblasts. *"PNAS"*, 105(8):2883-2888 (2008).
Ma, et al., "G9a and Jhdma2a Regulate Embryonic Stem Cell Fusion-Induced Reprogramming of Adult Neural Stem Cells", *Stem Cells*, 26)8): 2131-2141 (2008).
Matsuoka, et al., "Generation of definitive hematopoietic stem cells from murine early yolk sac and paraaortic splanchnopleures by aorta-gonad-mesonephros region-derived stromal cells", *Blood*, 98(1):6-12 (2001).
McWhir, et al., "Selective ablation of differentiated cells permits isolation of embryonic stem cell lines from murine embryos with a non-permissive genetic background", *Nature Genetics*, 14:223-226 (1996).
Mitsui et al., "The Homeoprotein Nanog is Required for Maintenance of Pluripotency in Mouse Epiblast and ES Cells", *Cell*, 113: 631-642 (2003).
Mountford, et al., "Dicistronic targeting constructs: Reporters and modifiers of mammalian gene expression", *Proceedings of the National Academy of Sciences*, 91: 4303-4307 (1994).
Munsie, et al., "Transgenic strategy for demonstrating nuclear reprogramming in the mouse", *Cloning Stem Cells*, 4(2):121-130 (2002).
Naito, et al., Journal of Reproduction and Fertility 113:137-143 (1998).
Nichols, et al., "Formation of Pluripotent Stem Cells in the Mammalian Embryo Depends on the POU Transcription Factor Oct4", *Cell*, 95: 379-391 (1998).
Niwa, et al., "Quantitative expression of Oct-3/4 defines differentiation, dedifferentiation or self-renewal of ES cells", *Nature Genetics*, 24: 372-376 (2000).
Okita, et al., "Generation of Mouse Induced Pluripotent Stem Cells Without Viral Vectors", *Science*, 322:949-953 (2008).
Peled, et al., "Dependence of human stem cell engraftment and repopulation of NOD/SCID mice on CXCR4", *Science*, 283:845-848 (1999).
Pesce, et al., "Oct-4: Gatekeeper in the beginnings of mammalian development", *Stem Cells*, 19:271-278 (2001).
Qi, et al., "The magic of four: induction of pluripotent stem cells from somatic cells by Oct4, Sox2, Myc and Klf4", *Cell Research*, 17:578-580 (2007).

Radcliffe, et al., "Multiple gene products from a single vector: 'self-cleaving' 2A peptides", *Gene Therapy*, 11:1673-1674 (2004).
Ramalho-Santos, et al., "Stemness: Transcriptional Profiling of Embryonic and Adult Stem Cells", *Science*, 298: 597-600 (2002).
Ryan, et al., "Cleavage of foot-and-mouth disease virus polyprotein is mediated by residues located within a 19 amino acid sequence", *Journal of General Virology*, 72:2727-2732 (1991).
Savarese, et al., "Hematopoietic Precursor Cells Transiently Reestablish Permissiveness for X Inactivation", *Molecular and Cellular Biology*, 26(19): 7167-7177 (2006).
Sells, et al., "Delivery of Protein into Cells Using Polycationic Liposomes," *BioTechniques* 19(1):72-78 (1995).
Shields, et al., "Identification and Characterization of a Gene Encoding a Gut-Enriched Kruppel-like Factor Expressed during Growth Arrest", *Journal of Biological Chemistry*, 271(33):20009-20017 (1996).
Stacey, et al., "Microinjection of Transforming ras Protein Induces c-fos Expression," *Molecular and Cellular Biology*, 7(1): 523-527 (1987).
Stadfeld, et al., "Reprogramming of Pancreatic β Cells into Induced Pluripotent Stem Cells", *Current Biology*, 18:890-894 (2008).
Stem Cells: Scientific Progress and Future Research Directions. Department of Health and Human Services, Jun. 2001, </info/scireport/2001report>. Chapter 4: The Adult Stem Cell, pp. 23-42.
Tada, et al., "Nuclear Reprogramming of Somatic Cells by In Vitro Hybridization with ES cells", *Current Biology*, 11: 1553-1558 (2001).
Takahashi, et al., "Induction of Pluripotent Stem Cells from Adult Human Fibroblasts by Defined Factors", *Cell*, 131, 861-872 (2007).
Takahashi, et al., "Induction of Pluripotent Stem Cells from Mouse Embryonic and Adult Fibroblast Cultures by Defined Factors", *Cell*, 126: 663-676 (2006).
Thomson, et al., "Embryonic Stem Cell Lines Derived from Human Blastocysts", *Science*, 282, 1145-1147 (1998).
Wadia, et al., "Protein Transduction Technology," *Analytical Biotechnology*, 13: 52-56 (2002).
Wernig, et al., "A drug-inducible transgenic system for direct reprogramming of multiple somatic cell types", *997 Biotechnology*, 26(8):916-924 (2008).
Wernig, et al., "In vitro reprogramming of fibroblasts into a pluripotent ES-cell-like state", *Nature*, 448: 318-324 (2007).
Wernig, et al., "Neurons derived from reprogrammed fibroblasts functionally integrate into the fetal brain and improve symptoms of rats with Parkinson's disease", *PNAS*, 105(15):5856-5861 (2008).
Yamanaka, et al., "Strategies and New Developments in the Generation of Patient-Specific Pluripotent Stem Cells", *Cell Stem Cell*, 1: 39-49 (2007).
Yeom et al., "Germline regulatory element of Oct-4 specific for the totipotent cycle of embryonal cells," *Development*,122:881-897 (1996).
Ying, et al., "BMP induction of Id proteins suppresses differentiation and sustains embryonic stem cell self-renewal in collaboration with STAT3", *Cell*, 115: 281-292 (2003).
Yoshimizu, et al., "Germline-specific expression of the Oct-4/green fluorescent protein (GFP) transgene in mice", *Development, Growth & Differentiation*, 41:675-684 (1999).
Young, Richard, Abstract "Transcriptional Regulatory Networks in Living Cells" National Institutes of Health Grant No. 5 RO1 HG002668-04A1 through 5 RO1 HG002668-05, Funding Dates 2007 through 2008.
Young, Richard, Abstract "Transcriptional Regulatory Network in Living Cells" National Institutes of Health Grant No. 5 RO1 HG002668-01 through 5 RO1 HG002668-03S1, Funding Dates 2003 through 2006.
Yu, et al., "Induced pluripotent stem cell lines derived from human somatic cells", *Science*, 318(5858):1917-20 (2007).
Zakhartchenko, et al., "Adult cloning in cattle: potential of nuclei from a permanent cell line and from primary cultures", *Molecular Reproduction and Development*, 54:264-272 (1999).
Zambrowicz, et al., "Disruption of overlapping transcripts in the ROSA βgeo 26 gene trap strain leads to widespread expression of β-galactosidase in mouse embryos and hematopoietic cells", *Proc. Natl. Acad. Sci. USA*, 94:3789-3794 (1987).

(56) References Cited

OTHER PUBLICATIONS

Zhou, et al., "Generation of Induced Pluripotent Stem Cells Using Recombinatnt Proteins", *Cell Stem Cell*, 4:381-384 (2009).
BLAST Alignment SEQ ID 16 (ECAT4).
Sox2, Print out from Pubmed http://www.ncbi.nlm.nih.gov/nuccore/127140985?ordinalp...ntrez.Sequence.Sequence_ResultsPanel.Sequence_RVDocSum p. 1-6, printed Apr. 7, 2009.
Nanog. Printout from Pubmed http://www.ncbi.nlm.nih.gov/nuccore/153791181?ordinalp...netrez.Sequence.Sequence_ResultsPanel.Sequence_RVDocSum p. 1-6, printed Apr. 7, 2009.
Scholer, et al., "New type of POU domain in germ line-specific protein Oct-4", Letters to Nature, 344: 435-439 (1990).
Bilic, et al., "Concise Review: Induced Pluripotent Stem Cells Versus Embryonic Stem Cells: Close Enough or Yet Too Far Apart?", *Stem Cells*, 30:33-41(2012).
Chin, et al., "Induced Pluripotent Stem Cells and Embryonic Stem Cells are Distinguished by Gene Expression Signatures", *Cell Stem Cell*, 5:111-123(2009).
Chin, et al., "Molecular Analyses of Human Induced Pluripotent Stem Cells and Embryonic Stem Cells", *Cell Stem Cell*, 7(2):263-269(2010).
Munoz, et al., "The Quantitative Proteomes of Human-Induced Pluripotent Stem Cells and Embryonic Stem Cells", *Molecular Systems Biology*, 7(550): 1-13(2011).
Polouliakh, et al., "Reprogramming Resistant Genes: In-Depth Comparison of Gene-Expressions Among iPS, ES, and somatic cells", *Frontiers in Physiology*, 4(7):1-9(2013).
Meissner, et al., "Direct Reprogramming of genetically unmodified fibroblasts into pluripotent stem cells", *Nature Biotechnology*, 25(10): 1177-1181 (2007).
Strelchenko, et al. "Reprogramming of human somatic cells by embryonic stem cell cytoplast", *Reprod. Biomed Online*, 12(1): 107-111 (2006).
Cowan, et al., Nuclear Reprogramming of Somatic Cells After Fusion with Human Embryonic Stem Cells, *Science*, 309:1369-1373 (2005).
Laiosa, et al., "Reprogramming of Committed T Cell Progenitors to Macrophages and Dendritic Cells by C/EBPa and PU.1 Transcription Factors", *Immunity*, 25: 731-744 (2006).
Ait-Si-Ali, et at., "A Suv39h-dependent mechanism for silencing S-phase genes in differentiating but not in cycling cells", *EMBO Journal*, 23:605-615 (2004).
Maherali, et al., "Directly Reprogrammed Fibroblasts Show Global Epigenetic Remodeling and Widespread Tissue Contribution", Cell Stem Cell, 1:55-70(2007).
Sarraf, et al., "Methyl-CpG Binding Protein MBD1 Couples Histone H3 Methylation at Lysine 9 by SETDB1 to DNA Replication and Chromatin Assembly", Molecular Cell, 15:595-605 (2004).
PubMed Oct4 gene, Printout from www.ncbi.nlm.nih.gov/nuccore/NM_013633.3, pp. 1-12, Sep. 19, 2013.
Palmqvist, et al, "Correlation of Murine Embryonic Stem Cell Gene Expression Profiles with Functional Measures of Pluripotency", Stem Cells, 23:663-680 (2005).
Yu, et al., "Induced pluripotent stem cell lines derived from human somatic cells", Science, 318:1917-1920 (2007).
Sox2 cDNA, printout from http://ncbi.nih.gov/nuccor/BC057574.1, pp. 1-13 (2013).
Oct4 cDNA, printout from http://ncbi.nih.gov/nuccor/BC117437.1, pp. 1-10 (2013).
Chinnasamy, et al., "Multicistronic lentiviral vectors containing the FMDV 2A cleavage factor demonstrate robust expression of encoded genes at limiting MOI", *Virology Journal*, 3: 14-29 (2006).
Okita, et al., "Generation of germline-competent induced pluripotent stem cells", *Nature*, 448: 313-318 (2007).
Feldman, et al., "G9a-mediated irreversible epigenetic inactivation of Oct-3/4 during early embryogenesis", *Nature Cell Biology*, 455: 627-633 (2008).
Zhou, et al., "In vivo reprogramming of adult pancreatic exocrine cells to b-cells", *Nature*, 455: 627-633 (2008).

Kong, et al., "Lack of specificity of fibroblast-specific protein 1 in cardiac remodeling and fibrosis", *American Journal of Physiology Heart and Circulatory Physiology*, 305: H1363-1372 (2013).
Nakagawa, et al., "Generation of induced pluripotent stem cells without Myc from mouse and human fibroblasts", *Nature Biotechnology*, 26(1): 101-106 (2008).
Silva, et al., "Nanog promotes transfer of pluripotency after cell fusion", *Nature*, 441: 997-1001 (2006).
Shi, et al., Dynamic Regulation of Histone Lysine Methylation by Demethylases, *Molecular Cell*, 25: 1-14 (2007).
International Search Report for International Application PCT/US08/04516, dated Sep. 10, 2008.
International Search Report for International Application PCT/US2009/047423, dated May 3, 2010.
International Search Report for International Application PCT/US2009/057692, dated Jun. 30, 2010.
Supplementary European Search Report for Application No. EP 08742630.0, dated Mar. 25, 2010.
Supplementary European Search Report for Application No. EP 09763816, dated Nov. 29, 2012.
Partial European Search Report for Application No. EP12003893, dated Jun. 24, 2013.
Non-Final Office Action for U.S. Appl. No. 10/997,146, mailed Nov. 3, 2006.
Final Office Action for U.S. Appl. No. 10/997,146, mailed Aug. 14, 2007.
Non-Final Office Action for U.S. Appl. No. 10/997,146, mailed Jul. 22, 2008.
Non-Final Office Action for U.S. Appl. No. 10/997,146, mailed Apr. 9, 2009.
Non-Final Office Action for U.S. Appl. No. 12/703,015, mailed Oct. 28, 2010.
Final Office Action for U.S. Appl. No. 12/703,015, mailed Jul. 8, 2011.
Non-Final Office Action for U.S. Appl. No. 12/703,061, mailed Oct. 28, 2010.
Final Office Action for U.S. Appl. No. 12/703,061, mailed Jul. 14, 2011.
Non-Final Office Action for U.S. Appl. No. 12/703,061, mailed Sep. 19, 2011.
Notice of Allowance in U.S. Appl. No. 10/997,146, mailed Jan. 26, 2010.
Notice of Allowance in U.S. Appl. No. 12/703,015, mailed Sep. 16, 2011.
Non-Final Office Action for U.S. Appl. No. 12/595,041, mailed May 9, 2012.
Final Office Action for U.S. Appl. No. 12/595,041, mailed Dec. 7, 2012.
Non-Final Office Action for U.S. Appl. No. 13/646,411, mailed Feb. 27, 2013.
Non-Final Office Action for U.S. Appl. No. 13/119,891, mailed May 15, 2013.
Non-Final Office Action for U.S. Appl. No. 12/703,061, mailed Aug. 20, 2013.
Non-Final Office Action for U.S. Appl. No. 13/646,444, mailed Aug. 20, 2013.
Non-Final Office Action for U.S. Appl. No. 13/646,430, mailed Sep. 20, 2013.
Non-Final Office Action for U.S. Appl. No. 13/646,420, mailed Sep. 23, 2013.
Non-Final Office Action for U.S. Appl. No. 12/595,041, mailed Oct. 2, 2013.
Non-Final Office Action for U.S. Appl. No. 13/646,411, mailed Oct. 31, 2013.
Non-Final Office Action for U.S. Appl. No. 13/119,891, mailed Jan. 2, 2014.
Non-Final Office Action for U.S. Appl. No. 12/997,815, mailed Jan. 3, 2014.
Final Office Action for U.S. Appl. No. 13/646,430, mailed Apr. 1, 2014.
Final Office Action for U.S. Appl. No. 13/646,444, mailed Apr. 2, 2014.

(56) References Cited

OTHER PUBLICATIONS

Final Office Action for U.S. Appl. No. 12/703,061, mailed Apr. 11, 2014.
Final Office Action for U.S. Appl. No. 13/646,411, mailed May 9, 2014.
Non-Final Office Action for U.S. Appl. No. 13/646,420, mailed May 27, 2014.
Final Office Action for U.S. Appl. No. 12/595,041, mailed May 30, 2014.
Final Office Action for U.S. Appl. No. 12/997,815, mailed Jul. 15, 2014.
Final Office Action for U.S. Appl. No. 13/119,891, mailed Aug. 18, 2014.
Notice of Allowance for U.S. Appl. No. 12/703,061, dated Nov. 7, 2014.
Notice of Allowance for U.S. Appl. No. 13/646,411, dated Dec. 8, 2014.
Non-Final Office Action for U.S. Appl. No. 13/646,430, dated Dec. 8, 2014.
Non-Final Office Action for U.S. Appl. No. 12/595,041, mailed Apr. 3, 2015.
Notice of Allowance for U.S. Appl. No. 14/923,321, mailed Mar. 24, 2017.

\* cited by examiner

SEQUENCE LISTING

```
<160> NUMBER OF SEQ ID NOS: 48

<210> SEQ ID NO 1
<211> LENGTH: 22
<212> TYPE: DNA
<213> ORGANISM: Artificial Sequence
<220> FEATURE:
<223> OTHER INFORMATION: c-Myc forward primer

<400> SEQUENCE: 1
acctaactcg aggaggagct gg                                              22

<210> SEQ ID NO 2
<211> LENGTH: 21
<212> TYPE: DNA
<213> ORGANISM: Artificial Sequence
<220> FEATURE:
<223> OTHER INFORMATION: c-Myc reverse primer

<400> SEQUENCE: 2
tccacatagc gtaaaaggag c                                               21

<210> SEQ ID NO 3
<211> LENGTH: 20
<212> TYPE: DNA
<213> ORGANISM: Artificial Sequence
<220> FEATURE:
<223> OTHER INFORMATION: Klf4 forward primer

<400> SEQUENCE: 3
acactgtctt cccacgaggg                                                 20

<210> SEQ ID NO 4
<211> LENGTH: 21
<212> TYPE: DNA
<213> ORGANISM: Artificial Sequence
<220> FEATURE:
<223> OTHER INFORMATION: Klf4 reverse primer

<400> SEQUENCE: 4
ggcattaaag cagcgtatcc a                                               21

<210> SEQ ID NO 5
<211> LENGTH: 19
<212> TYPE: DNA
<213> ORGANISM: Artificial Sequence
<220> FEATURE:
<223> OTHER INFORMATION: Sox2 forward primer

<400> SEQUENCE: 5
cattaacggc acactgccc                                                  19

<210> SEQ ID NO 6
<211> LENGTH: 21
<212> TYPE: DNA
<213> ORGANISM: Artificial Sequence
<220> FEATURE:
```

```
<223> OTHER INFORMATION: Sox2 reverse primer

<400> SEQUENCE: 6
ggcattaaag cagcgtatcc a                                              21

<210> SEQ ID NO 7
<211> LENGTH: 21
<212> TYPE: DNA
<213> ORGANISM: Artificial Sequence
<220> FEATURE:
<223> OTHER INFORMATION: Oct4 forward primer

<400> SEQUENCE: 7
agcctggcct gtctgtcact c                                              21

<210> SEQ ID NO 8
<211> LENGTH: 21
<212> TYPE: DNA
<213> ORGANISM: Artificial Sequence
<220> FEATURE:
<223> OTHER INFORMATION: Oct4 reverse primer

<400> SEQUENCE: 8
ggcattaaag cagcgtatcc a                                              21

<210> SEQ ID NO 9
<211> LENGTH: 20
<212> TYPE: DNA
<213> ORGANISM: Artificial Sequence
<220> FEATURE:
<223> OTHER INFORMATION: GAPDH forward primer

<400> SEQUENCE: 9
ttcaccacca tggagaaggc                                                20

<210> SEQ ID NO 10
<211> LENGTH: 18
<212> TYPE: DNA
<213> ORGANISM: Artificial Sequence
<220> FEATURE:
<223> OTHER INFORMATION: GAPDH reverse primer

<400> SEQUENCE: 10 ccctttggc tccaccct                                                   18

<210> SEQ ID NO 11
<211> LENGTH: 19
<212> TYPE: RNA
<213> ORGANISM: Artificial Sequence
<220> FEATURE:
<223> OTHER INFORMATION: Human Dnmt1-targeting siRNA

<400> SEQUENCE: 11
ggaagaagag uuacuauaa                                                 19

<210> SEQ ID NO 12
<211> LENGTH: 19
<212> TYPE: RNA
<213> ORGANISM: Artificial Sequence
<220> FEATURE:
<223> OTHER INFORMATION: Human Dnmt1-targeting siRNA

<400> SEQUENCE: 12
gagcggaggu gucccaaua                                                 19
```

```
<210> SEQ ID NO 13
<211> LENGTH: 19
<212> TYPE: RNA
<213> ORGANISM: Artificial Sequence
<220> FEATURE:
<223> OTHER INFORMATION: Human Dnmt1-targeting siRNA

<400> SEQUENCE: 13
ggacgacccu gaccucaaa                                              19

<210> SEQ ID NO 14
<211> LENGTH: 19
<212> TYPE: RNA
<213> ORGANISM: Artificial Sequence
<220> FEATURE:
<223> OTHER INFORMATION: Human Dnmt1-targeting siRNA

<400> SEQUENCE: 14
gaacggugcu caugcuuac                                              19

<210> SEQ ID NO 15
<211> LENGTH: 18
<212> TYPE: RNA
<213> ORGANISM: Artificial Sequence
<220> FEATURE:
<223> OTHER INFORMATION: Human Dnmt1-targeting siRNA

<400> SEQUENCE: 15
uuucucccuc agacacuc                                               18

<210> SEQ ID NO 16
<211> LENGTH: 19
<212> TYPE: RNA
<213> ORGANISM: Artificial Sequence
<220> FEATURE:
<223> OTHER INFORMATION: Human Dnmt3a-targeting siRNA

<400> SEQUENCE: 16
gcacaagggu accuacggg                                              19

<210> SEQ ID NO 17
<211> LENGTH: 19
<212> TYPE: RNA
<213> ORGANISM: Artificial Sequence
<220> FEATURE:
<223> OTHER INFORMATION: Human Dnmt3a-targeting siRNA

<400> SEQUENCE: 17
caagagagcg gcuggugua                                              19

<210> SEQ ID NO 18
<211> LENGTH: 19
<212> TYPE: RNA
<213> ORGANISM: Artificial Sequence
<220> FEATURE:
<223> OTHER INFORMATION: Human Dnmt3a-targeting siRNA

<400> SEQUENCE: 18
gcacugaaau ggaaagggu                                              19

<210> SEQ ID NO 19
<211> LENGTH: 19
<212> TYPE: RNA
<213> ORGANISM: Artificial Sequence
<220> FEATURE:
<223> OTHER INFORMATION: Human Dnmt3a-targeting siRNA
```

```
<400> SEQUENCE: 19
gaacugcuuu cuggagugu                                              19

<210> SEQ ID NO 20
<211> LENGTH: 19
<212> TYPE: RNA
<213> ORGANISM: Artificial Sequence
<220> FEATURE:
<223> OTHER INFORMATION: Human Dnmt3b-targeting siRNA

<400> SEQUENCE: 20
gaaaguacgu cgcuucuga                                              19

<210> SEQ ID NO 21
<211> LENGTH: 19
<212> TYPE: RNA
<213> ORGANISM: Artificial Sequence
<220> FEATURE:
<223> OTHER INFORMATION: Human Dnmt3b-targeting siRNA

<400> SEQUENCE: 21
acaaauggcu ucagauguu                                              19

<210> SEQ ID NO 22
<211> LENGTH: 19
<212> TYPE: RNA
<213> ORGANISM: Artificial Sequence
<220> FEATURE:
<223> OTHER INFORMATION: Human Dnmt3b-targeting siRNA

<400> SEQUENCE: 22
gcucuuaccu uaccaucga                                              19

<210> SEQ ID NO 23
<211> LENGTH: 19
<212> TYPE: RNA
<213> ORGANISM: Artificial Sequence
<220> FEATURE:
<223> OTHER INFORMATION: Human Dnmt3b-targeting siRNA

<400> SEQUENCE: 23
uuuaccaccu gcugaauua                                              19

<210> SEQ ID NO 24
<211> LENGTH: 21
<212> TYPE: RNA
<213> ORGANISM: Artificial Sequence
<220> FEATURE:
<223> OTHER INFORMATION: Human Hprt-targeting siRNA

<400> SEQUENCE: 24
ccaguuucac uaaugacaca a                                           21

<210> SEQ ID NO 25
<211> LENGTH: 19
<212> TYPE: RNA
<213> ORGANISM: Artificial Sequence
<220> FEATURE:
<223> OTHER INFORMATION: Mouse Dnmt1-targeting siRNA

<400> SEQUENCE: 25
ggaaagagau ggcuuaaca                                              19

<210> SEQ ID NO 26
<211> LENGTH: 19
```

-continued

```
<212> TYPE: RNA
<213> ORGANISM: Artificial Sequence
<220> FEATURE:
<223> OTHER INFORMATION: Mouse Dnmt1-targeting siRNA

<400> SEQUENCE: 26
gcugggagau ggcgucaua                                              19

<210> SEQ ID NO 27
<211> LENGTH: 19
<212> TYPE: RNA
<213> ORGANISM: Artificial Sequence
<220> FEATURE:
<223> OTHER INFORMATION: Mouse Dnmt1-targeting siRNA

<400> SEQUENCE: 27
gauaagaaac gcagaguug                                              19

<210> SEQ ID NO 28
<211> LENGTH: 19
<212> TYPE: RNA
<213> ORGANISM: Artificial Sequence
<220> FEATURE:
<223> OTHER INFORMATION: Mouse Dnmt1-targeting siRNA

<400> SEQUENCE: 28
gguagagagu uacgacgaa                                              19

<210> SEQ ID NO 29
<211> LENGTH: 19
<212> TYPE: RNA
<213> ORGANISM: Artificial Sequence
<220> FEATURE:
<223> OTHER INFORMATION: Mouse Dnmt3a-targeting siRNA

<400> SEQUENCE: 29
cgcgauuucu ugagucuaa                                              19

<210> SEQ ID NO 30
<211> LENGTH: 19
<212> TYPE: RNA
<213> ORGANISM: Artificial Sequence
<220> FEATURE:
<223> OTHER INFORMATION: Mouse Dnmt3a-targeting siRNA

<400> SEQUENCE: 30 cgaaugugu cuuggugga                                               19

<210> SEQ ID NO 31
<211> LENGTH: 19
<212> TYPE: RNA
<213> ORGANISM: Artificial Sequence
<220> FEATURE:
<223> OTHER INFORMATION: Mouse Dnmt3a-targeting siRNA

<400> SEQUENCE: 31
aaacaucgag gacauuugu                                              19

<210> SEQ ID NO 32
<211> LENGTH: 19
<212> TYPE: RNA
<213> ORGANISM: Artificial Sequence
<220> FEATURE:
<223> OTHER INFORMATION: Mouse Dnmt3a-targeting siRNA

<400> SEQUENCE: 32
```
caagggacuu uaugagggu 19

<210> SEQ ID NO 33
<211> LENGTH: 19
<212> TYPE: RNA
<213> ORGANISM: Artificial Sequence
<220> FEATURE:
<223> OTHER INFORMATION: Mouse Dnmt3b-targeting siRNA

<400> SEQUENCE: 33
gcaaugaucu cucuaacgu 19

<210> SEQ ID NO 34
<211> LENGTH: 19
<212> TYPE: RNA
<213> ORGANISM: Artificial Sequence
<220> FEATURE:
<223> OTHER INFORMATION: Mouse Dnmt3b-targeting siRNA

<400> SEQUENCE: 34
ggaaugcgcu ggguacagu 19

<210> SEQ ID NO 35
<211> LENGTH: 19
<212> TYPE: RNA
<213> ORGANISM: Artificial Sequence
<220> FEATURE:
<223> OTHER INFORMATION: Mouse Dnmt3b-targeting siRNA

<400> SEQUENCE: 35
uaaucuggcu accuucaau 19

<210> SEQ ID NO 36
<211> LENGTH: 19
<212> TYPE: RNA
<213> ORGANISM: Artificial Sequence
<220> FEATURE:
<223> OTHER INFORMATION: Mouse Dnmt3b-targeting siRNA

<400> SEQUENCE: 36
gcaaagguuu auaugaggg 19

<210> SEQ ID NO 37
<211> LENGTH: 21
<212> TYPE: RNA
<213> ORGANISM: Artificial Sequence
<220> FEATURE:
<223> OTHER INFORMATION: Mouse Hprt-targeting siRNA

<400> SEQUENCE: 37
ccaguuucac uaaugacaca a 21

<210> SEQ ID NO 38
<211> LENGTH: 34
<212> TYPE: DNA
<213> ORGANISM: Artificial
<220> FEATURE:
<223> OTHER INFORMATION: sense oligonucleotide
<220> FEATURE:
<221> NAME/KEY: misc_feature
<222> LOCATION: (12)..(12)
<223> OTHER INFORMATION: R = A or G
<220> FEATURE:
<221> NAME/KEY: misc_feature
<222> LOCATION: (21)..(21)
<223> OTHER INFORMATION: W = A or T
<220> FEATURE:
<221> NAME/KEY: misc_feature

```
<222> LOCATION: (27)..(27)
<223> OTHER INFORMATION: R = A or G
<220> FEATURE:
<221> NAME/KEY: misc_feature
<222> LOCATION: (33)..(33)
<223> OTHER INFORMATION: R = A or G

<400> SEQUENCE: 38
cgagctctcc arcacagcct wcatgcarct carc                                 34

<210> SEQ ID NO 39
<211> LENGTH: 34
<212> TYPE: DNA
<213> ORGANISM: Artificial
<220> FEATURE:
<223> OTHER INFORMATION: sense oligonucleotide
<220> FEATURE:
<221> NAME/KEY: misc_feature
<222> LOCATION: (13)..(13)
<223> OTHER INFORMATION: S = C or G
<220> FEATURE:
<221> NAME/KEY: misc_feature
<222> LOCATION: (15)..(15)
<223> OTHER INFORMATION: M = A or C
<220> FEATURE:
<221> NAME/KEY: misc_feature
<222> LOCATION: (21)..(21)
<223> OTHER INFORMATION: W = A or T
<220> FEATURE:
<221> NAME/KEY: misc_feature
<222> LOCATION: (33)..(33)
<223> OTHER INFORMATION: M = C or G

<400> SEQUENCE: 39
cggtaccaag aasamcctgt wcctgcaaat gasc                                 34

<210> SEQ ID NO 40
<211> LENGTH: 34
<212> TYPE: DNA
<213> ORGANISM: Artificial
<220> FEATURE:
<223> OTHER INFORMATION: sense oligonucleotide
<220> FEATURE:
<221> NAME/KEY: misc_feature
<222> LOCATION: (15)..(15)
<223> OTHER INFORMATION: R = A or G
<220> FEATURE:
<221> NAME/KEY: misc_feature
<222> LOCATION: (21)..(21)
<223> OTHER INFORMATION: S = C or G
<220> FEATURE:
<221> NAME/KEY: misc_feature
<222> LOCATION: (30)..(30)
<223> OTHER INFORMATION: Y = C or T

<400> SEQUENCE: 40
cggtaccaga ctgarcatca scaaggacaa ytcc                                 34

<210> SEQ ID NO 41
<211> LENGTH: 28
<212> TYPE: DNA
<213> ORGANISM: Artificial
<220> FEATURE:
<223> OTHER INFORMATION: sense oligonucleotide

<400> SEQUENCE: 41
caagggacgg tttgccttct ctttggaa                                        28

<210> SEQ ID NO 42
<211> LENGTH: 31
<212> TYPE: DNA
```

```
<213> ORGANISM: Artificial
<220> FEATURE:
<223> OTHER INFORMATION: sense oligonucleotide

<400> SEQUENCE: 42
agggatcctt gtgaagggat ctactactgt g                                31

<210> SEQ ID NO 43
<211> LENGTH: 29
<212> TYPE: DNA
<213> ORGANISM: Artificial
<220> FEATURE:
<223> OTHER INFORMATION: sense oligonucleotide

<400> SEQUENCE: 43
gccatttccc caggctgttg tgactcagg                                   29

<210> SEQ ID NO 44
<211> LENGTH: 32
<212> TYPE: DNA
<213> ORGANISM: Artificial
<220> FEATURE:
<223> OTHER INFORMATION: sense oligonucleotide
<220> FEATURE:
<221> NAME/KEY: misc_feature
<222> LOCATION: (9)..(9)
<223> OTHER INFORMATION: S = C or G
<220> FEATURE:
<221> NAME/KEY: misc_feature
<222> LOCATION: (24)..(24)
<223> OTHER INFORMATION: R = A or G
<220> FEATURE:
<221> NAME/KEY: misc_feature
<222> LOCATION: (27)..(27)
<223> OTHER INFORMATION: W = A or T
<220> FEATURE:
<221> NAME/KEY: misc_feature
<222> LOCATION: (30)..(30)
<223> OTHER INFORMATION: R = A or G

<400> SEQUENCE: 44
ggctgcagst tcagtggcag tggrtcwggr ac                               32

<210> SEQ ID NO 45
<211> LENGTH: 21
<212> TYPE: DNA
<213> ORGANISM: Artificial
<220> FEATURE:
<223> OTHER INFORMATION: antisense oligonucleotide

<400> SEQUENCE: 45
tctcagccgg ctccctcagg g                                           21

<210> SEQ ID NO 46
<211> LENGTH: 26
<212> TYPE: DNA
<213> ORGANISM: Artificial
<220> FEATURE:
<223> OTHER INFORMATION: antisense oligonucleotide

<400> SEQUENCE: 46
aaagacctgc agaggccatt cttacc                                      26

<210> SEQ ID NO 47
<211> LENGTH: 28
<212> TYPE: DNA
<213> ORGANISM: Artificial
<220> FEATURE:
<223> OTHER INFORMATION: antisense oligonucleotide
```

```
<400> SEQUENCE: 47
actcacctag gacagtcagc ttggttcc                                              28

<210> SEQ ID NO 48
<211> LENGTH: 31
<212> TYPE: DNA
<213> ORGANISM: Artificial
<220> FEATURE:
<223> OTHER INFORMATION: antisense oligonucleotide

<400> SEQUENCE: 48
atgcgacgtc aactgataat gagccctctc c                                          31
```

REPROGRAMMING OF SOMATIC CELLS

CROSS-REFERENCE TO RELATED APPLICATIONS

This application is a continuation of U.S. application Ser. No. 12/595,041, filed Aug. 25, 2010, which is a national stage filing under 35 U.S.C. 371 of International Application PCT/US2008/004516, filed Apr. 7, 2008, which claims the benefit of U.S. Provisional Application No. 61/036,065, filed Mar. 12, 2008; U.S. Provisional Application No. 60/959,341, filed Jul. 12, 2007; and U.S. Provisional Application No. 60/922,121, filed Apr. 7, 2007. The entire contents of the afore-mentioned applications are incorporated herein by reference.

GOVERNMENT SUPPORT

The invention was supported, in whole or in part, by grants 5-R01-HDO45022, 5-R37-CA084198 and 5-RO1-CA087869 from the National Institutes of Health. The U.S. Government has certain rights in the invention.

BACKGROUND OF THE INVENTION

Embryonic development and cellular differentiation are considered unidirectional pathways because cells undergo a progressive loss of developmental potency during cell fate specification. Two categories of pluripotent stem cells are known to date: embryonic stem cells and embryonic germ cells. Embryonic stem cells are pluripotent stem cells that are derived directly from an embryo. Embryonic germ cells are pluripotent stem cells that are derived directly from the fetal tissue of aborted fetuses. For purposes of simplicity, embryonic stem cells and embryonic germ cells will be collectively referred to as "ES" cells herein.

The success of somatic cell nuclear transfer (SCNT) experiments in mammalian species provided proof that the epigenetic state of adult differentiated cells is not fixed but remains pliable for reprogramming by factors present in the oocyte cytoplasm (Byrne et al., 2007; Jaenisch and Young, 2008; Wakayama and Yanagimachi, 2001). However, the inefficiency and ethical concerns associated with attempting to clone human somatic cells have spurred the field to search for alternative methods to achieve nuclear reprogramming without using oocytes (Jaenisch and Young, 2008). Indeed, fusion of somatic cells to embryonic carcinoma cells or embryonic stem (ES) cells results in epigenetic resetting of the somatic genome but involves the generation of 4N pluripotent cells, limiting the potential therapeutic use of such cells (Cowan et al., 2005; Tada et al., 2001).

Nevertheless, the reprogramming of somatic cells by fusion with ES cells suggested that ES cells, similar to the oocyte cytoplasm, contain factors that can induce nuclear reprogramming. An important breakthrough was achieved by Yamanaka and colleagues, who succeeded in directly reprogramming fibroblasts into induced pluripotent stem (iPS) cells by transduction of the four transcription factors Oct4, Sox2, Klf4 and c-Myc (Takahashi and Yamanaka, 2006). Although the initially obtained iPS cells were not normal, several groups have since advanced the direct reprogramming technique by generating iPS cells that are epigenetically and developmentally indistinguishable from embryo-derived ES cells (Maherali, 2007; Meissner et al., 2007; Okita et al., 2007; Wernig et al., 2007). Moreover, transgenic expression of c-Myc was found to be dispensable for reprogramming, though it accelerated and enhanced the efficiency of reprogramming (Nakagawa et al., 2008; Wernig et al., 2008). Finally, it has also been shown that human iPS cells can be generated by transduction of defined factors into somatic cells (Park at al., 2008; Takahashi et al., 2007; Yu et al., 2007).

Despite the work that has been done to date, it remains unknown whether terminally differentiated cells can be reprogrammed to pluripotency with defined factors, or whether only less differentiated cells such as somatic stem cells can undergo nuclear reprogramming to pluripotency. Moreover, it is unclear whether progressive differentiation of the donor cells affects the efficiency of in vitro reprogramming.

SUMMARY OF THE INVENTION

The present invention provides engineered somatic cells, in which one or more endogenous pluripotency gene(s) is operably linked to a selectable marker in such a manner that the expression of the selectable marker substantially matches the expression of the endogenous pluripotency gene to which the marker is linked. The invention also provides transgenic mice containing these engineered somatic cells.

The present invention also provides methods for reprogramming somatic cells to a less differentiated state. In certain of the methods, engineered somatic cells of the invention are treated with an agent. Cells that express the selectable marker are then selected, and assessed for pluripotency characteristics. The treatment with an agent may be contacting the cells with an agent which alters chromatin structure, or may be transfecting the cells with at least one pluripotency gene, or both.

The present invention further provides methods for identifying an agent that reprograms somatic cells to a less differentiated state. In certain of the methods, the engineered somatic cells described above are contacted with a candidate agent. Cells that express the selectable marker are then selected, and assessed for pluripotency characteristics. The presence of at least a subset of pluripotency characteristics indicates that the agent is capable of reprogramming somatic cells to a less-differentiated state. The agents identified by the present invention can then by used to reprogram somatic cells by contacting somatic cells with the agents.

The present invention also provides methods for identifying a gene that causes the expression of at least one endogenous pluripotency gene in somatic cells. In certain of the methods, the engineered somatic cells are transfected with a cDNA library prepared from a pluripotent cell, such as an ES cell. The cells that express the appropriate selectable marker are then selected, and the expression of the appropriate endogenous pluripotency gene is examined. The expression of an endogenous pluripotency gene indicates that the cDNA encodes a protein whose expression in the cell results in, directly or indirectly, expression of the endogenous pluripotency gene.

The invention provides methods of deriving reprogrammed somatic cells from somatic cells that have not been genetically modified. The invention provides methods of deriving reprogrammed somatic cells without use of genetic selection or, in some embodiments, without use of chemical selection. Reprogrammed somatic cells are derived from non-engineered somatic cells according to the invention by, for example, introducing reprogramming agents into non-engineered somatic cells and/or expressing such agents therein and selecting reprogrammed cells by any of a variety of methods that do not require presence of exogenous genetic material within the cells.

In some embodiments, the methods employ morphological criteria to identify reprogrammed somatic cells from among a population of somatic cells that are not reprogrammed. In some embodiments, the methods employ morphological criteria to identify somatic cells that have been reprogrammed to an ES-like state from among a population of cells that are not reprogrammed or are only partly reprogrammed to an ES-like state.

In some embodiments, the methods employ complement-mediated lysis to eliminate at least some non-reprogrammed somatic cells from a population of cells that contains at least some reprogrammed somatic cells.

The present invention further provides methods for treating a condition in an individual in need of such treatment. In certain embodiments, somatic cells are obtained from the individual and reprogrammed by the methods of the invention under conditions suitable for the cells to develop into cells of a desired cell type. The reprogrammed cells of a desired cell type are then harvested and introduced into the individual to treat the condition. In certain further embodiments, the somatic cells obtained from the individual contain a mutation in one or more genes. In these instances, in certain embodiments the methods are modified so that the somatic cells obtained from the individual are first treated to restore the one or more normal gene(s) to the cells such that the resulting cells carry the normal endogenous gene, which are then introduced into the individual.

In certain further embodiments, the somatic cells obtained from the individual are engineered to express one or more genes following their removal from the individual. The cells may be engineered by introducing a gene or expression cassette comprising a gene into the cells. The gene or a portion thereof may be flanked by sites for a site-specific recombinase.

The gene may be one that is useful for purposes of identifying, selecting, and/or generating a reprogrammed cell. In certain embodiments the gene encodes an expression product that causes a reduction in DNA methylation in the cell. For example, the gene may encode an RNA that interferes with expression of a DNA methyltransferase, e.g., DNA methyltransferase 1, 3a, or 3b (Dnmt1, 3a, 3b). The RNA may be a short hairpin RNA (shRNA) or microRNA precursor. In certain embodiments the RNA is a precursor that is processed intracellularly to yield a short interfering RNA (siRNA) or microRNA (miRNA) that inhibits expression of Dnmt1, 3a, or 3b. In certain embodiments the gene encodes a marker that is usable for positive and for negative selection.

In certain embodiments the gene is one that contributes to initiating and/or maintaining the reprogrammed state. In certain embodiments the gene is one whose expression product contributes to initiating the reprogrammed state (and in certain embodiments is necessary for maintaining the reprogrammed state) but which is dispensable for maintaining the reprogrammed state. In these instances, in certain embodiments the methods include a step of treating the engineered cells after reprogramming in order to reduce or eliminate expression of the gene. In methods in which the reprogrammed cells are differentiated in vitro or in vivo after reprogramming, the treatment to reduce or eliminate expression of the gene may occur before or after the reprogrammed cells differentiate. The treatment may comprise causing excision of at least a portion of the introduced gene, e.g., by introducing or expressing a recombinase in the cells. In certain embodiments the gene is one whose expression product contributes to maintaining the reprogrammed state (and in certain embodiments is necessary for maintaining the reprogrammed state) but which is dispensable once the reprogrammed cells have differentiated into a desired cell type. In these embodiments the methods may include a step of treating the engineered reprogrammed cells after their differentiation so as to reduce or eliminate expression of the gene.

In certain other embodiments, methods of the invention can be used to treat individuals in need of a functional organ. In the methods, somatic cells are obtained from an individual in need of a functional organ, and reprogrammed by the methods of the invention to produce reprogrammed somatic cells. Such reprogrammed somatic cells are then cultured under conditions suitable for development of the reprogrammed somatic cells into a desired organ, which is than introduced into the individual. The methods are useful for treating any one of the following conditions: a neurological, endocrine, structural, skeletal, vascular, urinary, digestive, integumentary, blood, autoimmune, inflammatory, or muscular condition.

The present invention also provides methods for producing a cloned animal. In the methods, a somatic cell is isolated from an animal having desired characteristics, and reprogrammed using the methods of the invention to produce one or more reprogrammed pluripotent somatic cell ("RPSC"). The RPSCs are then inserted into a recipient embryo, and the resulting embryo is cultured to produce an embryo of suitable size for implantation into a recipient female, which is then transferred into a recipient female to produce a pregnant female. The pregnant female is maintained under conditions appropriate for carrying the embryo to term to produce chimeric animal progeny, which is then bred with a wild type animal to produce a cloned animal.

In certain embodiments, the RPSCs may alternatively be cryopreserved for future cloning uses. In certain other embodiments, genetic modification, such as a targeted mutation, may be introduced into the RPSCs prior to its insertion into a recipient embryo.

The present invention also provides methods for producing a cloned avian. In the methods, a somatic cell is isolated from an avian having desired characteristics, and reprogrammed using the methods of the invention to produce one or more reprogrammed pluripotent somatic cell ("RPSC"). The RPSCs are then inserted into eggs that are unable to develop into an embryo, and the resulting eggs are then incubated to produce avian offspring having the genotype of the RPSC, thereby producing a cloned avian.

It is contemplated that all embodiments described above are applicable to all different aspects of the invention. It is also contemplated that any of the above embodiments can be freely combined with one or more other such embodiments whenever appropriate.

As described herein, transgenic and inducible expression of four transcription factors (Oct4, Sox2, Klf4, and c-Myc) was used to reprogram mouse B lymphocytes. These factors were sufficient to convert non-terminally differentiated B cells that have undergone partial B cell receptor rearrangements to a pluripotent state. Reprogramming of mature B cells required additional ectopic expression of a myeloid transcription factor CCAAT/enhancer-binding-protein-α (C/EBPα), known for its ability to interrupt the transcriptional state maintaining B cell identity. Multiple iPS lines were clonally derived from both non-fully and fully differentiated mature B lymphocytes, and gave rise to adult chimeras, to late term embryos when injected into tetraploid blastocysts, and contributed to the germline. Work described herein provides definitive proof for the direct nuclear reprogramming of terminally differentiated adult cells to pluripotency.

Accordingly, in one embodiment the invention relates to a method of reprogramming a differentiated somatic cell to a pluripotent state, comprising the steps of contacting a differentiated somatic cell with at least one reprogramming agent that contributes to reprogramming of said cell to a pluripotent state; maintaining said cell under conditions appropriate for proliferation of the cell and for activity of the at least one reprogramming agent for a period of time sufficient to begin reprogramming of the cell; and functionally inactivating the at least one reprogramming agent.

In another embodiment the invention relates to a method of reprogramming a differentiated somatic cell to a pluripotent state, comprising the steps of providing a differentiated somatic cell that contains at least one exogenously introduced factor that contributes to reprogramming of said cell to a pluripotent state; maintaining the cell under conditions appropriate for proliferation of the cell and for activity of the at least one exogenously introduced factor for a period of time sufficient to activate at least one endogenous pluripotency gene; and functionally inactivating the at least one exogenously introduced factor.

In a further embodiment the invention pertains to a method of selecting a differentiated somatic cell that has been reprogrammed to a pluripotent state, comprising the steps of providing a differentiated somatic cell that contains at least one exogenously introduced factor that contributes to reprogramming of the cell to a pluripotent state; maintaining the cell under conditions appropriate for proliferation of the cell and for activity of the at least one exogenously introduced factor for a period of time sufficient to activate at least one endogenous pluripotency gene; functionally inactivating the at least one exogenously introduced factor; and differentiating or distinguishing between cells which display one or more markers of pluripotency and cells which do not. In one embodiment differentiating or distinguishing between cells which display one or more markers of pluripotency and cells which do not comprises selection or enrichment for cells displaying one or more markers of pluripotency and/or selection against cells which do not display one or more markers of pluripotency.

In some embodiments of the invention the differentiated somatic cell is partially differentiated. In other embodiments of the invention the differentiated somatic cell is fully differentiated.

In some embodiments of the invention the differentiated somatic cell is cell of hematopoetic lineage; in some embodiments the differentiated somatic cell is obtained from peripheral blood. In one embodiment of the invention the differentiated somatic cell is an immune system cell. In one embodiment the differentiated somatic cell is a macrophage. In one embodiment the differentiated somatic cell is a lymphoid cell. In other embodiments of the invention the differentiated somatic cell is a B cell, such as an immature (e.g., pro-B cell or pre-B cell) or mature (e.g., non-naïve) B-cell.

In some embodiments of the invention the at least one exogenously introduced factor is a polynucleotide. In other embodiments the at least one exogenously introduced factor is a polypeptide. In one embodiment the at least one exogenously introduced factor is selected from the group consisting of Oct4, Sox2, Klf-4, Nanog, Lin28, c-Myc and combinations thereof. In particular embodiments of the invention the differentiated somatic cell contains exogenously introduced Oct4, Sox2, and Klf-4 exogenously introduced Oct4, Sox2, Klf-4 and c-Myc.

In one embodiment of the invention the at least one exogenously introduced factor is selected from the group consisting of Oct4, Sox2, Klf-4, c-Myc and combinations thereof and the differentiated somatic cell further contains at least one exogenously introduced factor (e.g., a polynucleotide or polypeptide) capable of inducing dedifferentiation of the differentiated somatic cell. In some embodiments the factor capable of inducing dedifferentiation of said differentiated somatic cell is selected from the group consisting of at least one polynucleotide which downregulates B cell late specific markers, at least one polynucleotide which inhibits expression of Pax5, at least one polypeptide which downregulates B cell late specific markers, at least one polypeptide which inhibits expression of Pax5, and combinations thereof. In one embodiment of the invention the factor capable of inducing dedifferentiation of said differentiated somatic cell is C/EBPα or a human homolog of C/EBPα.

In particular embodiments of the invention the at least one exogenously introduced factor is introduced using a vector, e.g., an inducible vector or a conditionally expressed vector. In one aspect the at least one exogenously introduced factor is introduced using a vector which is not subject to methylation-mediated silencing. In yet another embodiment the at least one exogenously introduced factor is introduced using a viral vector such as a retroviral or lentiviral vector.

In one embodiment of the invention the differentiated somatic cell is maintained in the presence of hematopoetic cytokines and growth factors or is cultured on media comprising bone marrow stromal cells.

In some embodiments of the present invention the endogenous pluripotency gene is selected from the group consisting of Nanog, Oct4, Sox2 and combinations thereof. In other embodiments the endogenous pluripotency gene is co-expressed with a selectable marker, such as an antibiotic resistance gene or luminescent marker. In particular embodiments the differentiated somatic cell further comprises at least one polynucleotide encoding a selectable marker operably linked to expression control elements that regulate expression of said at least one endogenous pluripotency gene. In specific embodiments the differentiated somatic cell comprises a selectable gene in the Oct4 locus, the Nanog locus, or both the Oct4 and Nanog loci. In a certain embodiment the at least one exogenously introduced factor is introduced using an inducible vector and wherein functionally inactivating said at least one exogenously introduced factor comprises rendering the conditions under which said cell is maintained unsuitable for inducible expression of said vector.

In some embodiments of the invention, markers of pluripotency are selected from the group consisting of expression of a pluripotency gene, expression of a gene whose expression is a direct or indirect result of expression of a pluripotency gene, expression of alkaline phosphatase, expression of SSEA1, expression of SSEA3, expression of SSEA4, expression of TRAF-60, expression of Nanog, expression of Oct4, expression of Fxb15, morphology characteristic of an ES cell or an ES cell colony, ability to participate in formation of chimeras that survive to term, ability to differentiate into cells having characteristics of endoderm, mesoderm and ectoderm when injected into SCID mice, presence of two active X chromosomes, resistance to DNA methylation, and combinations thereof.

The invention also relates to an isolated pluripotent cell derived from a reprogrammed differentiated somatic cell in accordance with methods of the invention. In particular the invention relates to a purified population of somatic cells comprising at least 70% pluripotent cells derived from reprogrammed differentiated somatic cells.

The invention further relates to an isolated pluripotent cell produced by a method comprising (a) providing a differentiated somatic cell that contains at least one exogenously introduced factor that contributes to reprogramming of said cell to a pluripotent state; (b) maintaining said cell under conditions appropriate for proliferation of said cell and for activity of said at least one exogenously introduced factor for a period of time sufficient to activate at least one endogenous pluripotency gene; (c) functionally inactivating said at least one exogenously introduced factor; and (d) differentiating cells which display one or more markers of pluripotency from cells which do not.

The invention also relates to a purified population of somatic cells comprising at least 70% pluripotent cells derived from reprogrammed differentiated somatic cells produced by a method comprising (a) providing a differentiated somatic cell that contains at least one exogenously introduced factor that contributes to reprogramming of said cell to a pluripotent state; (b) maintaining said cell under conditions appropriate for proliferation of said cell and for activity of said at least one exogenously introduced factor for a period of time sufficient begin reprogramming of said cell or to activate at least one endogenous pluripotency gene; (c) functionally inactivating said at least one exogenously introduced factor; and (d) differentiating cells which display one or more markers of pluripotency and cells which do not.

In another aspect the invention relates to a method of producing a pluripotent cell from a somatic cell, comprising the steps of (a) providing one or more somatic cells that each contain at least one exogenously introduced factor that contributes to reprogramming of said cell to a pluripotent state, wherein said exogenously introduced factor is introduced using an inducible vector which is not subject to methylation-induced silencing; (b) maintaining said one or more cells under conditions appropriate for proliferation of said cells and for activity of said at least one exogenously introduced factor for a period of time sufficient begin reprogramming of said cell or to activate at least one endogenous pluripotency gene; (c) functionally inactivating said at least one exogenously introduced factor; (d) selecting one or more cells which display a marker of pluripotency; (e) generating a chimeric embryo utilizing said one or more cells which display a marker of pluripotency; (f) obtaining one or more somatic cells from said chimeric embryo; (g) maintaining said one or more somatic cells under conditions appropriate for proliferation of said cells and for activity of said at least one exogenously introduced factor for a period of time sufficient to begin reprogramming said cell or to activate at least one endogenous pluripotency gene; and (h) differentiating between cells which display one or more markers of pluripotency and cells which do not. In a particular embodiment the method yields a purified population of somatic cells comprising at least 70% pluripotent cells derived from reprogrammed differentiated somatic cells The invention also relates to an isolated pluripotent cell produced by a method comprising (a) providing one or more somatic cells that each contain at least one exogenously introduced factor that contributes to reprogramming of said cell to a pluripotent state, wherein said exogenously introduced factor is introduced using an inducible vector which is not subject to methylation-induced silencing; (b) maintaining said one or more cells under conditions appropriate for proliferation of said cells and for activity of said at least one exogenously introduced factor for a period of time sufficient to begin reprogramming said cell or to activate at least one endogenous pluripotency gene; (c) functionally inactivating said at least one exogenously introduced factor; (d) selecting one or more cells which display a marker of pluripotency; (e) generating a chimeric embryo utilizing said one or more cells which display a marker of pluripotency; (f) obtaining one or more somatic cells from said chimeric embryo; (g) maintaining said one or more somatic cells under conditions appropriate for proliferation of said cells and for activity of said at least one exogenously introduced factor for a period of time sufficient to activate at least one endogenous pluripotency gene; and (h) differentiating cells which display one or more markers of pluripotency and cells which do not.

In preferred embodiments of the invention the methods yield a purified population of somatic cells comprising at least 70% (e.g., 70%, 75%, 80%, 85%, 90%, 95%, 99%) pluripotent cells derived from reprogrammed differentiated somatic cells. In particular embodiments the pluripotent cells are genetically homogenous.

The invention also pertains to a purified population of somatic cells comprising at least 70% pluripotent cells derived from reprogrammed differentiated somatic cells produced by a method comprising (a) providing one or more somatic cells that each contain at least one exogenously introduced factor that contributes to reprogramming of said cell to a pluripotent state, wherein said exogenously introduced factor is introduced using an inducible vector which is not subject to methylation-induced silencing; (b) maintaining said one or more cells under conditions appropriate for proliferation of said cells and for activity of said at least one exogenously introduced factor for a period of time sufficient to begin reprogramming of said cell or to activate at least one endogenous pluripotency gene; (c) functionally inactivating said at least one exogenously introduced factor; (d) selecting one or more cells which display a marker of pluripotency; (e) generating a chimeric embryo utilizing said one or more cells which display a marker of pluripotency; (f) obtaining one or more somatic cells from said chimeric embryo; (g) maintaining said one or more somatic cells under conditions appropriate for proliferation of said cells and for activity of said at least one exogenously introduced factor for a period of time sufficient to begin reprogramming said cell or to activate at least one endogenous pluripotency gene; and (h) differentiating cells which display one or more markers of pluripotency and cells which do not.

The invention also encompasses a method of reprogramming a differentiated immune cell to a pluripotent state, comprising the steps of (a) providing a differentiated immune cell that contains exogenously introduced Oct4, Sox2, Klf-4 and c-Myc, each under the control of an inducible vector, and further contains exogenously introduced C/EBPα; (b) maintaining said cell under conditions appropriate for proliferation of said cell and for activity of Oct4, Sox2, Klf-4, c-Myc and C/EBPα for a period of time sufficient to activate endogenous Nanog and/or Oct4; and (c) functionally inactivating exogenously introduced Oct4, Sox2, Klf-4 and c-Myc. In one embodiment of the method said inducible vector is not subject to methylation-derived silencing.

The invention also relates to a purified population of immune cells comprising at least 70% pluripotent cells derived from reprogrammed differentiated immune cells produced by a method comprising the steps of (a) providing a differentiated immune cell that contains exogenously introduced Oct4, Sox2, Klf-4 and c-Myc, each under the control of an inducible vector, and further contains exogenously introduced C/EBPα; (b) maintaining said cell under conditions appropriate for proliferation of said cell and for activity of Oct4, Sox2, Klf-4, c-Myc and C/EBPα for a period of time sufficient to activate endogenous Nanog and/or Oct4; and (c) functionally inactivating exogenously introduced Oct4, Sox2, Klf-4 and c-Myc.

The invention also relates to a method of identifying a reprogramming agent comprising (a) providing one or more somatic cells that each contain at least one exogenously introduced factor that contributes to reprogramming of said cell to a pluripotent state, wherein each of said exogenously introduced factors is introduced using an inducible vector which is not subject to methylation-induced silencing and the expression of which is controlled by regulatory elements induced by distinct inducers; (b) maintaining said one or more cells under conditions appropriate for proliferation of said cells and for activity of said at least one exogenously introduced factor for a period of time sufficient to reprogram said cell or to activate at least one endogenous pluripotency gene; (c) functionally inactivating said at least one exogenously introduced factor; (d) selecting one or more cells which display a marker of pluripotency; (e) generating a chimeric embryo utilizing said one or more cells which display a marker of pluripotency; (f) obtaining one or more somatic cells from said chimeric embryo; (g) maintaining said one or more somatic cells under conditions appropriate for proliferation of said cells and for activity of said at least one exogenously introduced factor wherein activity of said at least one exogenously introduced factor is insufficient by itself to activate at least one endogenous pluripotency gene; (h) contacting the somatic cell of (g) with one or more candidate reprogramming agents; and (i) identifying cells contacted with said one or more candidate reprogramming agents which display one or more markers of pluripotency, wherein candidate reprogramming agents which induce the somatic cell of (g) to display one or more markers of pluripotency are identified as reprogramming agents.

BRIEF DESCRIPTION OF THE DRAWINGS

As illustrated in FIG. 2A, an IRES-GfpNeo fusion cassette was inserted into the BclI site downstream of Oct4 exon 5. Correctly targeted ES cell clones were screened by Southern analysis of NcoI digested DNA using a 5' external probe. The Nanog gene was targeted as described in Mitsui et al., *Cell* 123(5):631 (2003). FIG. 2B shows the total number (left scale) and percentages (right scale) of AP- and strong SSEA1-positive colonies of Oct4- and Nanogneo MEFs 4 weeks after infection and neo selection.

DETAILED DESCRIPTION OF THE INVENTION

Figure 1:
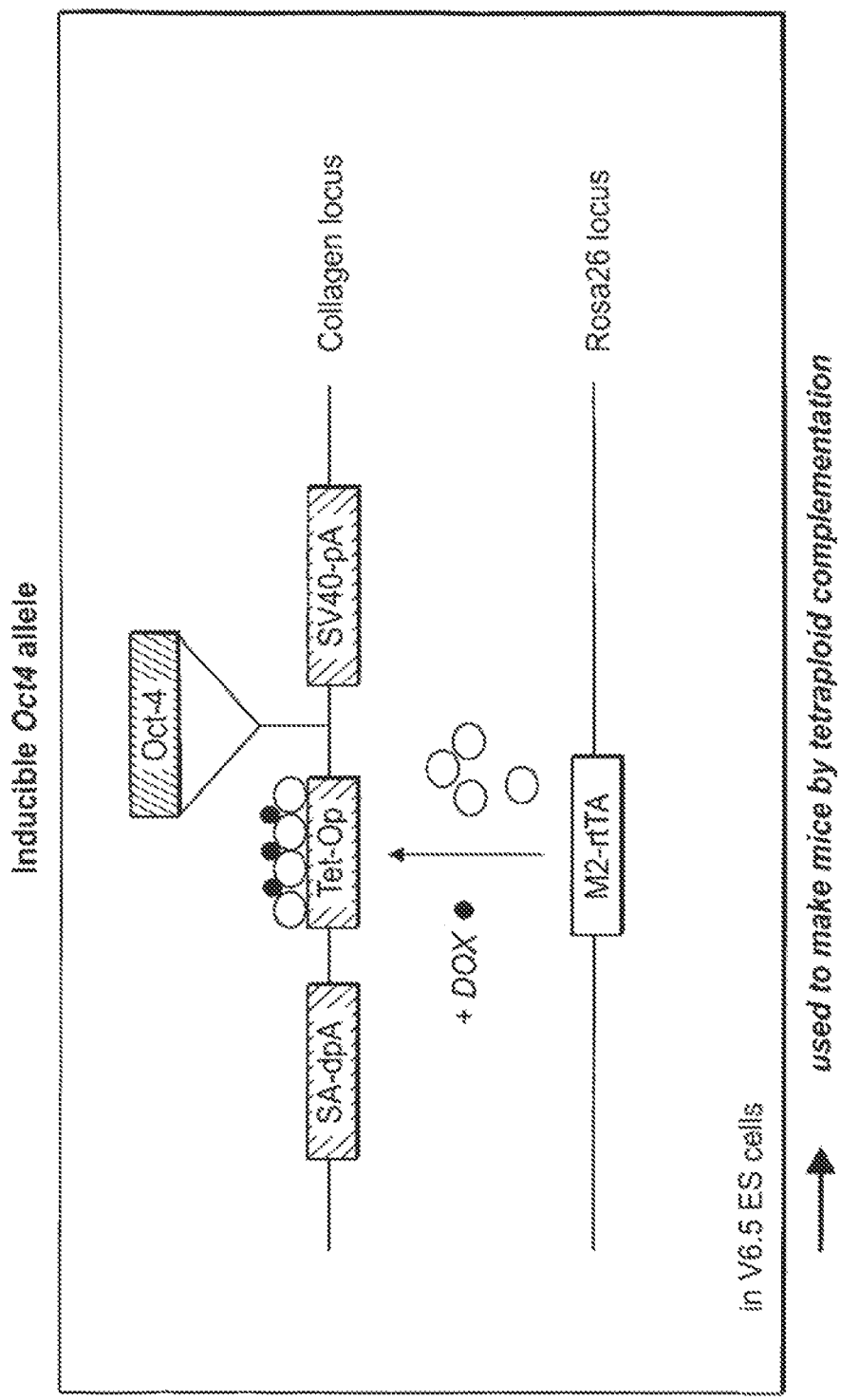
FIG. 1 is a schematic illustration of an inducible Oct4 allele. The first integration vector, inducible Oct4 integration vector, contains an Oct4 gene driven by a tetracycline-inducible promoter (Tet-Op). The Tet-Op-Oct4 cassette is flanked by a splice-acceptor double poly-A signal (SA-dpA) at its 5' end and a SV40 polyA tail (SV40-pA) at its 3' end. The second integration vector, tetracycline activator integration vector, contains a mutant form of tetracycline activator, M2-rtTA, which is more responsive to doxycycline (Dox) induction than the wild type activator (Urlinger at al., *Prod Natl Acad Sci USA* 97(14):7963 2000)).

Nuclear reprogramming, which pertains to the concept of rewiring the epigenetic state of a somatic nucleus to that of another cell type, can be achieved by different approaches. The most recently established strategy to reprogram somatic cells to pluripotency involves direct ectopic expression of defined transcription factors in somatic cells (Okita at al., 2007; Takahashi and Yamanaka, 2006; Wernig et al., 2007). This enforced factor expression appears to initiate a sequence of stochastic events occurring over a relatively extended time period in culture that eventually leads to generation of a small fraction of cells that have acquired a stable pluripotent state (Jaenisch and Young, 2008). The transduced factors are required for an initial period of time in the reprogramming process (Brambrink at al., 2008; Stadtfeld et al., 2008), during which they may interact with endogenous pluripotency genes (Boyer et al., 2005; Loh at al., 2006) and gradually induce epigenetic changes that subsequently sustain a stable epigenetic state that is indistinguishable from that of inner cell mass-derived ES cells. During this process, the de novo methyltransferases Dnmt3a and Dnmt3b also become activated and in turn methylate and silence the virally transduced factors. Silencing of the exogenous factors is crucial for subsequent differentiation of the iPS cells (Brambrink at al., 2008; Takahashi et al., 2007; Wernig at al., 2007; Stadfeld et al., 2008).

In the development of cells along the B cell lineage, sequential intrinsic genetic DNA rearrangements in the heavy and light chain immunoglobulin loci genetically mark the different consecutive stages of B cell maturation (Jung et al., 2006). Cells at the Pro-B stage of development initiate immunoglobulin rearrangements, a process involving the assembly of V (variable), D (diversity) and J (joining) gene segments. Assembly of the heavy chain locus (IgH) precedes that of the light chain loci (IgL) (Jung et al., 2006). In addition, the rearrangements of the IgH locus are sequential, with $D_H$ to $J_H$ joining occurring on both alleles prior to $V_H$ to $D_HJ_H$ segment rearrangement (Papavasiliou et al., 1997). The productive assembly of $V_H$-$D_HJ_H$ variable gene region indirectly signals differentiation to the next stage, in which IgL chains are assembled with Igκ rearrangement generally preceding that of Igλ (Papavasiliou et al., 1997). Productive IgL chain generation eventually leads to the association of functional light and heavy chain proteins, which together form the B cell receptor on the cell surface. The resulting B cells can migrate to the periphery where, upon encountering a cognate antigen, they can exert proper immunological functions (Schlissel, 2003).

Work described herein used cells from this highly ordered developmental pathway that carry distinct, sequentially-acquired, genetic "fingerprints" that would allow accurate retrospective assessment of the developmental stage of the donor B cell nucleus that was able to generate the respective monoclonal iPS line. In particular, as described herein, iPS cells were generated from pro- and pre-B cells by transduction with the reprogramming factors Oct4, Sox2, c-Myc and Klf4 and from mature B cells by the additional over expression of C/EBPα, a well-characterized myeloid transcription factor. This work shows that the reprogrammed cells carried the genetic rearrangements characteristic of donor non-terminally differentiated and mature terminally differentiated B cells and were able to generate adult chimeric mice and contribute to germline. These results indicate that specific combinations of reprogramming factors can reset the genome of terminally differentiated cells to a pluripotent state.

The work described herein provides conclusive evidence that terminally differentiated mature B cells obtained from adult mice can be directly reprogrammed into ES-like cells in vitro. The donor B cell population that eventually underwent successful reprogramming had completed a complex differentiation pathway involving epigenetic and genetic changes: an initial commitment to the hematopoietic and subsequently to the B cell lineage; acquisition of productive heavy and light chain rearrangements; egression from the bone marrow to repopulate peripheral lymphoid organs in adult mice, and as observed in one of the cell lines obtained, acquisition of somatic hypermutations in variable region of B cell receptor genes in response to antigen stimuli. Thus, robust ectopic expression of Oct4, Sox2, Klf-4, c-Myc and C/EBPα transcription factors induced reprogramming of fully differentiated lymphoid cells to pluripotency with a relatively high efficiency of ~1 in 30 cells.

Importantly, results described herein demonstrate that under similar induction levels of Oct4, Sox2, Klf4 and c-Myc transgenes in the B cell lineage, non-terminally differentiated and terminally differentiated B cells respond differently to these factors. Robust reprogramming of fully differentiated mature B lymphocytes to pluripotency was achieved when the C/EBPα transcription factor, which normally plays a role in granulocyte cell fate specification, was initially over-expressed (Ramji and Foka, 2002). Thomas Graf and colleagues (Xie at al., 2004) have shown that overexpression of C/EBPα converted B cells into macrophage-like cells by downregulating B cell late specific markers (e.g., CD19) through inhibition of Pax5 functions and facilitating extinction of the early B cell regulators, EBF1 and E2A transcription factors. In addition, C/EBPα induced up-regulation of components of a myeloid transcriptional network (Laiosa et al., 2006; Xie et al., 2004). These observations are relevant for understanding the mechanisms of reprogramming and suggest a crucial role for C/EBPα in inducing the reprogramming process of mouse mature B lymphocytes. This suggests a number of mutually non-exclusive possibilities:

1) C/EBPα may cross-antagonize key regulators of the B cell transcriptional network that maintain the mature B cell identity. This may facilitate the dedifferentiation of B cells to a less differentiated state, allowing Oct4, Sox2, Klf4 and c-Myc transgene-induced reprogramming. This explanation is consistent with observations that the differentiation state of the donor cells is known to influence the efficiency of reprogramming by nuclear transplantation, as neural and keratinocyte stem cells were more efficiently reprogrammed than other more differentiated cells obtained from the same lineage (Blelloch et al., 2006; Li at al., 2007). As conditional deletion of Pax5 in mature B cells resulted in their dedifferentiation and loss of several mature B cell markers (Cobaleda at al., 2007a), it may be that deletion of Pax5 would also sensitize mature B cells to reprogramming to pluripotency by Oct4, Sox2, Klf4 and c-Myc.

2) C/EBPα may convert mature B cells into macrophage-like cells (Xie at al., 2004) which have a different epigenetic state that possibly allows enhanced accessibility to target genes of Oct4, Sox2, Klf4, and/or c-Myc that would facilitate the efficient induction of the endogenous auto-regulatory loop governing the pluripotent state (Boyer at al., 2005; Loh et al., 2006).

3) C/EBPα-mediated overexpression may enable mature B cells to transition from a state of growing in suspension to become adherent cells in the presence of OP9 cells, which might be a rate-limiting event in their reprogramming.

4) Finally, other combinations of factors than those used in the examples may be able to reprogram mature B lymphocytes under different culture conditions.

Applicants have devised novel methods of reprogramming somatic cells, e.g., partially or fully differentiated somatic cells, to generate pluripotent cells or multipotent cells. It should be noted that the methods of the invention are not intended to encompass prior art methods including, but not limited to, somatic cell nuclear transfer. That is, it is not within the scope of the invention to reprogram a somatic cell by contacting the nucleus of said cell with the intact cytoplasm of an oocyte, i.e., by transferring the nucleus of said cell into an enucleated oocyte. While some embodiments of the invention encompass methods of reprogramming a nucleus of a somatic cell which has been isolated from the cytoplasm in which it is ordinarily contained, and optionally subsequently transferring said nucleus to an enucleated cell of the same or different cell type, these embodiments do not encompass methods in which the reprogramming agent is an enucleated oocyte. Applicants have also devised novel methods to identify agents that, alone or in combination with other factors and/or conditions, reprogram somatic cells.

Certain of the methods of the invention make use of characteristics that differ between ES cells (e.g., ES cells generated using conventional methods described in the Background) and somatic cells. These characteristics distinguish ES cells from somatic cells that have not been reprogrammed and are used as a basis to identify reprogrammed cells (induced pluripotent cells) in certain of the methods.

One such characteristic is the increased ability of ES cells to survive demethylation of genomic DNA relative to somatic cells. Somatic cells are treated in any of a variety of ways that may result in reprogramming, and the cells are subjected to a procedure that results in DNA demethylation. In certain embodiments of the invention, somatic cells that are able to survive the procedure are identified as being reprogrammed or having an increased likelihood of being reprogrammed relative to cells which are not able to survive the procedure. In certain embodiments of the invention a candidate reprogramming agent, e.g., a treatment or factor, that has resulted in at least a portion of the cells becoming resistant to DNA demethylation (i.e., able to survive under conditions of DNA methylation) is identified as an agent useful for reprogramming a somatic cell.

Another characteristic of ES cells that distinguishes them from somatic cells is that ES cells contain two transcriptionally active X chromosomes, whereas in somatic cells one X chromosome is normally largely or completely transcriptionally inactive (see Avner, P. and Heard, E., Nature Reviews Genetics, 2: 59-67, 2001; Eggan, K., et al., Science, 290(5496):1578-81, 2000). According to one embodiment of the invention, somatic cells are treated in any of a variety of ways that may result in reprogramming. The treatment can be, for example, contacting the cells with a candidate reprogramming agent, e.g., a treatment or factor. In certain embodiments of the invention, cells in which both X chromosomes are transcriptionally active are identified as reprogrammed or having an increased likelihood of being reprogrammed relative to cells in which only one X chromosome is transcriptionally active. In certain embodiments of the invention a candidate reprogramming agent, e.g., a treatment or factor, that has resulted in at least a portion of the cells having two transcriptionally active X chromosomes is identified as a treatment useful for reprogramming a somatic cell. In some embodiments, one step of the method involves selecting for cells that have only one transcriptionally active X chromosome, and a subsequent step of the method comprises selecting for cells that have activated their inactive X chromosome.

Certain other of the methods take advantage of the engineered somatic cells designed by Applicants, in which an endogenous gene typically associated with pluripotency ("pluripotency gene") is engineered to be operably linked to a selectable marker in a manner that the expression of the endogenous pluripotency gene substantially matches the expression of the selectable marker. Because pluripotency genes are generally expressed only in pluripotent cells and not in somatic cells, the expression of an endogenous pluripotency gene(s) is an indication of successful reprogramming. Having a selectable marker operably linked to an endogenous pluripotency gene gives one a powerful mechanism to select for potentially reprogrammed somatic cells, which may be a rare occurrence. The resulting cells may be alternatively or additionally assessed for other pluripotency characteristics to confirm whether a somatic cell has been successfully reprogrammed to pluripotency.

Accordingly, in one embodiment the invention relates to a method of reprogramming one or more somatic cells, e.g., partially differentiated or fully/terminally differentiated somatic cells, to a less differentiated state, e.g., a pluripotent or multipotent state. In general the method comprises the steps of contacting the somatic cell or isolated somatic cell nucleus with at least one reprogramming agent that contributes to reprogramming of the cell to a pluripotent state; maintaining the cell under conditions appropriate for proliferation of the cell and for activity of the reprogramming agent for a period of time sufficient to activate an endogenous pluripotency gene, and functionally inactivating the reprogramming agent, e.g., inactivating or removing the reprogramming agent. In further embodiments the invention also relates to reprogrammed somatic cells produced by methods of the invention and to uses of said cells.

Generating pluripotent or multipotent cells by using the methods of the present invention has at least two advantages. First, the methods of the present invention allow one to generate autologous pluripotent cells, which are cells specific to a patient. The use of autologous cells in cell therapy offers a major advantage over the use of non-autologous cells, which are more likely to be subject to immunological rejection. In contrast, autologous cells are less likely to elicit significant immunological responses. Second, the methods of the present invention allow one to generate pluripotent cells without using embryos, oocytes and/or nuclear transfer technology.

TERMINOLOGY

The articles "a", "an" and "the" as used herein, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in haec verba herein. It should also be understood that any embodiment of the invention, e.g., any embodiment found within the prior art, can be explicitly excluded from the claims, regardless of whether the specific exclusion is recited in the specification. For example, any agent may be excluded from the set of candidate reprogramming agents, and any gene can be excluded from the set of pluripotency genes.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". "Approximately" or "about" generally includes numbers that fall within a range of 1% or in some embodiments 5% of a number in either direction (greater than or less than the number) unless otherwise stated or otherwise evident from the context (except where such number would impermissibly exceed 100% of a possible value).

Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, e.g., in Markush group or similar format, it is to be understood that each subgroup of the elements is also disclosed, and any element(s) can be removed from the group.

Certain claims are presented in dependent form for the sake of convenience, but any dependent claim may be rewritten in independent format to include the limitations of the independent claim and any other claim(s) on which such claim depends, and such rewritten claim is to be considered equivalent in all respects to the dependent claim (either amended or unamended) prior to being rewritten in independent format. It should also be understood that, unless clearly indicated to the contrary, in any methods claimed herein that include more than one act, the order of the acts of the method is not necessarily limited to the order in which the acts of the method are recited, but the invention includes embodiments in which the order is so limited. It is contemplated that all embodiments described above are applicable to all different aspects of the invention. It is also contemplated that any of the above embodiments can be freely combined with one or more other such embodiments whenever appropriate.

Somatic Cells

Somatic cells of the invention may be primary cells (non-immortalized cells), such as those freshly isolated from an animal, or may be derived from a cell line (immortalized cells). The cells may be maintained in cell culture following their isolation from a subject. In certain embodiments the cells are passaged once or more than once (e.g., between 2-5, 5-10, 10-20, 20-50, 50-100 times, or more) prior to their use in a method of the invention. In some embodiments the cells will have been passaged no more than 1, 2, 5, 10, 20, or 50 times prior to their use in a method of the invention. They may be frozen, thawed, etc. In certain embodiments of the invention the somatic cells are obtained from a female. The somatic cells used may be native somatic cells, or engineered somatic cells, i.e., somatic cells which have been genetically altered.

Somatic cells of the present invention are typically mammalian cells, such as, for example, human cells, primate cells or mouse cells. They may be obtained by well-known methods and can be obtained from any organ or tissue containing live somatic cells, e.g., blood, bone marrow, skin, lung, pancreas, liver, stomach, intestine, heart, reproductive organs, bladder, kidney, urethra and other urinary organs, etc. Mammalian somatic cells useful in the present invention include, but are not limited to, sertoli cells, endothelial cells, granulosa epithelial, neurons, pancreatic islet cells, epidermal cells, epithelial cells, hepatocytes, hair follicle cells, keratinocytes, hematopoietic cells, melanocytes, chondrocytes, lymphocytes (B and T lymphocytes), erythrocytes, macrophages, monocytes, mononuclear cells, cardiac muscle cells, and other muscle cells, etc. The term "somatic cells", as used herein, also includes adult stem cells. An adult stem cell is a cell that is capable of giving rise to all cell types of a particular tissue. Exemplary adult stem cells include hematopoietic stem cells, neural stem cells, and mesenchymal stem cells.

In some embodiments cells are selected based on their expression of an endogenous marker known to be expressed only or primarily in a desired cell type. For example, vimentin is a fibroblast marker. Other useful markers include various keratins, cell adhesion molecules such as cadherins, fibronectin, CD molecules, etc. The population of somatic cells may have an average cell cycle time of between 18 and 96 hours, e.g., between 24-48 hours, between 48-72 hours, etc. In some embodiments, at least 90%, 95%, 98%, 99%, or more of the cells would be expected to divide within a predetermined time such as 24, 48, 72, or 96 hours.

Methods of the invention may be used to reprogram one or more somatic cells, e.g., colonies or populations of somatic cells. In some embodiments a population of cells of the present invention is substantially uniform in that at least 90% of the cells display a phenotype or characteristic of interest. In some embodiments at least 95%, 96%, 97%, 98%, 99%, 99.5%, 99.8%, 99.9, 99.95% or more of the cells display a phenotype or characteristic of interest. In certain embodiments of the invention the somatic cells have the capacity to divide, i.e., the somatic cells are not post-mitotic. The cells may, for example, have an average cell cycle time (i.e., time required for a cell to complete a single cell division cycle) of between 18-72 hours, e.g., between 24-48 hours when maintained in culture under standard culture conditions known in the art.

Differentiated somatic cells of the invention are partially or completely differentiated. Differentiation is the process by which a less specialized cell becomes a more specialized cell type. Cell differentiation can involve changes in the size, shape, polarity, metabolic activity, gene expression and/or responsiveness to signals of the cell. For example, hematopoietic stem cells differentiate to give rise to all the blood cell types including myeloid (monocytes and macrophages, neutrophils, basophils, eosinophils, erythrocytes, megakaryocytes/platelets, dendritic cells) and lymphoid lineages (T-cells, B-cells, NK-cells). During progression along the path of differentiation, the ultimate fate of a cell becomes more fixed. As shown by work described herein, both partially differentiated somatic cells (e.g., immature B cells such as pre-B cells and pro-B cells) and fully differentiated somatic cells (e.g., mature B cells, non-naïve mature B cells) can be reprogrammed as described herein to produce multipotent or pluripotent cells (also known as "induced pluripotent cells").

Reprogramming and Pluripotent Cells

Differentiation status of cells is a continuous spectrum, with a terminally differentiated state at one end of this spectrum and de-differentiated state (pluripotent state) at the other end. Reprogramming, as used herein, refers to a process that alters or reverses the differentiation status of a somatic cell, which can be either partially or terminally differentiated. Reprogramming includes complete reversion, as well as partial reversion, of the differentiation status of a somatic cell. In other words, the term "reprogramming", as used herein, encompasses any movement of the differentiation status of a cell along the spectrum toward a less-differentiated state. For example, reprogramming includes reversing a multipotent cell back to a pluripotent cell, and reversing a terminally differentiated cell back to either a multipotent cell or a pluripotent cell. In one embodiment, reprogramming of a somatic cell turns the somatic cell all the way back to a pluripotent state. In another embodiment, reprogramming of a somatic cell turns the somatic cell back to a multipotent state. The term "less-differentiated state", as used herein, is thus a relative term and includes a completely de-differentiated state and a partially differentiated state.

A pluripotent cell is a cell that has the potential to divide in vitro for a long period of time (e.g., greater than one year) and has the unique ability to differentiate into cells derived from all three embryonic germ layers—endoderm, mesoderm and ectoderm. Pluripotent cells have the potential to differentiate into the full range of daughter cells having distinctly different morphological, cytological or functional phenotypes unique to a specific tissue. By contrast, descendants of pluripotent cells are restricted progressively in their differentiation potential, with some cells having only one fate. A multipotent cell is a cell that is able to differentiate into some but not all of the cells derived from all three germ layers. Thus, a multipotent cell is a partially differentiated cell. Adult stem cells are also multipotent or partially differentiated cells. Known adult stem cells include, for example, hematopoietic stem cells and neural stem cells.

Treatment of Somatic Cell(s) with Reprogramming Agent

As described herein, one or more (e.g., a population or colony) somatic cells, e.g., differentiated somatic cells, is treated or contacted with at least one reprogramming agent or factor that contributes to reprogramming of said cell. The terms "contact", "contacting", "treat", "treating", etc., are used interchangeably herein and include subjecting a cell to any kind of process or condition or performing any kind of procedure on the cell. The treatment can be, by way of non-limiting example, contacting the cells with a known or candidate reprogramming agent (e.g., an agent which alters the chromatin structure of the cell, an agent which decreases DNA methylation, an agent which decreases histone acetylation) transfecting the cells with a polynucleotide encoding a reprogramming agent, and/or culturing the cells under conditions that differ from standard culture conditions in which such cells are typically maintained. For example, the temperature or pH could be varied. Multiple known or candidate reprogramming agents may be used concurrently/simultaneously or sequentially. In another embodiment, methods of the invention may further include repeating the steps of treating the cells with an agent or factor. The agent used in the repeating treatment may be the same as, or different from, the one used during the first treatment. Reprogramming agents of the invention can be polynucleotides, polypeptides, small molecules, etc.

The cells may be contacted with a reprogramming factor or agent for varying periods of time. In some embodiments the cells are contacted with the agent for a period of time between 1 hour and 30 days. In some embodiments the cells are contacted with the agent for a period of time sufficient to reprogram the cell or to activate an endogenous pluripotency gene. For example, the period may be 1 day, 5 days, 7 days, 10 days, 12 days, 14 days or 20 days. The reprogramming agent may be removed or inactivated prior to performing a selection to enrich for pluripotent cells or assessing the cells for pluripotency characteristics.

According to some embodiments of the invention, after the somatic cell(s) are contacted with the reprogramming agent or factor, they are maintained under conditions appropriate for proliferation of the cell and for activity of the reprogramming agent or factor for a time sufficient to reprogram the cell or to activate at least one endogenous pluripotency gene. Cells may be maintained in culture for varying periods of time while reprogramming takes place, prior to selection of or enrichment for reprogrammed cells. Thus in certain methods, somatic cells which have been contacted with a reprogramming agent or factor are maintained in culture for more than 3 days prior to identifying or selecting for reprogrammed cells. In some methods, said cells are maintained in culture for at least 4, 5, 6, 7, 8, 9, 10, 11, 12, 13, 14, 15, 16, 17, 18, 19, 20, 21 or more days (e.g., between 3-5 weeks) prior to identifying or selecting for reprogrammed cells.

In addition, in particular embodiments of the invention the somatic cells which have been contacted with one or more reprogramming agents according to the described methods are maintained under conditions appropriate for proliferation of said cells. Conditions appropriate for the maintenance and proliferation of particular cell types will be apparent to the skilled artisan. Specialized culture medium may be obtained from commercial sources, or factors necessary or desirable for enhancing the proliferation may be added to standard culture medium. Additional factors and agents may also be added to culture medium, for example, to induce expression of inducible elements in said cells or to inhibit growth of cells which are sensitive to particular agents.

By way of non-limiting example, DNA methylation inhibitors and histone deacelyation inhibitors are two classes of agents that may be used in the methods of the invention; exemplary agents include 5-aza-cytidine, TSA and valproic acid. As described herein, DNA methylation inhibitors are also of use to identify cells that have been reprogrammed, regardless of whether a DNA methylation inhibitor contributes to the reprogramming. Thus in some embodiments of the invention the reprogramming agent is not a DNA methylation inhibitor, e.g., it has no detectable effect on DNA methylation or reduces DNA methylation by less than 1%. In some embodiments the reprogramming agent reduces DNA methylation by less than 5% and/or inhibits DNMT1, 3a, and/or 3b activity by less than 1% or less than 5%.

In certain embodiments of the invention the reprogramming agent or factor is exogenously introduced to the cell. "Exogenously introduced" is used consistently with its meaning in the art to refer to a polynucleotide (or other substance including but not limited to a small molecule or protein) which has been introduced into a cell or an ancestor of the cell from outside the cell (typically by a process that involves the hand of man) and/or is either not found in nature in cells of that type or is found in a different sequence, context and/or in different amounts.

In some embodiments, reprogramming agents are introduced into cells using viral transduction, e.g., retroviral or lentiviral transduction. In particular embodiments the vector used is not subject to methylation-induced silencing. In some embodiments the vector is a non-replicating vector, and in some embodiments the vector is a non-integrating vector. In particular embodiments the vector is an integrating vector which is able to be excised from the cell's genome, e.g., able to be excised such that the cell's genome after excision is substantially similar or identical to the genome of the cell prior to integration of the vector. In some embodiments, reprogramming agents are introduced into cells using protein transduction or transient transfection of a nucleic acid construct that encodes a protein effective either by itself or in combination with other reprogramming agent(s) to reprogram the cells. Optionally cells are subjected to an electric field and/or contacted with an agent that enhances cell permeability to increase uptake of the reprogramming agent. In some embodiments, at least one of Oct4, Sox2, Klf4, Nanog, Lin28 and c-Myc may be exogenously introduced into somatic cells using such methods. In one embodiment Oct4, Sox2 and Klf4 are introduced into the cell(s), while in another embodiment Oct4, Sox2, Klf4 and c-Myc are introduced into the cells(s). In another embodiment Oct4, Sox2, Nanog and Lin28 are introduced into the cell(s).

Genes that affect the pluripotent state of a cell and thus are candidate reprogramming agents include pluripotency genes, genes involved in chromatin remodeling, and genes that are important for maintaining pluripotency, such as LIF, BMP, and PD098059 (Cell, 115: 281-292 (2003); Philos Trans R Soc Lond B Biol Sci. 2003 Aug. 29; 358(1436): 1397-402). Thomson et al. used Oct4, Sox2, Nanog, and Lin28 using a lentiviral system to reprogram adult human cells (Thomson et al., Science 5854: 1224-1225 (Nov. 23, 2007)). Other genes that can affect whether or not a cell is pluripotent include certain oncogenes, such as c-myc. Other genes include telomerase, e.g., the gene encoding the catalytic subunit of telomerase. Yet other genes include Sox1, Sox2, Sox3, Sox 15, Sox18, FoxD3, Stat3, N-Myc, L-Myc, Klf1, Klf2, Klf4 and Klf5. Other genes of interest include those encoding microRNA precursors that have been associated with multipotency or pluripotency and/or that is naturally expressed in multipotent or pluripotent cells. Optionally the gene is downregulated as the cells differentiate and/or is not expressed in adult somatic cells. Other polynucleotides of interest include those encoding RNAi agents such as shRNAs targeted to a gene that is a target of an endogenous microRNA that is naturally expressed in multipotent or pluripotent cells.

In addition, additional factors may be overexpressed or exogenously expressed in the somatic cell to facilitate reprogramming. For example, factors which assist in inducing the cell to assume a less differentiated state may be expressed in the cell. As described herein, C/EBPα has been shown to assist in the reprogramming of mature B cells. Other members of the C/EBPα family, such as human homologs of C/EBPα may be similarly useful.

It will be understood that throughout the embodiments of the invention, encoded polypeptides may be exogenously introduced into a cell instead of or in addition to exogenous introduction of a polynucleotide encoding said polypeptide unless otherwise indicated or implied from context. In addition, it will be understood that reference to a "gene" herein is intended to encompass the coding sequence of the gene with or without the endogenous regulatory elements of the gene and with or without intronic sequence elements unless otherwise indicated or implied from context.

Expression of an exogenously introduced polynucleotide may be carried out in several ways. In one embodiment, the exogenously introduced polynucleotide may be expressed from a chromosomal locus different from the endogenous chromosomal locus of the polynucleotide. Such chromosomal locus may be a locus with open chromatin structure, and contain gene(s) dispensible for a somatic cell. In other words, the desirable chromosomal locus contains gene(s) whose disruption will not cause cells to die. Exemplary chromosomal loci include, for example, the mouse ROSA 26 locus and type II collagen (Col2a1) locus (See Zambrowicz et al., 1997). The exogenously introduced polynucleotide may be expressed from an inducible promoter such that its expression can be regulated as desired.

In an alternative embodiment, the exogenously introduced polynucleotide may be transiently transfected into cells, either individually or as part of a cDNA expression library. In one embodiment the cDNA expression library can be prepared from pluripotent cells, including but not limited to embryonic stem cells, oocytes, blastomeres, inner cell mass cells, embryonic germ cells, embryoid body (embryonic) cells, morula-derived cells, teratoma (teratocarcinoma) cells, and multipotent partially differentiated embryonic stem cells taken from later in the embryonic development process. Candidate reprogramming agents may be identified from such libraries.

The cDNA library is prepared by conventional techniques. Briefly, mRNA is isolated from an organism of interest. An RNA-directed DNA polymerase is employed for first strand synthesis using the mRNA as template. Second strand synthesis is carried out using a DNA-directed DNA polymerase which results in the cDNA product. Following conventional processing to facilitate cloning of the cDNA, the cDNA is inserted into an expression vector such that the cDNA is operably linked to at least one regulatory sequence. The choice of expression vectors for use in connection with the cDNA library is not limited to a particular vector. Any expression vector suitable for use in mouse cells is appropriate. In one embodiment, the promoter which drives expression from the cDNA expression construct is an inducible promoter. The term regulatory sequence includes promoters, enhancers and other expression control elements. Exemplary regulatory sequences are described in Goeddel; Gene Expression Technology: Methods in Enzymology, Academic Press, San Diego, Calif. (1990). For instance, any of a wide variety of expression control sequences that control the expression of a DNA sequence when operatively linked to it may be used in these vectors to express cDNAs. Such useful expression control sequences, include, for example, the early and late promoters of SV40, tet promoter, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

The exogenously introduced polynucleotide may be expressed from an inducible promoter. The term "inducible promoter", as used herein, refers to a promoter that, in the absence of an inducer (such as a chemical and/or biological agent), does not direct expression, or directs low levels of expression of an operably linked gene (including cDNA), and, in response to an inducer, its ability to direct expression is enhanced. Exemplary inducible promoters include, for example, promoters that respond to heavy metals (CRC Boca Raton, Fla. (1991), 167-220; Brinster et al. Nature (1982), 296, 39-42), to thermal shocks, to hormones (Lee at al. P.N.A.S. USA (1988), 85, 1204-1208; (1981), 294, 228-232; Klock et al. Nature (1987), 329, 734-736; Israel and Kaufman, Nucleic Acids Res. (1989), 17, 2589-2604), promoters that respond to chemical agents, such as glucose, lactose, galactose or antibiotic (e.g., tetracycline or doxycycline).

A tetracycline-inducible promoter is an example of an inducible promoter that responds to an antibiotic. See Gossen at al., 2003. The tetracycline-inducible promoter comprises a minimal promoter linked operably to one or more tetracycline operator(s). The presence of tetracycline or one of its analogues leads to the binding of a transcription activator to the tetracycline operator sequences, which activates the minimal promoter and hence the transcription of the associated cDNA. Tetracycline analogue includes any compound that displays structural homologies with tetracycline and is capable of activating a tetracycline-inducible promoter. Exemplary tetracycline analogues includes, for example, doxycycline, chlorotetracycline and anhydrotetracycline. Also of use are tetracycline-repressible promoters.

The aforementioned methods may be used to express any of the exogenously introduced polynucleotides described herein in a somatic cell. For example, they may be used to express a polynucleotide that encodes an RNAi agent targeted to an endogenous DNA methyltransferase or may be used to express a site-specific recombinase.

Applicant discovered that the exogenously introduced factors may be dispensable for maintenance of the pluripotent phenotype. For example, expression of exogenously introduced polynucleotides Oct4, Sox2 and Klf4 are dispensable for maintenance of the pluripotent phenotype. The invention therefore comprises the recognition that reprogrammed somatic cells can be modified after being reprogrammed so as to render one or more introduced factor(s), e.g., polynucleotides, nonfunctional while retaining the ES-like phenotype of the cells.

In certain embodiments of the invention, rendering an introduced polynucleotides nonfunctional reduces potential concerns associated with introducing oncogenes into cells. Thus the invention comprises introducing one or more polynucleotides into a somatic cell, wherein said one or more polynucleotides at least in part reprogram the cell to an ES-like state, identifying a cell that has been reprogrammed to an ES-like state, and functionally inactivating one or more of the introduced polynucleotides. The cells may be maintained in culture for a suitable time period before inactivating the introduced polynucleotide(s). In one embodiment the time period may be selected to be sufficient for the cells to begin displaying a marker or characteristic of pluripotency, to begin expressing an endogenous pluripotency gene, e.g., Oct-4 and/or Nanog, or to begin expressing a downstream target of an endogenous pluripotency gene. In certain embodiments the exogenously introduced polynucleotide is regulated by an inducible regulatory element and functional inactivation is achieved by removal of the inducer of said element.

Functional inactivation is also intended to encompass removal or excision of the introduced polynucleotide. In certain embodiments at least a portion of the one or more introduced polynucleotides is flanked by sites for a site-specific recombinase. The introduced polynucleotide can be functionally inactivated by expressing the recombinase in the cell or introducing the recombinase into the cell. The resulting reprogrammed somatic cell may lack any exogenously introduced coding sequences and/or regulatory elements. The cell may be identical to a non-engineered somatic cell except that it contains one or more sites that remain following recombination.

Markers of Pluripotency

Somatic cells which have been treated with one or more reprogramming agents are maintained in culture for a period of time sufficient to begin reprogramming of the cell. Populations of treated cells may be analyzed in a variety of ways to identify the occurrence or non-occurrence of reprogramming. That is, a population of treated cells can be further treated or analyzed to select for or enrich for cells which have begun the reprogramming process or to select against or decrease cells which have not begun the reprogramming process. Populations of treated somatic cells can be assessed to identify cells which do or do not display one or more markers or characteristics of reprogrammed, e.g., pluripotent, cells. For example, said cell populations can be assessed to identify phenotypic, functional or genetic markers of reprogramming, including expression of one or more pluripotency genes and expression of one or more genes whose expression is activated directly or indirectly as a result of expression of the pluripotency gene. By way of non-limiting example, a population of cells can be assessed to identify expression of alkaline phosphatase, expression of SSEA1, expression of SSEA3, expression of SSEA4, expression of TRAF-60, expression of Nanog, expression of Oct4, expression of Fxb15, morphology characteristic of an ES cell or an ES cell colony, ability to participate in formation of chimeras that survive to term, ability to differentiate into cells having characteristics of endoderm, mesoderm and ectoderm when injected into SCID mice, presence of two active X chromosomes, resistance to DNA methylation, and combinations thereof. A population of cells can also be assessed to identify the absence of any of the markers of reprogramming to identify cells which have not undergone reprogramming.

The term "pluripotency gene", as used herein, refers to a gene that is associated with pluripotency. The expression of a pluripotency gene is typically restricted to pluripotent cells, e.g., pluripotent stem cells, and is crucial for the functional identity of pluripotent cells. It will be appreciated that the protein encoded by a pluripotency gene may be present as a maternal factor in the oocyte, and the gene may be expressed by at least some cells of the embryo, e.g., throughout at least a portion of the preimplantation period and/or in germ cell precursors of the adult.

In some embodiments the pluripotency gene is one whose average expression level in ES cells of a mammal is at least 5, 10, 20, 50, or 100-fold greater than its average per cell expression level in somatic cell types present in the body of an adult mammal of that type (e.g., mouse, human, farm animal). In some embodiments the pluripotency gene is one whose average expression level in ES cells is at least 5, 10, 20, 50, or 100-fold greater than its average expression level in those terminally differentiated cell types present in the body of an adult mammal (e.g., mouse, human, farm animal). In some embodiments the pluripotency gene is one that is essential to maintain the viability or pluripotent state of ES cells derived using conventional methods. Thus if the gene is knocked out or inhibited (i.e., eliminated or reduced), the ES cells die or, in some embodiments, differentiate. In some embodiments the pluripotency gene is characterized in that inhibiting its expression in an ES cell (resulting in, e.g., a reduction in the average steady state level of RNA transcript and/or protein encoded by the gene by at least 20%, 30%, 40%, 50%, 60%, 70%, 80%, 90%, 95%, or more) results in a cell that is viable but no longer pluripotent. In some embodiments the pluripotency gene is characterized in that its expression in an ES cell decreases (resulting in, e.g., a reduction in the average steady state level of RNA transcript and/or protein encoded by the gene by at least 50%, 60%, 70%, 80%, 90%, 95%, or more) when the cell differentiates into a terminally differentiated cell.

The transcription factor Oct-4 (also called Pou5fl, Oct-3, Oct3/4) is an example of a pluripotency gene. Oct-4 has been shown to be required for establishing and maintaining the undifferentiated phenotype of ES cells and plays a major role in determining early events in embryogenesis and cellular differentiation (Nichols et al., 1998, Cell 95:379-391; Niwa et al., 2000, Nature Genet. 24:372-376). Oct-4 is down-regulated as stem cells differentiate into specialised cells.

Nanog is another example of a pluripotency gene. Nanog is a divergent homeodomain protein that directs propagation of undifferentiated ES cells. Nanog mRNA is present in pluripotent mouse and human cell lines, and absent from differentiated cells. In pre-implantation embryos, Nanog is restricted to founder cells from which ES cells can be derived. Endogenous Nanog acts in parallel with cytokine stimulation of Stat3 to drive ES cell self-renewal. Elevated Nanog expression from transgene constructs is sufficient for clonal expansion of ES cells, bypassing Stat3 and maintaining Oct4 levels. (See Chambers et al., 2003, Cell 113:

643-655; Mitsui et al., Cell. 2003, 113(5):631-42). Other exemplary pluripotency genes include Sox2 and Stella (see Imamura et al., BMC Developmental Biology 2006, 6:34, Bortvin et al. Development. 2003, 130(8):1673-80; Saitou et al., Nature. 2002, 418 (6895):293-300).

In certain embodiments of the invention the endogenous pluripotency gene is co-expressed with a selectable marker. For example, the endogenous pluripotency gene can be linked to a polynucleotide (e.g., DNA) encoding a selectable marker in such a manner that the selectable marker and the endogenous pluripotency gene are co-expressed. As used herein co-expression is intended to mean that expression of the selectable marker substantially matches the expression of the endogenous pluripotency gene. In one embodiment, the differentiated somatic cells of the present invention comprise a first endogenous pluripotency gene linked to DNA encoding a first selectable marker in such a manner that the expression of the first selectable marker substantially matches the expression of the first endogenous pluripotency gene. The differentiated somatic cells may also be engineered to comprise any number of endogenous pluripotency genes respectively linked to a distinct selectable marker. Thus, in another embodiment, the differentiated somatic cells of the present invention comprise two endogenous pluripotency genes, each of which is linked to DNA encoding a distinct selectable marker. In a further embodiment, the differentiated somatic cells of the present invention comprise three endogenous pluripotency genes, each of which is linked to DNA encoding a distinct selectable marker. The differentiated somatic cells may be further engineered to have one or more pluripotency gene(s) expressed as a transgene under an inducible promoter.

In one embodiment, somatic cells used in the methods comprise only one endogenous pluripotency gene linked to a first selectable marker, and the selection step is carried out to select for the expression of the first selectable marker. In an alternative embodiment, the somatic cells used in the methods comprise any number of endogenous pluripotency genes, each of which is linked to a distinct selectable marker respectively, and the selection step is carried out to select for at least a subset of the selectable markers. For example, the selection step may be carried out to select for all the selectable markers linked to the various endogenous pluripotency genes.

In one embodiment, somatic cells used in the method comprise a selectable marker linked to an endogenous pluripotency gene and an additional pluripotency gene expressed as a transgene under an inducible promoter. For these cells, the method of reprogramming may comprise inducing the expression of the pluripotency transgene and select for the expression of the selectable marker. The method may further comprise contacting the somatic cells with an agent that alters chromatin structure.

For purposes of the present invention, it is not necessary that the expression level of the endogenous pluripotency gene and the selectable marker is the same or even similar. It is only necessary that the cells in which an endogenous pluripotency gene is activated will also express the selectable marker at a level sufficient to confer a selectable phenotype on the reprogrammed cells. For example, when the selectable marker is a marker that confers resistance to a lethal drug (a "drug resistance marker"), the cells are engineered in a way that allows cells in which an endogeneous pluripotency gene is activated to also express the drug resistance marker at a sufficient level to confer on reprogrammed cells resistance to lethal drugs. Thus, reprogrammed cells will survive and proliferate whereas non-reprogrammed cells will die.

In certain embodiments of the invention the selectable marker is operably linked to expression control elements that regulate transcription from the endogenous pluripotency gene. The DNA encoding a selectable marker may be inserted downstream from the end of the open reading frame (ORF) encoding the desired endogenous pluripotency gene, anywhere between the last nucleotide of the ORF and the first nucleotide of the polyadenylation site. An internal ribosome entry site (IRES) may be placed in front of the DNA encoding the selectable marker. Alternatively, the DNA encoding a selectable marker may be inserted anywhere within the ORF of the desired endogenous pluripotency gene, downstream of the promoter, with a termination signal. An internal ribosome entry site (IRES) may be placed in front of the DNA encoding the selectable marker. In further embodiments the DNA encoding the selectable marker may be inserted anywhere within a gene whose expression is activated directly or indirectly as a result of expression of the pluripotency gene. In some embodiments the DNA encoding a selectable marker is inserted into an intron. In some embodiments, the endogenous pluripotency gene into which the DNA has been inserted expresses a functional pluripotency gene product while in other embodiments it does not. The selectable marker may be inserted into only one allele, or both alleles, of the endogenous pluripotency gene. In certain other embodiments an exogenous polynucleotide including a selectable marker operably linked to expression control elements that regulate transcription from the endogenous pluripotency gene is inserted into the cellular genome at a location external to the locus of an endogenous pluripotency gene such that conditions appropriate to activate expression of the endogenous pluripotency gene also activate expression of the exogenous polynucleotide.

A selectable marker, as used herein, is a marker that, when expressed, confers upon recipient cells a selectable phenotype, such as antibiotic resistance, resistance to a cytotoxic agent, nutritional prototrophy, or expression of a surface protein. Other proteins whose expression can be readily detected such as a fluorescent or luminescent protein or an enzyme that acts on a substrate to produce a colored, fluorescent, or luminescent substance are also of use as selectable markers. The presence of a selectable marker linked to an endogenous pluripotency gene makes it possible to identify and select reprogrammed cells in which the endogenous pluripotency gene is expressed. A variety of selectable marker genes can be used, such as neomycin resistance gene (neo), puromycin resistance gene (puro), guanine phosphoribosyl transferase (gpt), dihydrofolate reductase (DHFR), adenosine deaminase (ada), puromycin-N-acetyltransferase (PAC), hygromycin resistance gene (hyg), multidrug resistance gene (mdr), thymidine kinase (TK), hypoxanthine-guanine phosphoribosyltransferase (HPRT), and hisD gene. Other markers include green fluorescent protein (GFP) blue, sapphire, yellow, red, orange, and cyan fluorescent proteins and variants of any of these. Luminescent proteins such as luciferase (e.g., firefly or *Renilla* luciferase) are also of use. Systems based on enzyme reporters such as beta-galactosidase, alkaline phosphatase, chloramphenicol acetyltransferase, etc., are also of use. In some embodiments the marker is a secreted enzyme. As will be evident to one of skill in the art, the term "selectable marker" as used herein can refer to a gene or to an expression product of the gene, e.g., an encoded protein.

In some embodiments the selectable marker confers a proliferation and/or survival advantage on cells that express it relative to cells that do not express it or that express it at significantly lower levels. Such proliferation and/or survival advantage typically occurs when the cells are maintained under certain conditions, i.e., "selective conditions". To ensure an effective selection, a population of cells can be maintained for a under conditions and for a sufficient period of time such that cells that do not express the marker do not proliferate and/or do not survive and are eliminated from the population or their number is reduced to only a very small fraction of the population. The process of selecting cells that express a marker that confers a proliferation and/or survival advantage by maintaining a population of cells under selective conditions so as to largely or completely eliminate cells that do not express the marker is referred to herein as "positive selection", and the marker is said to be "useful for positive selection". Markers useful for positive selection are of particular interest in embodiments of the invention in which an endogenous pluripotency gene is linked to a selectable marker.

Negative selection and markers useful for negative selection are also of interest in certain of the methods described herein. Expression of such markers confers a proliferation and/or survival disadvantage on cells that express the marker relative to cells that do not express the marker or express it at significantly lower levels (or, considered another way, cells that do not express the marker have a proliferation and/or survival advantage relative to cells that express the marker). Cells that express the marker can therefore be largely or completely eliminated from a population of cells when maintained in selective conditions for a sufficient period of time.

Certain markers of interest herein are useful for positive and negative selection depending on the particular selective conditions employed. Thus under certain sets of conditions cells that express the marker have a proliferation and/or survival advantage relative to cells that do not express the marker while under other sets of conditions cells that express the marker have a proliferation and/or survival disadvantage relative to cells that do not express the marker. Two examples of such markers that are suitable for use in the invention are hypoxanthine phosphoribosyl transferase (HPRT), an enzyme that catalyzes certain reactions in which purine-type compounds are synthesized and/or interconverted, and thymidine kinase (TK), which catalyzes certain reactions in which pyrimidine-type compounds are synthesized and/or interconverted. Under typical culture conditions DNA synthesis in mammalian cells proceeds through a main (de novo) pathway in which glutamine and aspartate are used as initial substrates for a series of reactions leading to synthesis of purine-type (e.g., dATP and dGTP) and pyrimidine-type (e.g., dCTP and dTTP) nucleotides. When the de novo pathway is blocked, mammalian cells must utilize alternative pathways to synthesize the needed nucleotides. The purine salvage pathway involves converting hypoxanthine to IMP, a reaction catalyzed by HPRT. The second pathway converts thymidine to dTMP, a reaction catalyzed by TK. Thus cells lacking HPRT expression (e.g., cells lacking a functional copy of the HPRT gene) or lacking TK expression (e.g., cells lacking a functional copy of the TK gene) can grow in standard culture medium but die in HAT medium, which contains aminopterin, hypoxanthine, and thymidine. In cells lacking HPRT endogenous expression, HPRT can be used as selectable marker whose expression may be selected for in HAT medium. Similarly, in cells lacking endogenous TK expression, TK can be used as a selectable marker whose expression may be selected for in HAT medium.

In addition to the ability to select for cells that express HPRT or TK, it is also possible to select for cells that lack expression of functional HPRT and/or TK, e.g., cells that do not express one or both of these enzymes. HPRT converts certain otherwise non-toxic compounds including a variety of purine analogs such as 8-azaguanine (8-AZ) and 6-thioguanine (6-TG) into cytotoxic compounds. TK converts certain pyrimidine analogs such as 5-bromodeoxyuridine and trifluoro-methyl-thymidine into cytotoxic compounds. The cytotoxic compounds may have deleterious effects on cells e.g., by inhibiting enzymes involved in nucleic acid synthesis and/or becoming incorporated into DNA, leading to mismatches and mutations. Thus in culture medium containing 8-AZ, 6-TG, etc., cells that express HPRT are at a growth disadvantage relative to cells that do not express HPRT or that express it at lower levels insufficient to fully support nucleic acid synthesis, It is therefore possible to use these selective conditions to select for cells that lack HPRT activity. Similarly, in medium containing bromodeoxyuridine or trifluoro-methyl-thymidine, cells that express TK are at a growth disadvantage relative to cells that lack TK expression or express a lower and insufficient level of TK. It is therefore possible to use these selective conditions to select for cells that lack TK activity.

In some embodiments of the invention, a population of differentiated somatic cells which have been treated with one or more reprogramming agents or factors and then maintained for a suitable period of time are assayed to identify cells which display a marker of pluripotency.

As described herein, differentiated somatic cells for use in the invention may the engineered differentiated somatic cells can be obtained from a transgenic mouse comprising such engineered somatic cells. Such transgenic mouse can be produced using standard techniques known in the art. For example, Bronson et al. describe a technique for inserting a single copy of a transgene into a chosen chromosomal site. See Bronson et al., 1996. Briefly, a vector containing the desired integration construct (for example, a construct containing a selectable marker linked to a pluripotency gene) is introduced into ES cells by standard techniques known in the art. The resulting ES cells are screened for the desired integration event, in which the knock-in vector is integrated into the desired endogenous pluripotency gene locus such that the selectable marker is integrated into the genomic locus of the pluripotency gene and is under the control of the pluripotency gene promoter. The desired ES cell is then used to produce a transgenic mouse in which all cell types contain the correct integration event. Desired types of cells may be selectively obtained from the transgenic mouse and maintained in vitro. In one embodiment, two or more transgenic mice may be created, each carrying a distinct integration construct. These mice may then be bred to generate mice that carry multiple desired integration constructs. For example, one type of transgenic mouse may be created to carry an endogenous pluripotency gene linked to a selectable marker, while a second type of transgenic mouse may be created to carry a pluripotency gene expressed as a transgene under an inducible promoter. These two types of mice may then be bred to generate transgenic mice that have both a selectable marker linked to an endogenous pluripotency gene and an additional pluripotency gene expressed as a transgene under an inducible promoter. These two pluripotency genes may or may not be the same. Many variables are contemplated: the identity of the endogenous pluripotency gene linked to marker, the identity of the pluripotency gene expressed as a transgene, and the number of the endogenous pluripotency gene linked to a selectable marker, and the number of pluripotency gene expressed as a transgene. The present invention encompasses all possible combinations of these variables. In other embodiments one of the mice carries an endogenous pluripotency gene linked to a selectable marker and one of the mice carries a DNA that encodes an RNAi agent targeted to a DNMT gene (thereby capable of inhibiting the expression of the DNMT gene) as discussed further below.

Alternatively, engineered differentiated somatic cells of the present invention may be produced by direct introduction of the desired construct into somatic cells. A DNA construct may be introduced into cells by any standard technique known in the art, such as viral transfection (e.g., using an adenoviral system) or liposome-mediated transfection. Any means known in the art to generate somatic cells with targeted integration can be used to produce somatic cells of the invention, e.g., cells in which a selectable marker is operably linked to an endogenous pluripotency gene or cells in which an endogenous gene is rendered conditional by introducing a conditional promoter or sites for a site-specific recombinase into or near the gene.

In mammalian cells, homologous recombination occurs at much lower frequency compared to non-homologous recombination. To facilitate the selection of homologous recombination events over the non-homologous recombination events, at least two enrichment methods have been developed: the positive-negative selection (PNS) method and the "promoterless" selection method (Sedivy and Dutriaux, 1999). Briefly, PNS, the first method, is in genetic terms a negative selection: it selects against recombination at the incorrect (non-homologous) loci by relying on the use of a negatively selectable gene that is placed on the flanks of a targeting vector. On the other hand, the second method, the "promoterless" selection, is a positive selection in genetic terms: it selects for recombination at the correct (homologous) locus by relying on the use of a positively selectable gene whose expression is made conditional on recombination at the homologous target site. The disclosure of Sedivy and Dutriaux is incorporated herein.

As described herein, differentiated somatic cells which have been contacted with at least one reprogramming agent are assessed to distinguish cells which have been reprogrammed to multipotency or pluripotency from cells which have not. This may be done by distinguishing cells which demonstrate one or more pluripotency characteristics or display one or more markers of pluripotency from cells which do not.

The term "pluripotency characteristics", as used herein, refers to many characteristics associated with pluripotency, including, for example, the ability to differentiate into all types of cells and an expression pattern distinct for a pluripotent cell, including expression of pluripotency genes, expression of other ES cell markers, and on a global level, a distinct expression profile known as "stem cell molecular signature" or "stemness."

Thus, to assess reprogrammed somatic cells for pluripotency characteristics, one may analyze such cells for different growth characteristics and ES cell-like morphology. Cells may be injected subcutaneously into immunocompromised SCID mice to induce teratomas (a standard assay for ES cells). ES-like cells can be differentiated into embryoid bodies (another ES specific feature). Moreover, ES-like cells can be differentiated in vitro by adding certain growth factors known to drive differentiation into specific cell types.

Self-renewing capacity, marked by induction of telomerase activity, is another plutipotency characteristic that can be monitored. One may carry out functional assays of the reprogrammed somatic cells by introducing them into blastocysts and determine whether the cells are capable of giving rise to all cell types. See Hogan et al., 2003. If the reprogrammed cells are capable of forming a few cell types of the body, they are multipotent; if the reprogrammed cells are capable of forming all cell types of the body including germ cells, they are pluripotent.

One may also examine the expression of an individual pluripotency gene in the reprogrammed somatic cells to assess their pluripotency characteristics. Additionally, one may assess the expression of other ES cell markers. Stage-specific embryonic 1 5 antigens-1, -3, and -4 (SSEA-1, SSEA-3, SSEA-4) are glycoproteins specifically expressed in early embryonic development and are markers for ES cells (Solter and Knowles, 1978, Proc. Natl. Acad. Sci. USA 75:5565-5569; Kannagi et al., 1983, EMBO J 2:2355-2361). Elevated expression of the enzyme Alkaline Phosphatase (AP) is another marker associated with undifferentiated embryonic stem cells (Wobus et al., 1984, Exp. Cell 152: 212-219; Pease et al., 1990, Dev. Biol. 141:322-352). Other stem/progenitor cells markers include the intermediate neurofilament nestin (Lendahl et al., 1990, Cell 60:585-595; Dah-Istrand et al., 1992, J. Cell Sci. 103:589-597), the membrane glycoprotein prominin/AC133 (Weigmann et al., 1997, Proc. Natl. Acad. USA 94:12425-12430; Corbeil et al., 1998, Blood 91:2625-22626), the transcription factor Tcf-4 (Korinek et al, 1998, Nat. Genet. 19: 379-383; Lee et al., 1999, J. Biol. Chem. 274.1 566-1 572), and the transcription factor Cdx1 (Duprey et al., 1988, Genes Dev. 2:1647-1654; Subramania'n et al., 1998, Differentiation 64:11-18). Additional ES cell markers are described in Ginis, I., et al., Dev. Biol., 269: 369-380, 2004. For example, REX-1, TEAT, UTF-1, TRF-1, TRF-2, connexin43, connexin45, FGFR-4, ABCG-2, and Glut-1 are of use.

One may additionally conduct expression profiling analyses of the reprogrammed somatic cells to assess their pluripotency characteristics. Pluripotent cells, such as embryonic stem cells, and multipotent cells, such as adult stem cells, are known to have a distinct pattern of global gene expression profile. This distinct pattern is termed "stem cell molecular signature", or "stemness". See, for example, Ramalho-Santos et al., Science 298: 597-600 (2002); Ivanova et al., Science 298: 601-604. One may assess the epigenetic state of cellular DNA. One may assess the resistance of the cells to global DNA demethylation. One may assess the developmental potential of the cells. In some embodiments, cells that are able to form teratomas containing cells having characteristics of endoderm, mesoderm, and ectoderm when injected into SCID mice and/or possess ability to participate (following injection into murine blastocysts) in formation of chimeras that survive to term are considered pluripotent.

Engineered Somatic Cells and Transgenic Mice Comprising Such Cells

The present invention further provides engineered somatic cells in which DNA methylation can be regulated. "DNA methylation" is used herein consistently with it use in the art to refer to the modification of eukaryotic DNA by attachment of a methyl group to a cytosine. As known in the art, cytosine methylation of DNA plays important roles in epigenetic gene regulation and the maintenance of genomic integrity. Mammalian cells possess several different DNA methyltransferases that are responsible for transfer of a methyl group to cytosine present in DNA (Goll, G, and Bestor, T., Annu Rev. Biochemistry, 74: 481-514, 2005). As least three genes are involved in establishing and maintaining genomic methylation in mammalian cells, i.e., those encoding the de novo methyltransferases DNMT3a and DNMT3b and the maintenance enzyme DNMT1 which methylates hemimethylated DNA but also exhibits the ability to methylate unmethylated DNA. Mutational analysis in mice has demonstrated that these three genes are essential, with lethality occurring soon after gastrulation in Dnmt1-null embryos and at later time points in the case of embryos lacking functional Dnmt3a or Dnmt3b genes (Li, 1992; Okano, at al., Cell, 99(3):247-57, 1999). Aberrant regulation of a number of genes has been observed in these embryos. The data are consistent with a requirement for DNA methylation for the transcriptional silencing that occurs in many cell types during mammalian development and is likely necessary for the proper cell differentiation.

The invention provides cells in which expression of an endogenous DNA methyltransferase (DNMT) gene such as Dnmt1, Dnmt3a, or Dnmt3b can be regulated and/or in which expression of an endogenous Dnmt gene is altered relative to nonengineered somatic cells. In certain embodiments the somatic cells contain an exogenously introduced gene that encodes an RNA that interferes with expression of an endogenous DNA methyltransferase (DNMT) gene such as Dnmt1, Dnmt3a, or Dnmt3b. In some embodiments the RNA interferes with expression of an endogenous DNA methyltransferase gene by RNA interference (RNAi). "RNAi" is used herein consistently with its meaning in the art to refer to a phenomenon whereby double-stranded RNA (dsRNA) triggers the sequence-specific degradation or translational repression of a corresponding mRNA having complementarity to one strand of the dsRNA. It will be appreciated that the complementarity between the strand of the dsRNA and the mRNA need not be 100% but need only be sufficient to mediate inhibition of gene expression (also referred to as "silencing" or "knockdown"). For example, the degree of complementarity is such that the strand can either (i) guide cleavage of the mRNA in a protein complex called the RNA-induced silencing complex (RISC); or (ii) cause translational repression of the mRNA. In certain embodiments the double-stranded portion of the RNA is less than about 30 nucleotides in length, e.g., between 17 and 29 nucleotides in length. In mammalian cells, RNAi may be achieved by introducing an appropriate double-stranded nucleic acid into the cells or expressing a nucleic acid in cells that is then processed intracellularly to yield dsRNA therein.

For purposes of the present invention an at least partly double-stranded RNA that is capable of triggering sequence-specific inhibition of gene expression, optionally after undergoing intracellular processing, is referred to as an "RNAi agent". Exemplary nucleic acids capable of mediating RNAi are a short hairpin RNA (shRNA), a short interfering RNA (siRNA), and a microRNA precursor. These terms are well known and are used herein consistently with their meaning in the art. siRNAs typically comprise two separate nucleic acid strands that are hybridized to each other to form a duplex. They can be synthesized in vitro, e.g., using standard nucleic acid synthesis techniques. They can comprise a wide variety of modified nucleosides, nucleoside analogs and can comprise chemically or biologically modified bases, modified backbones, etc. Any modification recognized in the art as being useful for RNAi can be used. Some modifications result in increased stability, cell uptake, potency, etc. In certain embodiments the siRNA comprises a duplex about 19 nucleotides in length and one or two 3' overhangs of 1-5 nucleotides in length, which may be composed of deoxyribonucleotides. shRNA comprise a single nucleic acid strand that contains two complementary portions separated by a predominantly non-selfcomplementary region. The complementary portions hybridize to form a duplex structure and the non-selfcomplementary region forms a loop connecting the 3' end of one strand of the duplex and the 5' end of the other strand. shRNAs undergo intracellular processing to generate siRNAs.

MicroRNAs (miRNAs) are small, non-coding, single-stranded RNAs of about 21-25 nucleotides (in mammalian systems) that inhibit gene expression in a sequence-specific manner. They are generated intracellularly from precursors having a characteristic secondary structure comprised of a short hairpin (about 70 nucleotides in length) containing a duplex that often includes one or more regions of imperfect complementarity. Naturally occurring miRNAs are only partially complementary to their target mRNA and typically act via translational repression. As used herein the term "shRNA" encompasses RNAi agents modelled on endogenous microRNA precursors. In some embodiments, a sequence encoding the stem portion of a stem-loop structure or encoding a complete stem-loop can be inserted into a nucleic acid comprising at least a portion of an endogenous microRNA primary transcript, e.g., in place of the sequence that encodes the endogenous microRNA or minimum (~70 nucleotide) microRNA hairpin.

One of skill in the art will be able to identify an appropriate RNAi agent to inhibit expression of a gene. Such an RNAi agent is referred to as being "targeted to" the gene and the encoded mRNA. The RNAi agent may inhibit expression sufficiently to reduce the average steady state level of the RNA transcribed from the gene (e.g., mRNA) or its encoded protein by, e.g., by at least 50%, 60%, 70%, 80%, 90%, 95%, or more). The RNAi agent may contain a sequence between 17-29 nucleotides long, e.g., 19-23 nucleotides long that is 100% complementary to the mRNA or contains up to 1, 2, 3, 4, or 5 nucleotides, or up to about 10-30% nucleotides, that do not participate in Watson-Crick base pairs when aligned with the mRNA to achieve the maximum number of complementary base pairs. The RNAi agent may contain a duplex between 17-29 nucleotides long in which all nucleotides participate in Watson-Crick base pairs or in which up to about 10-30% of the nucleotides do not participate in a Watson-Crick base pair. One of skill in the art will be aware of which sequence characteristics are often associated with superior siRNA functionality and algorithms and rules by which such siRNAs can be designed (see, e.g., Jagla, B., et al, RNA, 11(6):864-72, 2005). The methods of the invention can employ siRNAs having such characteristics, although the range of useful sequences is not limited to those that satisfy these rules. In some embodiments the sequence of either or both strands of the RNAi agent is/are chosen to avoid silencing non-target genes, e.g., the strand(s) may have less than 70%, 80%, or 90% complementarity to any mRNA other than the target mRNA. In some embodiments multiple different sequences are used. The tables below list the Gene IDs of the human and mouse genes encoding DNMT1, 3a, and 3b and antisense sequences of exemplary siRNAs for silencing these genes. Similar information is included also for HPRT. One of skill in the art can readily find the Gene ID, accession numbers, and sequence information for any gene of interest in publicly available databases. One of skill in the art can readily design siRNAs and shRNAs to silence these genes or others. It will be appreciated that the sequences may be varied and/or extended by incorporating additional nucleotides at either or both ends. Furthermore, if multiple isoforms exist, one can design siRNAs or shRNAs targeted against a region present in all of the isoforms expressed in a given cell type or organism of interest.

TABLE A siRNA sequences targeting Human genes

| Gene | Gene ID | siRNA sequences |
|---|---|---|
| Dnmt1 | 1786 | GGAAGAAGAGUUACUAUAA (SEQ. ID. NO: 11) |
|  |  | GAGCGGAGGUGUCCCAAUA (SEQ. ID. NO: 12) |
|  |  | GGACGACCCUGACCUCAAA (SEQ. ID. NO: 13) |
|  |  | GAACGGUGCUCAUGCUUAC (SEQ. ID. NO: 14) |
|  |  | UUUCUCCCUCAGACACUC (SEQ ID NO: 15) |
| Dnmt3a | 1788 | GCACAAGGGUACCUACGGG (SEQ. ID. NO: 16) |
|  |  | CAAGAGAGCGGCUGGUGUA (SEQ. ID. NO: 17) |
|  |  | GCACUGAAAUGGAAAGGGU (SEQ. ID. NO: 18) |
|  |  | GAACUGCUUUCUGGAGUGU (SEQ. ID. NO: 19) |
| Dnmt3b | 1789 | GAAAGUACGUCGCUUCUGA (SEQ. ID. NO: 20) |
|  |  | ACAAAUGGCUUCAGAUGUU (SEQ. ID. NO: 21) |
|  |  | GCUCUUACCUUACCAUCGA (SEQ. ID. NO: 22) |
|  |  | UUUACCACCUGCUGAAUUA (SEQ. ID. NO: 23) |
| Hprt | 3251 | CCAGUUUCACUAAUGACACAA (SEQ ID NO: 24) |

TABLE B siRNA Targeting Mouse genes

| Gene | Gene ID | siRNA sequences |
|---|---|---|
| Dnmt1 | 13433 | GGAAAGAGAUGGCUUAACA (SEQ. ID. NO: 25) |
|  |  | GCUGGGAGAUGGCGUCAUA (SEQ. ID. NO: 26) |
|  |  | GAUAAGAAACGCAGAGUUG (SEQ. ID. NO: 27) |
|  |  | GGUAGAGAGUUACGACGAA (SEQ. ID. NO: 28) |
| Dnmt3a | 13435 | CGCGAUUUCUUGAGUCUAA (SEQ. ID. NO: 29) |
|  |  | CGAAUUGUGUCUUGGUGGA (SEQ. ID. NO: 30) |
|  |  | AAACAUCGAGGACAUUUGU (SEQ. ID. NO: 31) |
|  |  | CAAGGGACUUUAUGAGGGU (SEQ. ID. NO: 32) |
| Dnmt3b | 13436 | GCAAUGAUCUCUCUAACGU (SEQ. ID. NO: 33) |
|  |  | GGAAUGCGCUGGGUACAGU (SEQ. ID. NO: 34) |
|  |  | UAAUCUGGCUACCUUCAAU (SEQ. ID. NO: 35) |
|  |  | GCAAAGGUUUAUAUGAGGG (SEQ. ID. NO: 36) |
| Plort | 15452 | CCAGUUUCACUAAUGACACAA (SEQ ID NO: 37) |

To express an RNAi agent in somatic cells, a nucleic acid construct comprising a sequence that encodes the RNAi agent, operably linked to suitable expression control elements, e.g., a promoter, can be introduced into the cells as known in the art. For purposes of the present invention a nucleic acid construct that comprises a sequence that encodes an RNA or polypeptide of interest, the sequence being operably linked to expression control elements such as a promoter that direct transcription in a cell of interest, is referred to as an "expression cassette". The promoter can be an RNA polymerase I, II, or III promoter functional in mammalian cells. In certain embodiments the promoter is one that is functional when introduced into somatic cells. In certain embodiments expression of the RNAi agent is conditional. In some embodiments expression is regulated by placing the sequence that encodes the RNAi agent under control of a regulatable (e.g., inducible or repressible) promoter.

In some embodiments regulation of expression of a DNA methyltransferase is dependent on a site-specific recombinase. Site-specific recombinases and methods of use thereof for achieving controlled and reversible expression of genes are known in the art. Such recombinases are proteins that recognize specific nucleic acid sequences and mediate insertion into or excision of sequences located between these sites. Recombinase systems include the Cre-Lox and Flp-Frt systems, among others. In some embodiments at least a portion of the coding sequence for the RNAi agent is positioned between sites for the recombinase. Expression of the recombinase (e.g., Cre) in the cell or its exogenous introduction into a cell causes excision of the portion of the coding sequence located between the sites, permanently turning off expression of the gene. In some embodiments expression of a gene in a cell is prevented due to presence of a "stopper" sequence located between a promoter element and the transcription start site or between different portions of a promoter element (e.g., between a TATA box and a second portion of a promoter element). The stopper sequence is flanked by sites for a recombinase, which sites are also located between the promoter and the transcription start site or between different portions of a promoter element. Expression or introduction of the recombinase into the cell causes excision of the stopper sequence, thereby bringing the promoter into operable association with the transcription start site or reconstituting a functional promoter, thereby allowing transcription to proceed. In some embodiments, the cells comprise an expression cassette in which expression of the recombinase is under control of inducible expression control elements such as an inducible promoter. Expression of the recombinase is induced, e.g., by administering an appropriate inducing agent such as a small molecule (e.g., tetracycline or an analog thereof, a hormone such as estrogen or a glucocorticoid, a metal, etc.) to cells or to an organism or by introducing an expression vector that encodes the recombinase into the cell or organism. See, e.g., U.S. Pat. No. 6,995,011 and Ventura, at al. (reference 13 of reference set 2). In one embodiment the promoter is a U6 promoter, and a Lox-Stop-Lox sequence is inserted between the proximal sequence element (PSE) and the TATA box or between the TATA box and the transcription start site. In some embodiments the TATA box in a promoter (e.g., the U6 promoter) is replaced by a bifunctional lox site (TATAlox) that retains the ability to undergo Cre-mediated recombination and contains a functional TATA box is used, so that after recombination the spacing between the PSE, TATA, and transcriptional start site is not altered (Ventura, et. Al, 2004).

In some embodiments the invention provides a cell that comprises a first copy of a Dnmt gene that is functional but can be rendered nonfunctional by expressing in or introducing a first recombinase into the cell and a second copy of the Dnmt gene that is nonfunctional but can be rendered functional by expressing in or introducing a second recombinase into the cell. The first copy of the gene or an essential portion thereof may, for example, be flanked by sites for the first recombinase so that when the first recombinase is present the gene or a portion thereof is excised and the gene is rendered nonfunctional. The second copy of the gene may, for example, comprise a stopper sequence located between sites for the second recombinase. The stopper sequence prevents synthesis of a functional DNMT protein. For example, the stopper may be present between the promoter and the transcriptional start site and prevent transcription or it may result in an insertion into the DNMT protein that renders the protein non-functional. When the second recombinase is present the stopper sequence is excised, and a functional DNMT is produced. In some embodiments, a gene is considered "nonfunctional" if it is not detectably transcribed or, if transcribed, the level of transcription is reduced by at least 100-fold. In some embodiments, a "nonfunctional" gene encodes a DNMT protein that lacks at least 90% of its catalytic domain and/or at least 90% of its localization domain. One of skill in the art will be able to generate non-functional Dnmt1, 3a, and/or 3b genes. Genes can be tested to determine whether they encode a functional protein using standard in vitro assays or by determining whether the gene is able to rescue the lethality of a Dnmt1, 3a, or 3b knockout. In some embodiments, a "nonfunctional gene" encodes a protein whose DNA methylating activity in vitro against a suitable substrate (e.g., hemimethylated DNA in the case of DNMT1) using a standard assay known in the art is reduced by at least 95%, 98%, 99% or more. In some embodiments a non-functional gene is one that, when present as the sole source of DNMT protein in a somatic cell of interest such as a primary mammalian fibroblast, does not encode a protein capable of allowing the cell to survive for a period of 10 days in standard culture conditions. DNA methylation can be regulated in the cell as follows. First, DNA methylation is inhibited by introduction or expression of the first recombinase, thereby eliminating expression of functional DNMT1. The cells are maintained in culture. In the absence of a functional DNMT1, DNA demethylation occurs over time (either spontaneously or as a result of active demethylation) and hemimethylated DNA is not remethylated after cell division. When it is desired to restore DNA methylation, the second recombinase is introduced or expressed in cells, causing removal of the stopper sequence and allowing production of functional DNMT1. In some embodiments this approach is applied to render expression of DNMT1, 3a, 3b, or any combination thereof conditional.

In some embodiments the recombinase is expressed transiently, e.g., it becomes undetectable after about 1-2 days, 2-7 days, 1-2 weeks, etc. Transient expression can be achieved by transient transfection or by expression from a regulatable promoter.

In some embodiments the recombinase is introduced from external sources. Optionally the recombinase in these embodiments comprises an amino acid sequence (also referred to as a "protein transduction domain") that enhances cellular uptake of polypeptides. Such uptake-enhancing amino acid sequences are found, e.g., in HIV-1 TAT protein, the herpes simplex virus 1 (HSV-1) DNA-binding protein VP22, the *Drosophila Antennapedia* (Antp) homeotic transcription factor, and others. Synthetic peptides, e.g., having a high basic amino acid content (Lys and Arg) are also of use. See U.S. Patent Pub. No. 20060148104 for additional useful sequences. In some embodiments expression of the recombinase is achieved by infecting cells with a vector, e.g., a virus vector (e.g., a lentivirus, adenovirus, or adeno-associated virus vector) containing an expression cassette containing the sequence encoding the recombinase operably linked to a promoter. The vector may be one that results in transient expression of the recombinase, e.g., that does not stably integrate into the cell's genome or result in a stably inherited episome. In certain embodiments of the invention the engineered somatic cells contain a functional p53 pathway (see Harris, S., and Levine, A, Oncogene, 24: 2899-2908, 2005 for description of p53 pathways). Such cells contain a functional p53 gene and are able to undergo p53-dependent cell cycle arrest and/or cell death in response to various stresses such as DNA damage, hypoxia, and/or exposure to various chemotherapeutic agents (e.g., microtubule inhibitors) known in the art to induce p53-dependent apoptosis in somatic cells. In some embodiments the p53-dependent pathway leads to apoptosis. In some embodiments the p53-dependent pathway leads to cell senescence. One of skill in the art will be able to determine whether cells have a functional p53 pathway, e.g., by exposing cells to conditions known to induce p53-dependent cell cycle arrest or death and determining whether the cells respond in a manner consistent with existence of a functional p53-dependent pathway. In general, noncancerous somatic cells obtained from a mammalian subject are expected to possess functional p53 pathways.

In certain embodiments of the invention the somatic cells are sensitive to DNA demethylation. As used herein, a cell is "sensitive to" DNA demethylation if it displays decreased ability to survive or proliferate under conditions of reduced DNA methylation. DNA methylation is required for survival of a variety of different somatic cell types, particularly those that are proliferating. For example, when the Dnmt1 gene is rendered nonfunctional in proliferating fibroblasts by Cre-mediated recombination, the cells exhibit progressive DNA demethylation between 3-5 days following introduction of a construct from which Cre is expressed, and die between 5 and 6 days following introduction of the construct (Jackson-Grusby, et al.). DNA demethylation is a property shared by proliferating somatic cells of diverse types, consistent with the fact that Dnmt1, 3a, and 3b are essential genes. In contrast, ES cells are able to survive and proliferate in the absence of functional DNMT1 unless induced to differentiate.

In certain embodiments a population of cells of the present invention is characterized in that on average the number of methylated cytosines in the genomic DNA of the cells is reduced by at least 5% relative to the level that would exist under "standard conditions". In some embodiments the population of cells is subjected to conditions such that the number of methylated cytosines in genomic DNA is reduced on average by between 5% and 10%, between 10% and 25%, between 25% and 50%, between 50% and 75%, between 75% and 95%, or by between 95% and 100%, relative to the level that exists under standard conditions. In certain embodiments of the invention the average amount of methylation (i.e., the average number of methylated cytosines) of at least 10, 20, 50, or 100 genes and/or genetic elements such as IAP, L1, LINE, or SINE elements or endogenous retroviral elements is reduced in the population of cells relative to an otherwise identical population of cells that has not been subjected to demethylating conditions. In certain embodiments the average expression level of Dnmt mRNA, e.g., Dnmt1 mRNA, in the population of cells is less than 50% of its normal level. In some embodiments the average expression level of DNMT protein, e.g., DNMT1 protein, in the population of cells is less than 50% of its normal level.

A cell is said to be "resistant to DNA demethylation" if it is able to survive and to proliferate when DNA methylation is reduced to a level that would result in cell cycle arrest or cell death in a proliferating somatic cell such as a primary fibroblast. In certain embodiments of the invention a "proliferating cell" is one that would be expected to divide within 96 hours if maintained under appropriate culture conditions. In certain embodiments the proliferating cell would be expected to divide within 72 hours if maintained under appropriate culture conditions. In some embodiments the cell would be expected to divide within 48 hours, or within 24 hours. In other words, if the cell (and its progeny) is/are maintained in culture under appropriate conditions the total number of cells would double within 24, 48, 72, or 96 hours. "Appropriate culture conditions" refers to standard culture conditions known in the art as being suitable for a somatic cell type of interest to survive and proliferate. See, e.g., Masters, J. (ed.) Animal Cell Culture: A Practical Approach, 3rd ed., Oxford University Press, 2000; Freshey, I., et al., Culture of Animal Cells: A Manual of Basic Technique, 5th ed., Wiley-Liss, 2005.

Reduced DNA methylation can be achieved by (a) inhibiting expression or activity of an endogenous DNA methyltransferase or otherwise inhibiting DNA methylation by an endogenous DNA methyltransferase, e.g., by contacting a cell with an agent that inhibits expression or activity of the endogenous DNA methyltransferase or otherwise inhibits DNA methylation; (b) expressing an agent that inhibits expression or activity of an endogenous DNA methyltransferase or otherwise inhibits DNA methylation by the DNMT in the cell; (c) inhibiting expression or activity of an endogenous protein other than a DNA methyltransferase, which protein is needed for any step of a biochemical pathway that provides a substrate for the transfer of a methyl group to cytosine by a DNA methyltransferase; (d) expressing in the cell an agent that inhibits expression or activity of an endogenous protein other than a DNA methyltransferase, which protein is needed for any step of a biochemical pathway that provides a substrate for the transfer of a methyl group to cytosine by a DNA methyltransferase; and/or (e) culturing the cell under conditions in which it is deprived of nutrients needed for synthesis of a substrate for the transfer of a methyl group to cytosine by a DNA methyltranferase (but in the presence of sufficient nutrients to otherwise support cell viability). Expressing an agent in the cell as described in (b) or (d) can be achieved by contacting the cell with a agent that induces or derepresses such expression or otherwise causes such expression (e.g., by a recombinase-mediated mechanism). A cell that has been treated in any of the afore-mentioned ways (or any other way known in the art) to reduce DNA demethylation is said to have been subjected to "DNA demethylating conditions". For example, a cell that has been contacted with an agent that induces expression of an RNAi agent that inhibits DNMT expression or has been contacted with a DNA methyltransferase inhibitor or a recombinase that inactivates a DNMT gene has been subjected to DNA demethylating conditions.

The DNA methyltransferase can be DNMT, 3a, and/or 3b. In some embodiments expression and/or activity of only DNMT1 is inhibited. In other embodiments expression and/or activity of DNMT1 and either DNMT3a or 3b is inhibited. In some embodiments expression and/or activity of DNMT1, 3a, and 3b are inhibited. In some embodiments the endogenous protein other than a DNMT is an endogenous transporter or enzyme needed for any step of a biochemical pathway that provides a substrate for the transfer of a methyl group to cytosine by a DNA methyltransferase in the cell. In some embodiments a combination of conditions is used, e.g., at least one DNMT is inhibited and cells are cultured in conditions lacking at least some of the nutrients needed for DNA methylation. In another embodiment cells are contacted with a small molecule that inhibits DNA methylation (such as 5'aza-cytidine) and an RNAi agent that inhibits expression of DNMT1, 3a, or 3b is expressed in the cells. In certain embodiments a cell that is sensitive to DNA demethylation undergoes cell cycle arrest or death when DNA methylation is reduced and/or when DNA methyltransferase activity is inhibited, leading to DNA demethylation.

A variety of DNA methylation inhibitors are known in the art and are of use in the invention. See, e.g., Lyko, F. and Brown, R., JNCI Journal of the National Cancer Institute, 7(20):1498-1506, 2005. Inhibitors of DNA methylation include nucleoside DNA methyltransferase inhibitors such as 5-azacytidine, 5-azadeoxycytidine, and zebularine, non-nucleoside inhibitors such as the polyphenol (−)-epigallocatechin-3-gallate (EGCG) and the small molecule RG108 (2-(1,3-dioxo-1,3-dihydro-2H-isoindol-2-yl)-3-(1H-indol-3-yl)propanoic acid), compounds described in WO2005085196 and phthalamides, succinimides and related compounds as described in WO2007007054. Three additional classes of compounds are: (1) 4-Aminobenzoic acid derivatives, such as the antiarrhythmic drug procainamide and the local anesthetic procaine; (2) the psammaplins, which also inhibits histone deacetylase (Pina, I. C., J Org Chem., 68(10):3866-73, 2003); and (3) oligonucleotides, including siRNAs, shRNAs, and specific antisense oligonucleotides, such as MG98. DNA methylation inhibitors may act by a variety of different mechanisms. The nucleoside inhibitors are metabolized by cellular pathways before being incorporated into DNA. After incorporation, they function as suicide substrates for DNMT enzymes. The nonnucleoside inhibitors procaine, epigallocatechin-3-gallate (EGCG), and RG108 have been proposed to inhibit DNA methyltransferases by masking DNMT target sequences (i.e., procaine) or by blocking the active site of the enzyme (i.e., EGCG and RG108). In some embodiments of the invention combinations of DNA methylation inhibitors are used. In some embodiments the concentrations are selected to minimize toxic effects on cells. In some embodiments agents that incorporate into DNA (or whose metabolic products incorporate into DNA) are not employed. In certain embodiments of the invention DNA methylation in a cell is considered "reduced", and the DNA of the cell is considered at least in part "demethylated", if the number of methylated cytosines in the cell's genomic DNA is reduced by at least 5% relative to the level that would exist under "standard conditions", by which are meant conditions within the body of a mammalian subject or appropriate cell culture conditions known and routinely used in the art for cells of a particular type of interest. In some embodiments the number of methylated cytosines in genomic DNA is reduced by between 5% and 10%, between 10% and 25%, between 25% and 50%, between 50% and 75%, between 75% and 95%, or by between 95% and 100%, relative to the level that exists under standard conditions, e.g., prior to administration or induction of expression of an inhibitor of a DNA methyltransferase. In certain embodiments of the invention DNA methylation in a cell is considered "reduced", and the DNA of the cell is considered at least in part "demethylated", if the number of methylated CpG sequences in the cell's genomic DNA is reduced by at least 5% relative to the level that would exist under "standard conditions", by which are meant conditions within the body of a mammalian subject or appropriate cell culture conditions known and routinely used in the art for cells of a particular type of interest. In some embodiments the number of methylated CpG sequences in genomic DNA is reduced by between 5% and 10%, between 10% and 25%, between 25% and 50%, between 50% and 75%, between 75% and 95%, or by between 95% and 100%, relative to the level that exists under standard conditions, e.g., prior to administration or induction of expression of an inhibitor of a DNA methyltransferase. In certain embodiments the cell is subjected to global DNA demethylation. "Global DNA demethylation" refers to DNA demethylation that occurs at many locations in the genome as opposed to at one or a few specific loci. In certain embodiments of the invention global DNA demethylation reduces the methylation (i.e., the number of methylated cytosines) of at least 10, 20, 50, or 100 genes and/or genetic elements such as IAP, L1, LINE, or SINE elements or endogenous retroviral elements. One of skill in the art will readily be able to determine qualitatively whether the cell's DNA is demethylated and/or to determine the extent of demethylation. For example, one of skill in the art could make use of the fact that certain restriction enzymes and/or DNA cleaving agents recognize only methylated DNA. In certain embodiments bisulfite sequencing is employed. In one embodiment bisulfite treatment followed by PCR amplification of DNA repetitive elements is employed (Yang, A. S., et al., Nucl. Acids Res., 32(3): e38, 2004). In certain embodiments HPLC or nearest neighbor analysis is used to quantify the amount of 5-methylcytosine.

In some embodiments cell cycle arrest or death occurs within 30 days or less following subjecting the cells to demethylating conditions, e.g., within 15 days or less, within 10 days, within 5 days, etc. In some embodiments cell cycle arrest or death occurs within 5-6 days following subjecting the cells to demethylating conditions. In some embodiments, cell cycle arrest or death occurs within 10 times the time required for the cell to complete 10 cell cycles under non-demethylating conditions, e.g., between 5-10 cell cycle times or between 2-5 cell cycle times following subjecting the cells to demethylating conditions. In some embodiments cell cycle arrest or death occurs within 30 days or less following inducing expression of an RNAi agent targeted to a Dnmt gene in the cells, e.g., within 15 days or less, within 10 days, within 5 days, etc. In some embodiments cell cycle arrest or death occurs within 5-6 days following inducing expression of an RNAi agent targeted to a Dnmt gene in the cells. In some embodiments, cell cycle arrest or death occurs within 10 times the time required for the cell to complete 10 cell cycles under conditions in which the Dnmt gene is expressed normal, e.g., between 5-10 cell cycle times or between 2-5 cell cycle times following inducing the expression of an RNAi agent targeted to a Dnmt gene in the cells. In some embodiments cell cycle arrest or death occurs after 30 days or less during which the average expression level of Dnmt mRNA, e.g., Dnmt1 mRNA, is less than 50% of its normal level, e.g., after 15 days or less, after 10 days or less, or after 5 days or less. In some embodiments cell cycle arrest or death occurs after 30 days or less during which the average expression level of DNMT protein, e.g., DNMT1 protein, is less than 50% of its normal level, e.g., within 15 days or less, after 10 days, after 5 days, etc. In some embodiments cell cycle arrest or death occurs after 30 days or less during which the average methyltransferase activity level of DNMT protein, e.g., DNMT1 protein, is less than 50% of its normal level, e.g., after 15 days or less, after 10 days or less, or after 5 days or less.

It will be appreciated that the methods of the invention are often practiced using populations of somatic cells. A population of somatic cells is said to be sensitive to DNA demethylation if at least 90% of the cells are sensitive to DNA demethylation. In some embodiments at least 95%, 96%, 97%, 98%, 99%, 99.5%, 99.8%, 99.9, 99.95% or more of the cells are sensitive to DNA demethylation. Thus when the cells are subjected to demethylating conditions, at least at least 95%, 96%, 97%, 98%, 99%, 99.5%, 99.8%, 99.9%, 99.95% or more of the cells undergo cell cycle arrest or die within a selected time period, e.g., within 30 days, within 15 days, within 10 days, etc. The population of cells may be of a single type and may be substantially free of other cell types. "Substantially free" as used herein refers to at least about 80% pure, preferably 85%, 90%, 95%, 99% or more pure population of the desired cells in the whole cell population. In some embodiments the cells are cultured in medium that supports growth of only a desired cell type for a period of time, thereby resulting in a population of cells substantially free of other cell types.

In certain embodiments of the invention, reprogrammed somatic cells are identified by a method that comprises selecting for cells that are resistant to DNA demethylation. The invention provides a method of identifying a somatic cell that has been at least in part reprogrammed to an ES-like state, the method comprising steps of: (a) providing somatic cells, at least some of which have been at least in part reprogrammed to an ES-like state; and (b) selecting a cell that is resistant to DNA demethylation, thereby identifying a cell that has an increased likelihood of having been reprogrammed, e.g., reprogrammed to an ES-like state. In some embodiments at least some of the cells identified using the method have been reprogrammed to an ES-like state. In some embodiments at least some of the cells have been at least in part reprogrammed to an ES-like state, such that they are more susceptible to reprogramming to a pluripotent state when subjected to one or more additional treatments than cells that are not resistant to DNA demethylation.

The method makes use of the fact that many or most somatic cell types are sensitive to DNA demethylation, i.e., they cannot survive or proliferate for prolonged periods of time without the ability to maintain sufficient methylation of their genomic DNA. In contrast, ES cells are resistant to DNA demethylation and can survive in the absence of endogenous DNA methyltransferase. In some embodiments a population of somatic cells is subjected to conditions under which at least 70%, at least 80%, or at least 90% of unreprogrammed somatic cells of that cell type would be expected to cease proliferating or to die within 30 days after being subjected to the conditions. In some embodiments at least 90% of unreprogrammed somatic cells of that type would be expected to cease proliferating or die within 20 days after being subjected to the conditions. In some embodiments a population of somatic cells is subjected to conditions under which at least 95% of unreprogrammed somatic cells of that cell type would be expected to cease proliferating or to die within 15 days after being subjected to the conditions. In another embodiment a population of somatic cells is subjected to conditions under which at least 99% of unreprogrammed somatic cells of that cell type would be expected to cease proliferating or to die within 10 days after being subjected to the conditions. In some embodiments the cells are human cells. In some embodiments the somatic cells are proliferating cells. In some embodiments the somatic cells are fibroblasts. In certain embodiments the somatic cells express an exogenously introduced reprogramming factor. In certain embodiments the cells have been contacted with a reprogramming agent. In some embodiments the cells are subjected to conditions under which DNA is demethylated. In certain embodiments the somatic cells reversibly express an RNAi agent targeted to an endogenous DNA methyltransferase. In certain embodiments, the method further comprises after the cell is selected, inhibiting (i.e., reducing or eliminating) the expression of the RNAi agent in the selected somatic cell, thereby allowing the genomic DNA of the selected somatic cell to become methylated. Thus DNA methylation can occur as the cell is maintained in culture and/or as its progeny are induced to differentiate.

The invention further provides a method of identifying a somatic cell that has been at least in part reprogrammed to a pluripotent state, the method comprising providing somatic cells that are sensitive to DNA demethylation; contacting the cells with one or more factors capable of reprogramming somatic cells; treating the cells so as to reduce methylation of genomic DNA; maintaining the cells in culture for a time period; and identifying a cell that is alive after said time period, thereby identifying a cell that has an increased likelihood of having been at least in part reprogrammed to a pluripotent state. In some embodiments at least some of the cells identified using the method have been reprogrammed to an ES-like state. In some embodiments at least some of the cells have been at least in part reprogrammed to an ES-like state, such that they are more susceptible to reprogramming to a pluripotent state when subjected to one or more additional treatments than cells that are not resistant to DNA demethylation. In certain embodiments of the invention the cells are then subjected to such additional treatment(s). One of skill in the art will be able to test a population of somatic cells to determine the conditions and the time period needed such that a desired fraction of the cells in a population will not survive when subjected to demethylating conditions.

For example, one may culture the cells after inducing expression of an RNAi agent targeted to the Dnmt1 gene and count the number of viable cells at different time points to determine the length of time ("X" hours or days) needed for at least 80%, at least 90%, at least 95%, or at least 99% of the cells to be killed as a consequence of reduced DNA methylation. When practicing the inventive methods, cells that have been treated with an agent capable of reprogramming cells and are viable after X hours or days are potentially reprogrammed. It will be appreciated that not all viable cells may be reprogrammed. For example, some of the cells may not express the RNAi agent at levels sufficient to kill unreprogrammed cells. The cells may be subjected to one or more additional selections or tests to determine whether they are reprogrammed or to select from the potentially reprogrammed cells those that are reprogrammed. For example, cells that are viable after time X may be subjected to a screen or selection for cells that have two transcriptionally active X chromosomes (in the case of cells derived from a female), and/or may be screened or selected for cells that express one or more markers characteristic of ES cells, etc.

The invention further provides a method of identifying a differentiated somatic cell that has been reprogrammed to a pluripotent state, the method comprising providing a population of cells, at least some of which have been reprogrammed to a pluripotent state, wherein said cell comprises a polynucleotide encoding a selectable marker operably linked to expression control elements that regulate expression of an endogenous pluripotency gene in such a manner that expression of the selectable marker substantially matches expression of the endogenous pluripotency gene, and identifying a cell that expresses the selectable marker, thereby identifying a somatic cell that has an increased likelihood of having been reprogrammed to a pluripotent state (relative to cells that do not express the selectable marker). In some embodiments, the endogenous pluripotency gene is Oct-4 or Nanog. In some embodiments the method further comprises selecting a cell or colony of cells having a morphology characteristic of an ES cell or ES cell colony. Morphological criteria known in the art can be used to select such cells or colonies.

In a further embodiment of the invention, reprogrammed somatic cells are identified by selecting for cells that contain two transcriptionally active X chromosomes. In one embodiment the invention provides a method of identifying a somatic cell that has an increased likelihood of having been reprogrammed to an ES-like state, the method comprising providing somatic cells that contain two X chromosomes, one of which is inactive; subjecting the cells to one or more treatments that reprogram somatic cells; and identifying a cell in which the inactive X chromosome has become active, thereby identifying a cell that has an increased likelihood of having been reprogrammed, e.g., reprogrammed to an ES-like state. In some embodiments at least some of the cells identified using the method have been reprogrammed to an ES-like state. In some embodiments at least some of the cells have been at least in part reprogrammed to an ES-like state, such that they are more susceptible to reprogramming to a pluripotent state when subjected to one or more additional treatments than cells that do not have two transcriptionally active X chromosomes. In certain embodiments of the invention the cells are then subjected to such additional treatment(s).

In certain embodiments the somatic cells contain two X chromosomes, one of which is inactive, wherein one of the X chromosomes contains a functional allele of a selectable marker gene and the other X chromosome does not contain a functional allele of said selectable marker gene. In certain embodiments the selectable marker gene is an endogenous gene normally present on the X chromosome. In certain embodiments the somatic cells contain two X chromosomes, one of which is inactive, wherein both of the X chromosomes contain a functional allele of a selectable marker gene.

In certain embodiments the somatic cells contain two X chromosomes, one of which is inactive, wherein both of the X chromosomes contain a functional allele of a selectable marker gene that is useful for both positive and negative selection, and the method comprises: (a) selecting cells that do not express the selectable marker gene, thereby obtaining a population of cells in which a first X chromosome is transcriptionally inactive; (b) subjecting the cells to one or more treatments that reprogram the cells; (c) functionally inactivating the selectable marker gene on said first X chromosome; and (d) selecting cells that express the selectable marker gene, thereby selecting cells in which the second X chromosome is transcriptionally active. In certain embodiments the selectable marker gene is an endogenous gene normally present on the X chromosome, e.g., the Hprt gene.

The invention further provides a method of identifying a somatic cell having an increased likelihood of having been reprogrammed to an ES-like state, the method comprising steps of: (a) providing somatic cells that have an active X chromosome that lacks a functional allele of a selectable marker and an inactive X chromosome that contains a functional allele of said selectable marker; (b) subjecting the cells to one or more treatments capable of reprogramming somatic cells; and (c) selecting cells that express the selectable marker gene, thereby selecting cells in which the inactive X chromosome has become transcriptionally active. Such cells have an increased likelihood of having been reprogrammed to an ES-like state relative to cells in which the inactive X chromosome has not become transcriptionally active.

The invention further provides a method of identifying a somatic cell that has an increased likelihood of having been reprogrammed to an ES-like state, the method comprising: (a) providing somatic cells that contain two X chromosomes, one of which is inactive, wherein one of the X chromosomes contains a functional allele of a selectable marker gene and the other X chromosome does not contain a functional allele of the selectable marker gene; (b) selecting cells that do not express the selectable marker gene, thereby selecting cells in which the inactive X chromosome contains a functional allele of the selectable marker gene; (c) subjecting the cells to one or more treatments capable of reprogramming somatic cells; and (d) selecting cells that express the selectable marker gene, thereby selecting cells in which the inactive X chromosome has become transcriptionally active. Such cells have an increased likelihood of having been reprogrammed to an ES-like state relative to cells in which the inactive X chromosome has not become transcriptionally active.

Somatic cells that have a first X chromosome that lacks a functional allele of a selectable marker can be prepared in a variety of ways. For example, homologous recombination could be used to delete all or part of the allele. Cells in which the allele was successfully inactivated can be selected using conventional methods. Alternatively, the cells may not be genetically engineered but may instead harbor a mutation that inactivates the gene. The cells may have been exposed to a mutagen or condition such as UV radiation to increase the proportion of cells having such a mutation or the mutation may spontaneously arise under selective pressure. In one embodiment, the selectable marker is one that is usable for positive and negative selection such as Hprt. In such embodiments cells in which one X chromosome lacks a functional allele of the gene are selected under conditions that select against cells that express the marker. For example in the case of Hprt, cells may be selected by culturing them in medium containing thioguanine. After subjecting the cells to a treatment capable of reprogramming somatic cells, cells that express the marker are selected, e.g., by culturing in HAT medium. Such cells will have reactivated the inactive X chromosome and thus have an increased likelihood of having been reprogrammed. At least some of the cells identified using the method are reprogrammed somatic cells.

Certain methods of the invention include a step of selecting cells that express a marker that is expressed by multipotent or pluripotent cells. The marker may be specifically expressed in such cells. One could culture potentially reprogrammed cells in the presence of antibodies that have a detectable label attached thereto and use flow cytometry (e.g., fluorescence activated cell sorting) to separate cells that express the marker (indicative of a reprogrammed state) from cells that do not. In other embodiments, an affinity-based separation method is used to separate reprogrammed cells from cells that are not reprogrammed. In one embodiment, reprogrammed somatic cells are selected by contacting the cells with a solid or semi-solid support that has a binding agent that specifically binds to an ES cell surface marker attached thereto. The support has a surface to which a binding agent can be bound. The surface could comprise, e.g., plastic (polypropylene, polyvinyl chloride, polyvinylidene chloride, polytetrafluorethylene, polyethylene, polyamides), glass, metal (e.g., silicon), agarose, etc. Useful supports include agarose or agarose-based matrices (e.g., agarose or sepharose beads), particles that consist at least in part of a magnetic material, particles comprising polymers such as styrene or latex, tissue culture vessels or plates, tubes (e.g., microfuge tubes), membranes, etc. In some embodiments the support is a population of particles such as magnetic beads. Such particles are often under 100 microns in longest axial dimension, e.g., between 1 and 10 microns, and often approximately spherical. Magnetic beads and methods of using them for cell separation are known in the art and are commercially available from many sources. For example, Dynabeads (Dynal Biotech, Norway) are superparamagnetic polymer beads that have a dispersion of magnetic material throughout with a thin polymer shell. Binding agents can be covalently or noncovalently attached to the surface using conventional methods. The binding agent could be a naturally occurring or artificial peptide or polypeptide, small molecule, nucleic acid (e.g., an aptamer), that specifically binds to the ES cell surface marker. In one embodiment the binding agent is an antibody or antibody fragment. In another embodiment the binding agent is a ligand for a receptor. In some embodiments cells are incubated in a liquid medium in the presence of magnetic beads that have a binding agent attached thereto. A magnetic force is used to retrieve the beads from the medium. For example, the beads may be attracted to the side of a vessel and the medium removed. Cells are recovered from the beads, or the beads are removed from the cells, using standard methods such as competition with the binding agent or by contacting the beads with an affinity reagent that binds to a molecule present on the surface of the beads but does not bind to the cells.

Alternately or additionally, one could select cells that do not express markers characteristic of somatic cells from which the potentially reprogrammed cells were derived and which are not expressed in ES cells generated using conventional methods. For example, one could incubate cells in the presence of a first binding agent (e.g., an antibody) that binds to a marker characteristic of a somatic cell and not found on a pluripotent cell. If the binding agent is labeled, flow cytometry could be used to isolate cells that do not have the antibody attached thereto. In another embodiment, a second binding agent that binds to the first the binding agent is used to remove cells that have the first binding agent bound thereto. In another embodiment the first binding agent is crosslinked and precipitated to remove cells that express a marker characteristic of somatic cells. Other methods of separating cells may utilize differences in average cell size or density that may exist between pluripotent cells and somatic cells. For example, cells can be filtered through materials having pores that will allow only certain cells to pass through.

The methods of the invention may be combined in any order. In some embodiments cell that express a first ES cell marker are selected, and the cells are then assessed for an additional pluripotency characteristic such as expression of a second ES cell marker, resistance to DNA methylation, having two transcriptionally active X chromosomes, etc. In some embodiments cell that are resistant to DNA methylation and/or have two transcriptionally active X chromosomes are selected, thereby providing a population of cells enriched for reprogrammed cells. The cells are then subjected to an additional enrichment step comprising selecting cells that express a first ES cell marker. Optionally the cells are then tested to determine whether they express a second ES cell marker. Any number of markers may be used to enrich for ES-like cells and/or their expression assessed.

The invention thus allows the artisan to prepare a purified preparation of pluripotent reprogrammed somatic cells. Somatic cells may be reprogrammed to gain either a complete set of the pluripotency characteristics and are thus pluripotent. Alternatively, somatic cells may be reprogrammed to gain only a subset of the pluripotency characteristics. In another alternative, somatic cells may be reprogrammed to be multipotent.

The instant specification provides a number of methods to identify and/or select reprogrammed cells, wherein the cells have a genetic modification usable for such purposes and/or wherein a chemical or genetic selection based on such genetic modification is employed. However, as described herein, somatic cells that have been reprogrammed to an ES-like state can be identified without use of such chemical or genetic selection. Thus the invention further provides methods of deriving reprogrammed somatic cells from somatic cells that are not genetically modified, and further provides reprogrammed somatic cells derived using the inventive methods. In some embodiments somatic cells that are not genetically modified can be obtained from a variety of species. For example, suitable cells can be obtained from mice, rats, rabbits, farm animals (e.g., sheep, goats, horses, cows and the like), companion animals (e.g., dogs, cats and the like), primates and humans and used to derive ES-like pluripotent or multipotent cells. In some embodiments the methods employ morphological criteria to identify colonies containing reprogrammed somatic cells from a population of cells. The colonies are subcloned and/or passaged once or more in certain embodiments, thereby obtaining a population of cells enriched for ES-like cells. The enriched population may contain at least 80%, 85%, 90%, 95%, 96%, 97%, 98%, 99% or more, e.g., 100% ES-like cells. The invention provides cell lines of somatic cells that have been stably and heritably reprogrammed to an ES-like state.

"Genetic selection" encompasses methods in which genetic material (e.g., DNA) is introduced into cells, wherein introduced genetic material allows desired cells (e.g., cells having one or more desired characteristics) to be distinguished from other cells. For example, an endogenous pluripotency gene linked to DNA encoding a detectable marker such as a fluorescent protein, would allow genetic selection. "Chemical selection" encompasses methods that involve exposing cells to a chemical agent that exerts negative selective pressure on undesired cells, e.g., kills them or reduces their rate of proliferation and/or allows only desired cells to survive and/or proliferate. For example, an endogenous pluripotency gene linked to DNA encoding a drug resistance marker such as neo, would allow chemical selection by culturing cells in the presence of a chemical agent (e.g., G418) that kills cells not expressing the drug resistance marker. Such selection would also be considered a genetic selection since it makes use of introduced genetic material. In some embodiments, a chemical selection method is employed, but the method does not depend on the presence of genetic material not naturally found in the cell. For example, the chemical selection may be directed against a naturally occurring cell product, e.g., a cell surface marker. In some embodiments the chemical selection method does not employ an antibiotic.

The invention provides methods of deriving reprogrammed somatic cells from somatic cells without requiring genetic modification of the cells that are to be reprogrammed. In some embodiments, the reprogrammed somatic cells do not contain exogenous genetic material introduced into the genome of said cells (or ancestors of said cells) by the hand of man. In some embodiments the reprogrammed somatic cells do not contain genetic material introduced either transiently into the cells or introduced stably into the genome of said cells (or ancestors of said cells) by the hand of man. In some embodiments, cells are transiently transfected with a construct that encodes a protein that contributes to reprogramming, wherein the construct encodes a drug resistance marker or other selectable marker. Selective pressure is maintained for a sufficient period of time for the cells to become reprogrammed. Subsequently, after a sufficient period of time for the cells to become at least in part reprogrammed and/or to activate endogenous pluripotency gene(s) such as Oct4, a second selection is applied to select cells that have lost the construct. In some embodiments the reprogrammed somatic cells do contain exogenously introduced genetic material in their genome, but such genetic material is introduced for purposes of (i) inducing the reprogramming process and/or (ii) correcting a genetic defect in such cells or enabling such cells to synthesize a desired protein for therapeutic purposes and, in either case, is not used to select reprogrammed cells. It will be appreciated that genetic modifications performed in order to induce reprogramming are distinct from genetic modifications whose purpose is to allow selection of reprogrammed cells and does not itself contribute to reprogramming.

In some embodiments, the methods employ morphological criteria to identify reprogrammed somatic cells from among a population of somatic cells that are not reprogrammed. In some embodiments, the methods employ morphological criteria to identify somatic cells that have been reprogrammed to an ES-like state from among a population of cells that are not reprogrammed or are only partly reprogrammed to an ES-like state. "Morphological criteria" is used in a broad sense to refer to any visually detectable aspect of the size, shape, structure, organization, and/or physical form of the cells or colonies. Identification based on morphological is distinct from identification based on visually detectable expression of a particular selectable marker (e.g., a fluorescent protein) by the cells. Morphological criteria include, e.g., the shape of the colonies, the sharpness of colony boundaries (with sharp boundaries characterizing colonies of ES-like cells), the density of the cells in the colonies (with increased density characterizing colonies of ES-like cells), and/or the small size and distinct shape of the reprogrammed cells relative to non-reprogrammed cells, etc. The invention encompasses identifying and, optionally, isolating colonies (or cells from colonies) wherein the colonies display one or more such characteristics depicted in these figures.

The reprogrammed somatic cells may be identified as colonies growing in a first tissue culture dish, and the colonies, or portions thereof, transferred to a second tissue culture dish, thereby isolating reprogrammed somatic cells. "Tissue culture dish" as used herein refers to any vessel, plate, receptacle, container, etc., in which living cells can be maintained in vitro. The bottom of the tissue culture dish may be at least in part coated with a substrate, e.g., a protein or mixture thereof such as gelatin, Matrigel, fibronectin or other cell adhesion molecule, collagen, protein-based or non-protein based hydrogel, etc., on which the cells are disposed. In some embodiments the dish contains a feeder cells (optionally irradiated), which may at least in part coat the bottom of the dish.

In some embodiments, the methods employ complement-mediated lysis to eliminate at least some non-reprogrammed somatic cells from a population of cells that contains at least some reprogrammed somatic cells. In one embodiment, a population of somatic cells is contacted with a complement-fixing antibody (e.g., an IgG or IgM antibody) that binds to a cell surface marker that is not detectably expressed by pluripotent cells, e.g., ES cells (or is expressed at much lower, e.g., insignificant levels by such cells) but is expressed by unreprogrammed somatic cells (e.g., unreprogrammed fibroblasts). Such lower levels may be, e.g., less than 20%, less than 10%, less than 5%, or less than 1% the average level of expression found in unreprogrammed cells in various embodiments of the invention, or such level as will not be sufficient to support complement-mediated lysis of a majority of the cells. The cells are further contacted with complement components ("complement") sufficient to mediate lysis of the cells to which the antibody is bound. In one embodiment the cells are contacted with serum, e.g., mouse or human serum containing complement. In one embodiment the cells are contacted with recombinant complement components (e.g., complement components sufficient to mediate the classical pathway such as C1, C2, C3, C4, C5, and C6-C9). Cells that survive in the presence of complement and the antibody are identified as having an increased likelihood of being reprogrammed. The method is of use to enrich or select for reprogrammed cells. In one embodiment, the cell surface marker is an MHC Class I antigen ("MHC"). For example, as shown in Example 9, mouse cells that have been reprogrammed to an ES-like state (iPS cells) turn off MHC. Cells picked randomly after transduction with factors that result in reprogramming and sorted for Oct4 activation are MHC negative. Furthermore, MHC negative cells in a cell population transduced with the factors are more likely to be reprogrammed. Infected cells sorted for MHC negative: many more colonies than in high MHC population. Complement-mediated depletion (killing of un-reprogrammed cells) leads to enrichment of SSEA1 positive cells. Complement-mediated selection leads to much higher number of colonies exhibiting morphological features indicative of reprogramming.

In some embodiments of the invention two or more methods, neither of which employs genetic or chemical selection, are employed. For example, the invention provides a method of deriving reprogrammed cells comprising steps of: (i) providing a population of non-genetically modified cells, at least some of which are partly or fully reprogrammed to an ES-like state; (ii) enriching for partly or fully reprogrammed cells using complement-mediated lysis to eliminate at least some unreprogrammed cells; and (iii) identifying reprogrammed cells or colonies comprising such cells using morphological criteria.

Any of the methods of the invention that relate to generating, selecting, or isolating a reprogrammed somatic cell may include a step of obtaining a somatic cell or obtaining a population of somatic cells from a donor in need of cell therapy. Reprogrammed somatic cells are generated, selected, or identified from among the obtained cells or cells descended from the obtained cells. Optionally the cell(s) are expanded in culture prior to generating, selecting, or identifying reprogrammed somatic cell(s) genetically matched to the donor.

Methods for Screening for an Agent that Reprograms Somatic Cells

The present invention also provides methods for identifying an agent that reprograms somatic cells to a less-differentiated state, as well as the agents thus identified. In one embodiment, the methods comprise contacting the engineered or selected somatic cells of the invention with a candidate agent, selecting for cells that express the appropriate selectable marker. The presence of cells that express the appropriate selectable marker indicates that the agent reprograms somatic cells. Such an agent is referred to as a "reprogramming agent" or "an agent that reprograms cells" for purpose of this application. In some embodiments of the invention the reprogramming agent is not Sox2, Oct4, c-myc, Klf4 or Nanog.

In a further embodiment, the methods comprise contacting the engineered somatic cells of the invention with a candidate agent, selecting for cells that express the appropriate selectable marker, and assessing the cells so selected for pluripotency characteristics. The presence of a complete set of pluripotency characteristics indicates that the agent reprograms somatic cells to become pluripotent.

In a further embodiment the invention provides a method of identifying an agent that reprograms somatic cells to a less differentiated state, the method comprising steps of: (a) contacting somatic cells with a candidate reprogramming agent, wherein the somatic cells are sensitive to reduced DNA methylation; and (b) determining whether more of the cells are resistant to reduced DNA methylation than would be expected if the agent does not reprogram somatic cells, wherein the candidate reprogramming agent is identified as a reprogramming agent if more of the cells are resistant to reduced DNA methylation than would be expected if the candidate reprogramming agent does not reprogram somatic cells. In certain embodiments the method comprises maintaining the cells in culture under conditions of reduced DNA methylation and determining whether more of the cells survive than would be expected if the agent does not reprogram somatic cells. In certain embodiments of the invention the cells are proliferating cells, i.e., they are not post-mitotic.

In a further embodiment the invention provides a method of identifying an agent that reprograms somatic cells to a less differentiated state, the method comprising steps of: (a) contacting somatic cells with a candidate reprogramming agent, wherein the somatic cells are sensitive to reduced DNA methylation; and (b) determining the amount of cells that are resistant to reduced DNA methylation, wherein an increased amount of cells that are resistant to reduced DNA methylation, as compared to a control, is indicative of the candidate agent being a reprogramming agent. The control may be a parallel sample that has not been treated with the candidate agent, or which has been treated with a candidate having a known effect (e.g., a positive effect, a negative effect, or no effect). Alternatively, the control may be a predetermined value for a particular assay.

The cells may be treated so as to reduce methylation of genomic DNA, e.g., by inhibiting expression of a DNA methyltransferase and/or by contacting the cells with an agent that inhibits DNA methyltransferase activity or otherwise inhibits any step in the pathway leading to DNA methylation. Suitable methods and agents are described above. In one embodiment, DNA methylation is reduced by reversibly inducing expression of an interfering RNA in the cells, wherein the interfering RNA inhibits expression of a DNA methyltransferase such as DNMT1. In some embodiments, expression of Dnmt (e.g., Dnmt1) mRNA is reduced in the cells on average by at least 50%, at least 90%, or more. In some embodiments, expression of a DNMT protein, e.g., a DNMT1 protein, is reduced in the cells on average by at least 50%, at least 90%, or more. Engineered somatic cells useful for practicing the methods are described above.

The cells may be maintained in culture for a period of time after being contacted with the candidate reprogramming agent but before subjecting the cells to conditions under which DNA demethylation occurs. For example, the cells may be maintained in the presence of the candidate reprogramming agent for between 1 and 12 hours, between 12 and 24 hours, between 24 and 48 hours, between 48 and 72 hours, etc., prior to subjecting the cells to DNA demethylating conditions. Alternately the cells can be contacted with the agent after the DNA demethylating conditions have been imposed, e.g., up to 1, 2, 5, or 10 days after DNA demethylating conditions have been imposed. The candidate reprogramming agent may, but need not be, present while the cells are subjected to conditions under which DNA demethylation occurs. The cells may be maintained in culture under conditions of reduced DNA methylation, e.g., under conditions in which expression of one or more endogenous DNMT proteins is reduced. If cells are able to survive and/or proliferate under such conditions in greater numbers than would be expected if the cells are not reprogrammed, then the agent is identified as one that reprograms somatic cells. The cells may be maintained in culture for, e.g., at least 5 days, up to 10 days, up to 15 days, up to 30 days, etc., under conditions of reduced DNA methylation. In some embodiments the agent is identified as an agent that reprograms cells if there are at least 2, 5, or 10 times as many viable cells after said time period if the cells have been contacted with the candidate agent than if the cells have not been contacted with the agent.

The presence of living cells can be assessed using any method known in the art for assessing cell viability. For example, the ability of the cells to exclude a dye, ability of cells to carry out an enzymatic reaction, MTT assay, measuring incorporation of a labeled substrate, or visual observation under a microscope are examples of methods that can be used to determine whether there are living cells and to quantify them. In some embodiments viable cells produce a fluorescent or luminescent signal. In some embodiments, the assay comprises determining whether the cells are undergoing apoptosis. For example, expression of genes that induce or participate in apoptosis such as caspases can be assessed, or an assay that examines DNA fragmentation can be used.

In some embodiments the method further comprises determining whether the cells have an intact p53 pathway, such that the cells could under p53-dependent apoptosis and/or cell cycle arrest. In some embodiments cells that are resistant to DNA demethylation but are still able to undergo p53-dependent apoptosis are selected. Thus in certain embodiments the candidate agent is not one that inhibits p53 or a gene required for cells to undergo p53-dependent apoptosis.

The invention further provides a method of identifying an agent that reprograms somatic cells to a less differentiated state, the method comprising steps of: (a) providing somatic cells containing two X chromosomes, one of which is inactive; (b) contacting the somatic cells with a candidate reprogramming agent; (c) maintaining the cells in culture; (d) determining whether more of the cells reactivate their inactive X chromosome while in culture than would be expected if the candidate agent does not reprogram somatic cells, wherein the candidate agent is identified as a reprogramming agent if more of the cells reactivate their inactive X chromosome than would be expected if the candidate reprogramming agent does not reprogram somatic cells. In one embodiment the method comprises steps of: (a) providing somatic cells containing two X chromosomes, one of which is inactive, wherein one of the X chromosomes contains a functional allele of a selectable marker gene and the other X chromosome does not contain a functional allele of said selectable marker gene; (b) selecting cells that do not express the selectable marker, thereby selecting cells in which the X chromosome that contains the selectable marker gene is inactive; (c) contacting the somatic cells selected in step (b) with a candidate reprogramming agent; (d) determining whether more of the cells express the selectable marker than would be expected if the X chromosome that contains the functional allele of the selectable marker gene remains inactive, thereby determining whether more of the cells reactivated their inactive X chromosome than would be expected if the candidate reprogramming agent does not reprogram somatic cells; and (e) identifying the candidate agent as a reprogramming agent if more of the cells reactivate their inactive X chromosome than would be expected if the candidate reprogramming agent does not reprogram somatic cells. In one embodiment the afore-mentioned method comprises steps of: selecting cells that express a functional form of the selectable marker after contacting the cells with the candidate reprogramming agent, thereby selecting for cells that have reactivated their inactive X chromosome. In certain embodiments of the invention the selectable marker is suitable for positive selection and negative selection. In certain embodiments the method comprises maintaining the cells under conditions in which cells that express a functional form of the selectable marker substantially do not survive; and after treating the cells with a candidate reprogramming agent maintaining cells under conditions in which cells that do not express a functional form of the selectable marker substantially do not survive. In certain embodiments the gene is an endogenous gene present on the X chromosome, e.g., the gene encodes hypoxanthine-guanine phosphoribosyltransferase (HPRT). In certain embodiments the X chromosome that lacks a functional allele of said gene contains an engineered genetic modification that inactivates the gene. In certain embodiments the method comprises steps of:

(a) providing somatic cells containing two X chromosomes, one of which is inactive, wherein one of the X chromosomes contains a functional allele of a first selectable marker gene whose expression can be selected against and a functional form of a second selectable marker gene whose expression can be selected for, and wherein the other X chromosome lacks a functional allele of each of said genes; (b) selecting cells that do not express a functional form of the first selectable marker, thereby selecting cells in which the X chromosome that contains the functional allele is inactive; (c) contacting the somatic cells with a candidate reprogramming agent; (d) selecting cells that express a functional form of the second selectable marker, thereby selecting for cells that have reactivated their inactive X chromosome; (e) determining whether more of the cells reactivated the inactive X chromosome than would be expected if the candidate reprogramming agent does not reprogram somatic cells; and (f) identifying the candidate agent as a reprogramming agent if more of the cells reactivated their inactive X chromosome than would be expected if the candidate reprogramming agent does not reprogram somatic cells.

Candidate agents used in the invention encompass numerous chemical classes, though typically they are organic molecules, including small organic compounds (e.g., compounds having a molecular weight equal to or less than 1500 daltons and multiple carbon-carbon bonds). Candidate agents are also found among biomolecules including peptides, saccharides, fatty acids, steroids, purines, pyrimidines, nucleic acids and derivatives, structural analogs or combinations thereof.

Candidate agents may be naturally arising, recombinant or designed in the laboratory. The candidate agents may be isolated from microorganisms, animals, or plants, or may be produced recombinantly, or synthesized by chemical methods known in the art. In some embodiments, candidate agents are isolated from libraries of synthetic or natural compounds using the methods of the present invention. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, including acylation, alkylation, esterification, amidification, to produce structural analogs.

There are numerous commercially available compound libraries, including, for example, the Chembridge DIVERSet. Libraries are also available from academic investigators, such as the Diversity set from the NCI developmental therapeutics program.

The screening methods mentioned above are based on assays performed on cells. These cell-based assays may be performed in a high throughput screening (HTS) format, which has been described in the art. For example, Stockwell et al. described a high-throughput screening of small molecules in miniaturized mammalian cell-based assays involving post-translational modifications (Stockwell et al., 1999). Likewise, Qian et al. described a leukemia cell-based assay for high-throughtput screening for anti-cancer agents (Qian et al., 2001). Both references are incorporated herein in their entirety.

A reprogramming agent may belong to any one of many different categories. For example, a reprogramming agent may be a chromatin remodeling agent. A chromatin remodeling agent may be a protein involved in chromatin remodeling or an agent known to alter chromatin toward a more open structure, such as a DNA methylation inhibitor or a histone deacelyation inhibitor. Exemplary compounds include 5-aza-cytidine, TSA and valproic acid. For another example, such an agent may be a pluripotency protein, including, for example, Nanog, Oct-4 and Stella. Such an agent may also be a gene essential for pluripotency in at least some contexts, including, for example, Sox2, FoxD3, and LIF, and Stat3. See Smith et al. 1988, William et al., 1988, Ihle, 1996, Avilion et al., 2003, and Hanna et al., 2002). It will be appreciated that the candidate reprogramming agent is typically one that is not present in standard culture medium, or if present is present in lower amounts.

It will also be appreciated that a useful reprogramming agent or other form of reprogramming treatment need not be capable of reprogramming all types of somatic cells and need not be capable of reprogramming all somatic cells of a given cell type. If the treatment results in a population enriched for reprogrammed cells relative to the untreated population (i.e., has a higher proportion of reprogrammed cells than the starting population), it is of use in the present invention. For example, and without limitation, a reprogramming treatment that reprograms between 0.000001% and 100% of the treated cells is of use. Also, methods that provide a population of somatic cells that is enriched for reprogrammed cells are of use even if a substantial fraction of the cells are not reprogrammed. Cells in such a population have an increased likelihood of being reprogrammed cells relative to an otherwise equivalent population of cells that has not been subjected to the method. Without limitation, and by way of example, a screen or selection that results in a population of cells in which at least 5% of the cells are reprogrammed is of use. Without limitation, a method that results in a population that is enriched for reprogrammed cells by a factor of 2, 5, 10, 50, 100 or more (i.e., the fraction of reprogrammed cells in the population is 2, 5, 10, 50, or 100 times more than present in a starting population) is of use. Multiple selection and/or screening procedures can be employed to provide populations of cells that are increasingly enriched for reprogrammed cells.

In one embodiment of the invention, induced pluripotent cells for use in screening for candidate reprogramming agents are prepared by a method comprising providing one or more somatic cells that each contain at least one exogenously introduced factor that contributes to reprogramming of said cell to a pluripotent state, wherein each of said exogenously introduced factors is introduced using an inducible vector which is not subject to methylation-induced silencing and the expression of which is controlled by regulatory elements induced by distinct inducers (i.e., each exogenously introduced factor is separately inducible); (b) maintaining said one or more cells under conditions appropriate for proliferation of said cells and for activity of said at least one exogenously introduced factor for a period of time sufficient to reprogram said cell or to activate at least one endogenous pluripotency gene; (c) functionally inactivating said at least one exogenously introduced factor; (d) selecting one or more cells which display a marker of pluripotency; (e) generating a chimeric embryo utilizing said one or more cells which display a marker of pluripotency; (f) obtaining one or more somatic cells, e.g., differentiated somatic cells, from said chimeric embryo; (g) maintaining said one or more somatic cells under conditions appropriate for proliferation of said cells and for activity of said at least one exogenously introduced factor for a period of time sufficient to activate at least one endogenous pluripotency gene; and (h) differentiating between cells which display one or more markers of pluripotency and cells which do not. In a preferred embodiment the exogenously introduced factors are sufficient for reprogramming in combination but insufficient if less than the combination is expressed. Subcombinations of the exogenously introduced factors can be inducibly expressed, and candidate reprogramming agents, e.g., libraries of agents, can be screened for their ability to substitute for the missing factor(s).

In some embodiments of the invention the reprogramming agent is selected from genes encoding Oct-4, Sox-2, c-Myc, and Klf4 and/or the proteins themselves. In some embodiments at least 2, 3, or all of said agents are introduced into somatic cells. One aspect of the invention comprises method of identifying alternate reprogramming agents. For example, 3 of said agents can be introduced into cells, thereby rendering such cells susceptible to reprogramming. The cells are then used in an inventive screening method to identify a fourth agent or combination of agents that reprograms the cells to an ES-like state. In one embodiment, the method is used to identify an agent that substitutes for c-myc. In one embodiment, the method is used to identify an agent that substitutes for Klf4. In one embodiment, the method is used to identify an agent that substitutes for Sox2. In one embodiment, the method is used to identify an agent that substitutes for Oct-4. In some embodiments the methods are practiced using human cells and human analogs of the relevant factors are expressed. In some embodiments the cells are the engineered cells of the present invention that contain an endogenous pluripotency gene linked to a selectable marker.

Methods for Gene Identification

The present invention provides methods for identifying a gene that activates the expression of an endogenous pluripotency gene in somatic cells. The methods comprise: transfecting the somatic cells of the present invention with a cDNA library prepared from ES cells or oocytes, selecting for cells that express the first selectable marker, and assessing the expression of the first endogenous pluripotency gene in the transfected cells that express the first selectable marker. The expression of the first endogenous pluripotency gene indicates that the cDNA encodes a gene that activates the expression of an endogenous pluripotency gene in somatic cells.

The methods are applicable for identifying a gene that activates the expression of at least two endogenous pluripotency genes in somatic cells. The somatic cells used in the methods further comprise a second endogenous pluripotency gene linked to a second selectable marker. The methods are modified to select for transfected cells that express both selectable markers, among which the expression of the first and the second endogenous pluripotency genes are assessed. The expression of both the first and the second endogenous pluripotency genes indicates that the cDNA encodes a gene that activates the expression of at least two pluripotency genes in somatic cells.

The methods are further applicable for identifying a gene that activates the expression of at least three endogenous pluripotency genes in somatic cells. The somatic cells used in the methods further comprise a third endogenous pluripotency gene linked to a third selectable marker. The methods are modified to select for transfected cells that express all three selectable markers, among which the expression of all three endogenous pluripotency genes are assessed. The expression of all three endogenous pluripotency genes indicates that the cDNA encodes a gene that activates the expression of at least three pluripotency genes in somatic cells.

The practice of the present invention will employ, unless otherwise indicated, conventional techniques of mouse genetics, developmental biology, cell biology, cell culture, molecular biology, transgenic biology, microbiology, recombinant DNA, and immunology, which are within the skill of the art. Such techniques are described in the literature. See, for example, Current Protocols in Cell Biology, ed. by Bonifacino, Dasso, Lippincott-Schwartz, Harford, and Yamada, John Wiley and Sons, Inc., New York, 1999; Manipulating the Mouse Embryos, A Laboratory Manual, 3rd Ed., by Hogan et al., Cold Spring Contain Laboratory Press, Cold Spring Contain, New York, 2003; Gene Targeting: A Practical Approach, IRL Press at Oxford University Press, Oxford, 1993; and Gene Targeting Protocols, Human Press, Totowa, N.J., 2000.

Reprogrammed Somatic Cells and their Uses

The invention thus provides a number of significant advances that facilitate therapeutic uses of reprogrammed somatic cells including the following: (i) the ability to reprogram somatic cells lacking genetic modification to an ES-like state and select such reprogrammed cells from a population of cells that are not reprogrammed or are only partly reprogrammed to an ES-like state; and (ii) the recognition that stable reprogramming can be achieved by transient presence of reprogramming agents rather than requiring stable and ongoing expression or exposure to such agents. The first advance allows, among other things, the efficient derivation of ES-like cells from donor-specific somatic cells without requiring genetic modification for purposes of selection. The second advance allows, among other things, reprogramming using methods such as transient transfection (e.g., of nucleic acid constructs encoding a protein that contributes to reprogramming), protein transduction, and other methods of introducing agents into cells that neither require modification of the genome or the introduction of stably heritable genetic elements into the somatic cells. In summary, these advances open the possibility of obtaining donor-specific ES-like cells by reprogramming somatic cells without the use of genetic modification.

The present invention also provides reprogrammed somatic cells (RSCs), including reprogrammed pluripotent somatic cells (RPSCs), produced by the methods of the invention. These methods, useful for the generation of cells of a desired cell type, have wide range of applications. For one example, these methods have applications in livestock management, involving the precise genetic manipulation of animals for economic or health purposes. For another example, these methods have medical application in treating or preventing a condition.

Accordingly, the invention provides methods for the treatment or prevention of a condition in a mammal. In one embodiment, the methods start with obtaining somatic cells from the individual, reprogramming the somatic cells so obtained by methods of the present invention to obtain RPSCs. The RPSCs are then cultured under conditions suitable for development of the RPSCs into cells of a desired cell type. The developed cells of the desired cell type are harvested and introduced into the individual to treat the condition. In an alternative embodiment, the methods start with obtaining somatic cells from the individual, reprogramming the somatic cells so obtained by methods of the present invention. The RPSCs are then cultured under conditions suitable for development of the RPSCs into a desired organ, which is harvested and introduced into the individual to treat the condition. The condition may be any condition in which cell or organ function is abnormal and/or reduced below normal levels. Thus the invention encompasses obtaining somatic cells from a donor in need of cell therapy, subjecting the cells to a reprogramming agent such as contacting the cells with a reprogramming agent, selecting reprogrammed somatic cells according to a method of the invention. A donor in need of cell therapy may suffer from any condition, wherein the condition or one or more symptoms of the condition can be alleviated by administering cells to the donor and/or in which the progression of the condition can be slowed by administering cells to the donor.

The RPSCs in certain embodiments of the present invention are ES-like cells, and thus may be induced to differentiate to obtain the desired cell types according to known methods to differentiate ES cells. For example, the RPSCs may be induced to differentiate into hematopoietic stem cells, muscle cells, cardiac muscle cells, liver cells, pancreatic cells, cartilage cells, epithelial cells, urinary tract cells, nervous system cells (e.g., neurons) etc., by culturing such cells in differentiation medium and under conditions which provide for cell differentiation. Medium and methods which result in the differentiation of embryonic stem cells are known in the art as are suitable culturing conditions.

For example, Palacios et al., Proc. Natl. Acad. Sci., USA, 92: 7530-37 (1995) teaches the production of hematopoietic stem cells from an embryonic cell line by subjecting stem cells to an induction procedure comprising initially culturing aggregates of such cells in a suspension culture medium lacking retinoic acid followed by culturing in the same medium containing retinoic acid, followed by transferal of cell aggregates to a substrate which provides for cell attachment.

Moreover, Pedersen, J. Reprod. Fertil. Dev., 6: 543-52 (1994) is a review article which references numerous articles disclosing methods for in vitro differentiation of embryonic stem cells to produce various differentiated cell types including hematopoietic cells, muscle, cardiac muscle, nerve cells, among others.

Further, Bain et al., Dev. Biol., 168:342-357 (1995) teaches in vitro differentiation of embryonic stem cells to produce neural cells which possess neuronal properties. These references are exemplary of reported methods for obtaining differentiated cells from embryonic or stem-like cells. These references and in particular the disclosures therein relating to methods for differentiating embryonic stem cells are incorporated by reference in their entirety herein.

Thus, using known methods and culture medium, one skilled in the art may culture the subject embryonic or stem-like cells to obtain desired differentiated cell types, e.g., neural cells, muscle cells, hematopoietic cells, etc. In addition, the use of inducible Bcl-2 or Bcl-xl might be useful for enhancing in vitro development of specific cell lineages. In vivo, Bcl-2 prevents many, but not all, forms of apoptotic cell death that occur during lymphoid and neural development. A thorough discussion of how Bcl-2 expression might be used to inhibit apoptosis of relevant cell lineages following transfection of donor cells is disclosed in U.S. Pat. No. 5,646,008, which is herein incorporated by reference.

The subject RPSCs may be used to obtain any desired differentiated cell type. Therapeutic usages of such differentiated human cells are unparalleled. For example, human hematopoietic stem cells may be used in medical treatments requiring bone marrow transplantation. Such procedures are used to treat many diseases, e.g., late stage cancers such as ovarian cancer and leukemia, as well as diseases that compromise the immune system, such as AIDS. Hematopoietic stem cells can be obtained, e.g., by fusing adult somatic cells of a cancer or AIDS patient, e.g., epithelial cells or lymphocytes with an enucleated oocyte, e.g., bovine oocyte, obtaining embryonic or stem-like cells as described above, and culturing such cells under conditions which favor differentiation, until hematopoietic stem cells are obtained. Such hematopoietic cells may be used in the treatment of diseases including cancer and AIDS.

The methods of the present invention can also be used to treat, prevent, or stabilize a neurological disease such as Alzheimer's disease, Parkinson's disease, Huntington's disease, or ALS, lysosomal storage diseases, multiple sclerosis, or a spinal cord injury. For example, somatic cells may be obtained from the individual in need of treatment, and reprogrammed to gain pluripotency, and cultured to derive neurectoderm cells that may be used to replace or assist the normal function of diseased or damaged tissue.

For the treatment or prevention of endocrine conditions, RPSCs that produce a hormone, such as a growth factor, thyroid hormone, thyroid-stimulating hormone, parathyroid hormone, steroid, serotonin, epinephrine, or norepinephrine may be administered to a mammal. Additionally, reprogrammed epithelial cells may be administered to repair damage to the lining of a body cavity or organ, such as a lung, gut, exocrine gland, or urogenital tract. It is also contemplated that RPSCs may be administered to a mammal to treat damage or deficiency of cells in an organ such as the bladder, brain, esophagus, fallopian tube, heart, intestines, gallbladder, kidney, liver, lung, ovaries, pancreas, prostate, spinal cord, spleen, stomach, testes, thymus, thyroid, trachea, ureter, urethra, or uterus.

The present invention has the potential to provide an essentially limitless supply of isogenic or syngeneic human cells suitable for transplantation. Such a supply would obviate the significant problem associated with current transplantation methods, i.e., rejection of the transplanted tissue which may occur because of host versus graft or graft versus host rejection. Conventionally, rejection is prevented or reduced by the administration of anti-rejection drugs such as cyclosporin. However, such drugs have significant adverse side-effects, e.g., immunosuppression, carcinogenic properties, as well as being very expensive. The present invention may eliminate, or at least greatly reduce, the need for anti-rejection drugs, such as cyclosporine, imulan, FK-506, glucocorticoids, and rapamycin, and derivatives thereof.

RPSCs may also be combined with a matrix to form a tissue or organ in vitro or in vivo that may be used to repair or replace a tissue or organ in a recipient mammal. For example, RPSCs may be cultured in vitro in the presence of a matrix to produce a tissue or organ of the urogenital system, such as the bladder, clitoris, corpus cavernosum, kidney, testis, ureter, uretal valve, or urethra, which may then be transplanted into a mammal (Atala, Curr. Opin. Urol. 9(6):517-526, 1999). In another transplant application, synthetic blood vessels are formed in vitro by culturing reprogrammed cells in the presence of an appropriate matrix, and then the vessels are transplanted into a mammal for the treatment or prevention of a cardiovascular or circulatory condition. For the generation of donor cartilage or bone tissue, RPSCs such as chondrocytes or osteocytes are cultured in vitro in the presence of a matrix under conditions that allow the formation of cartilage or bone, and then the matrix containing the donor tissue is administered to a mammal. Alternatively, a mixture of the cells and a matrix may be administered to a mammal for the formation of the desired tissue in vivo. Preferably, the cells are attached to the surface of the matrix or encapsulated by the matrix. Examples of matrices that may be used for the formation of donor tissues or organs include collagen matrices, carbon fibers, polyvinyl alcohol sponges, acrylateamide sponges, fibrin-thrombin gels, hyaluronic acid-based polymers, and synthetic polymer matrices containing polyanhydride, polyorthoester, polyglycolic acid, or a combination thereof (see, for example, U.S. Pat. Nos. 4,846,835; 4,642,120; 5,786,217; and 5,041,138).

The RPSCs produced according to the invention may be used to produce genetically engineered or transgenic differentiated cells. Essentially, this will be effected by introducing a desired gene or genes, or removing all or part of an endogenous gene or genes of RPSCs produced according to the invention, and allowing such cells to differentiate into the desired cell type. A preferred method for achieving such modification is by homologous recombination because such technique can be used to insert, delete or modify a gene or genes at a specific site or sites in the stem-like cell genome.

This methodology can be used to replace defective genes, e.g., defective immune system genes, cystic fibrosis genes, or to introduce genes which result in the expression of therapeutically beneficial proteins such as growth factors, lymphokines, cytokines, enzymes, etc. For example, the gene encoding brain derived growth factor maybe introduced into human embryonic or stem-like cells, the cells differentiated into neural cells and the cells transplanted into a Parkinson's patient to retard the loss of neural cells during such disease. Examples of mutations that may be rescued using these methods include mutations in the cystic fibrosis gene; mutations associated with Dunningan's disease such as the R482W, R482Q, and R584H mutations in the lamin A gene; and mutations associated with the autosomal-dominant form of Emery Deyfuss muscular dystrophy such as the R249Q, R453W, and Q6STOP mutations in the lamin A gene. In the Q6STOP mutation, the codon for Gln6 is mutated to a stop codon.

Previously, cell types transfected with BDNF varied from primary cells to immortalized cell lines, either neural or non-neural (myoblast and fibroblast) derived cells. For example, astrocytes have been transfected with BDNF gene using retroviral vectors, and the cells grafted into a rat model of Parkinson's disease (Yoshimoto et al., Brain Research, 691:25-36, (1995)). This ex vivo therapy reduced Parkinson's-like symptoms in the rats up to 45% 32 days after transfer. Also, the tyrosine hydroxylase gene has been placed into astrocytes with similar results (Lundberg et al., Develop. Neurol., 139:39-53 (1996) and references cited therein).

However, such ex vivo systems have problems. In particular, retroviral vectors currently used are down-regulated in vivo and the transgene is only transiently expressed (review by Mulligan, Science, 260: 926-932 (1993)). Also, such studies used primary cells, astrocytes, which have finite life span and replicate slowly. Such properties adversely affect the rate of transfection and impede selection of stably transfected cells. Moreover, it is almost impossible to propagate a large population of gene targeted primary cells to be used in homologous recombination techniques.

By contrast, the difficulties associated with retroviral systems should be eliminated by the use of RPSCs of the present invention, which are ES-like cells. Using known methods to introduced desired genes/mutations into ES cells, RPSCs may be genetically engineered, and the resulting engineered cells differentiated into desired cell types, e.g., hematopoietic cells, neural cells, pancreatic cells, cartilage cells, etc. Genes which may be introduced into the RPSCs include, for example, epidermal growth factor, basic fibroblast growth factor, glial derived neurotrophic growth factor, insulin-like growth factor (I and II), neurotrophin3, neurotrophin-4/5, ciliary neurotrophic factor, AFT-1, cytokine genes (interleukins, interferons, colony stimulating factors, tumor necrosis factors (alpha and beta), etc.), genes encoding therapeutic enzymes, collagen, human serum albumin, etc.

In addition, it is also possible to use one of the negative selection systems now known in the art for eliminating therapeutic cells from a patient if necessary. For example, donor cells transfected with the thymidine kinase (TK) gene will lead to the production of embryonic (e.g., ES-like) cells containing the TK gene. Differentiation of these cells will lead to the isolation of therapeutic cells of interest which also express the TK gene. Such cells may be selectively eliminated at any time from a patient upon gancyclovir administration. Such a negative selection system is described in U.S. Pat. No. 5,698,446, and is herein incorporated by reference. In other embodiments the cells are engineered to contain a gene that encodes a toxic product whose expression is under control of an inducible promoter. Administration of the inducer causes production of the toxic product, leading to death of the cells. Thus any of the somatic cells of the invention may comprise a suicide gene, optionally contained in an expression cassette, which may be integrated into the genome. The suicide gene is one whose expression would be lethal to cells. Examples include genes encoding diphtheria toxin, cholera toxin, ricin, etc. The suicide gene may be under control of expression control elements that do not direct expression under normal circumstances in the absence of a specific inducing agent or stimulus. However, expression can be induced under appropriate conditions, e.g., (i) by administering an appropriate inducing agent to a cell or organism or (ii) if a particular gene (e.g., an oncogene, a gene involved in the cell division cycle, or a gene indicative of dedifferentiation or loss of differentiation) is expressed in the cells, or (iii) if expression of a gene such as a cell cycle control gene or a gene indicative of differentiation is lost. See, e.g., U.S. Pat. No. 6,761,884. In some embodiments the gene is only expressed following a recombination event mediated by a site-specific recombinase. Such an event may bring the coding sequence into operable association with expression control elements such as a promoter. The recombinase may be a different recombinase to that used to induce expression of the RNAi agent targeted to a DNA methyltransferase. Expression of the suicide gene may be induced if it is desired to eliminate cells (or their progeny) from the body of a subject after the cells (or their ancestors) have been administered to a subject. For example, if a reprogrammed somatic cell gives rise to a tumor, the tumor can be eliminated by inducing expression of the suicide gene. In some embodiments tumor formation is inhibited because the cells are automatically eliminated upon dedifferentiation or loss of proper cell cycle control.

Examples of diseases, disorders, or conditions that may be treated or prevented include neurological, endocrine, structural, skeletal, vascular, urinary, digestive, integumentary, blood, immune, auto-immune, inflammatory, endocrine, kidney, bladder, cardiovascular, cancer, circulatory, digestive, hematopoietic, and muscular diseases, disorders, and conditions. In addition, reprogrammed cells may be used for reconstructive applications, such as for repairing or replacing tissues or organs.

With respect to the therapeutic methods of the invention, it is not intended that the administration of RPSCs to a mammal be limited to a particular mode of administration, dosage, or frequency of dosing; the present invention contemplates all modes of administration, including intramuscular, intravenous, intraarticular, intralesional, subcutaneous, or any other route sufficient to provide a dose adequate to prevent or treat a disease. The RPSCs may be administered to the mammal in a single dose or multiple doses. When multiple doses are administered, the doses may be separated from one another by, for example, one week, one month, one year, or ten years. One or more growth factors, hormones, interleukins, cytokines, or other cells may also be administered before, during, or after administration of the cells to further bias them towards a particular cell type.

The RPSCs of the present invention may be used as an in vitro model of differentiation, in particular for the study of genes which are involved in the regulation of early development. Differentiated cell tissues and organs using the RPSCs may be used in drug studies.

Furthermore, the RPSCs produced according to the invention maybe introduced into animals, e.g., SCID mice, cows, pigs, e.g., under the renal capsule or intramuscularly and used to produce a teratoma therein. This teratoma can be used to derive different tissue types. Also, the inner cell mass produced by X-species nuclear transfer may be introduced together with a biodegradable, biocompatible polymer matrix that provides for the formation of 3-dimensional tissues. After tissue formation, the polymer degrades, ideally just leaving the donor tissue, e.g., cardiac, pancreatic, neural, lung, liver. In some instances, it may be advantageous to include growth factors and proteins that promote angiogenesis. Alternatively, the formation of tissues can be effected totally in vitro, with appropriate culture media and conditions, growth factors, and biodegradable polymer matrices.

Applications of the Somatic Cell Reprogramming Methods and RPSCs in Animals

The reprogramming methods disclosed herein may be used to generate RPSCs for a variety of animal species. The RPSCs generated can be useful to produce desired animals. Animals include, for example, avians and mammals as well as any animal that is an endangered species. Exemplary birds include domesticated birds (e.g., quail, chickens, ducks, geese, turkeys, and guinea hens) as well as other birds such as birds of prey (e.g., hawks, falcons, ospreys, condors, etc.), endangered birds (e.g., parrots, California condor, etc.), ostriches etc. Exemplary mammals include murine, caprine, ovine, bovine, porcine, canine, feline and primate. Of these, preferred members include domesticated animals, including, for examples, cattle, buffalo, pigs, horses, cows, rabbits, guinea pigs, sheep, and goats.

RPSCs generated by the reprogramming methods of the present invention allows one, for the first time, to genetically engineer animals for which ES cells are not available through other means. RPSCs are ES-like cells, and are thus amenable to genetic manipulation. To date, no ES cells are available for a wide variety of animals. As a result, for these animals, it is currently practically impossible to create genetically modified animals having targeted mutations. The ES-cell like RPSCs can be manipulated to introduce desired targeted genetic modifications. The resulting engineered RPSCs can then be used to generate a cloned animal with the desired genetic modifications in its germ line, using methods described for ES cells in mouse. See Capecchi and Thomas, U.S. Pat. Nos. 5,487,992, 5,627,059, 5,631,153, and 6,204,061. Genetic engineering in animals has potentially great applications in a variety of animals, especially farm animals.

The somatic cell reprogramming methods of the present invention provides at least two methods for delivering optimized farm animals. In the first, somatic cell reprogramming can be used to capture the best available phenotype for a farm animal stock. The current technologies used to deliver optimized farm animals are based on selective breeding, and expansion from preferred breeding stocks. Animals that have been selected on the basis of superior characteristics, including, for example, meat content, egg production (in the case of poultry), feed conversion ratio, are used to breed large numbers of animals that are in turn used in the human food supply. This traditional process has profound inherent inefficiencies. The phenotype observed in an individual animal is often only partially transmitted in the progeny of that animal. Therefore, traditional breeding schemes are inefficient in capturing the very best phenotype in all of the progeny animals. In contrast, the reprogramming methods of the present invention provides a controlled and efficient way to achieve the same goal, by generating RPSCs from somatic cells of an animal with the desired characteristics. The RPSCs generated may be used immediately to generate cloned animals derived from the RPSCs. Known methods for generating mice from ES cells can be used for this procedure. Alternatively, the RPSCs generated may be cryopreserved and thawed in response to a grower's needs.

In the second method, somatic cells from an animal with the desired characteristics are reprogrammed to produce RPSCs. The RPSCs are further genetically engineered to introduce desired genetic modification(s), before being placed into a recipient embryo to produce desired progeny.

The reprogramming methods can also be used to rescue endangered species. Somatic cell reprogramming provides an efficient method to generate RPSCs from somatic cells of an endangered animal. The resulting RPSCs can be used immediately to expand the numbers of the endangered animal. Alternatively, the RPSCs can be cryopreserved to generate a RPSC stock for the endangered species, as a safeguard measure against extinction of the endangered species.

The subject invention will be more particularly described with reference to the following non-limiting examples. All patents, patent applications and references cited herein are incorporated in their entirety by reference. In addition, the teachings of U.S. Provisional Application No. 60/525,612, filed Nov. 26, 2003, U.S. Provisional Application No. 60/530,042, filed Dec. 15, 2003, U.S. Provisional Patent Application No. 60/922,121, filed Apr. 7, 2007, and U.S. patent application Ser. No. 10/997,146, filed Nov. 24, 2004, are incorporated herein by reference.

EXAMPLES

Example 1

Methods
Cell Culture, MEF Isolation and Viral Infections

ES and iPS cells were cultivated on irradiated MEFs in DME containing 15% fetal calf serum, Leukemia Inhibiting Factor (LIF), penicillin/streptomycin, L-glutamine, and non-essential amino acids. All cells were depleted of feeder cells for two passages on 0.2% gelatin before RNA, DNA or protein isolation. Transgenic MEFs were isolated and selected in 2 µg/ml puromycin (Sigma) from E13.5 chimeric embryos following blastocyst injection of Oct4-inducible KH2 ES cells (Hochedlinger et al., Cell 121(3):465 (2005)) which had been previously targeted with either Oct4-IRES-GfpNeo or Nanog-neo constructs (Mitsui et al., Cell 113(5): 631 (2003)). $2 \times 10^5$ MEFs at passage 3-4 were infected overnight with pooled viral supernatant generated by transfection of HEK293T cells (Eugene, Roche) with the Moloney-based retroviral vector pLIB (Clontech) containing the cDNAs of Oct4, Sox2, Klf4 and c-Myc together with the packaging plasmid pCL-Eco (Naviaux et al., J Virol 70(8): 5701 (1996)).

Southern Blot, Methylation and Chromatin Analysis

To assess the levels of DNA methylation, genomic DNA was digested with HpaII, and hybridized to pMR150 as a probe for the minor satellite repeats (Chapman et al., Nature 284 (1984)), or with an IAP-probe (Walsh at al., Nat Genet 20(2):116 (1998)). Bisulfite treatment was performed with the Qiagen EpiTect Kit. For the methylation status of Oct4 and Nanog promoters bisulfite sequencing analysis was performed as described previously (Blelloch et al., Stem Cells 24(9):2007 (2006)). 10-20 clones of each sample were sequenced in both directions. For imprinted genes, a COBRA assay was performed. PCR primers and conditions were as described previously (Lucifero at al., Genomics 79(4):530 (2002)). PCR products were gel purified, digested with BstUI or HpyCH4 IV and resolved on a 2% agarose gel. The status of bivalent domains was determined by chromatin immunoprecipitation followed by quantitative PCR analysis as described before (Boyer at al., Nature 441:349 (2006)).

Expression Analysis 50 ng of total RNA isolated using TRIzol reagent (Invitrogen) was reverse transcribed and quantified using QuantTtect SYBR green RT-PCR Kit (Qiagen) on a 7000 ABI detection system. Western blot and immunofluorescence analysis was performed as described (Hochedlinger et al., *Cell* 121(3):465 (2005); Wernig et al., *J. Neurosci* 24(22): 5258 (2004)). Primary antibodies included Oct4 (monoclonal mouse, Santa Cruz), Nanog (polyclonal rabbit, Bethyl), actin (monoclonal mouse, Abcam), SSEA1 (monoclonal mouse, Developmental Studies Hybridoma Bank). Appropriately labeled secondary antibodies were purchased from Jackson Immunoresearch. Microarray targets from 2 µg total RNA were synthesized and labeled using the Low RNA Input Linear Amp Kit (Agilent) and hybridized to Agilent whole mouse genome oligo arrays (G4122F). Arrays were scanned on an Agilent G2565B scanner and signal intensities were calculated in Agilent FE software. Datasets were normalized using a R script and clustered as previously described (Brambrink et al., *Proc Natl Aced Sci USA* 103 (4):933 (2006)). Microarray datasets were submitted to the ArrayExpress database.

Results

Oct4-Induced Fibroblasts are More Susceptible to Reprogramming than Uninduced Fibroblasts as Demonstrated by Nuclear Transfer Experiment A. Generation of Transgenic Mouse Carrying an Inducible Oct4 Transgene An inducible Oct4 allele was constructed as follows: first, two integration vectors are constructed. The first integration vector, inducible Oct4 integration vector, contains an Oct4 gene driven by a tetracycline-inducible promoter (Tet-Op). The Tet-Op-Oct4 cassette is flanked by a splice-acceptor double poly-A signal (SA-dpA) at its 5' end and a SV40 polyA tail (SV40-pA) at its 3' end. The second integration vector, tetracycline activator integration vector, contains a mutant form of tetracycline activator, M2-rtTA, which is more responsive to doxycycline (Dox) induction than the wild type activator. (Urlinger et al., *Proc Natl Acad Sci USA* 97(14):7963 (2000)).

The two integration vectors are introduced into V6.5 ES cells: the inducible Oct4 integration vector and the tetracycline activator integration vector are introduced into the Collagen locus and the Rosa26 locus respectively via site-specific integration, as shown in FIG. 1. The resulting ES cells are used to make Oct4-inducible mice by tetraploid complementation.

B. Expression of the Inducible Oct4 Transgene

Fibroblasts derived from tail biopsies of the Oct4-inducible mice were cultured. A fraction of the cultured fibroblasts were induced with doxycycline for 3 days (at 2 microgram/ml), and Oct4 expression was detected by Northern blot and Western blot analysis. The Oct4 expression level in fibroblasts treated with doxycycline is comparable to the Oct4 expression level in ES cells, and undetectable in fibroblasts not treated with doxycycline. The expression results demonstrate that the inducible Oct4 transgene is expressed as planned.

C. Nuclear Transfer Experiment

Nuclear transfer was performed on fibroblasts derived from tail biopsies of mice that carry the inducible Oct4 transgene. Dox induction was for 24 hours prior to nuclear transfer. Cloned embryos were then activated and cultured to the blastocyst stage to derive ES cells as described previously (Hochedlinger and Jaenisch, *Nature* 415:1035 (2002)). On average, blastocyst formation and ES cell derivation (as measured as a fraction of eggs with pronucleus formation) is more efficient from Oct4-induced fibroblast than from uninduced fibroblasts. This result demonstrated that induced Oct4 expression in somatic cells such as fibroblasts make these cells more susceptible to reprogramming.

Selection of ES-Like Cells by Stringent Criteria

Figure 2A:
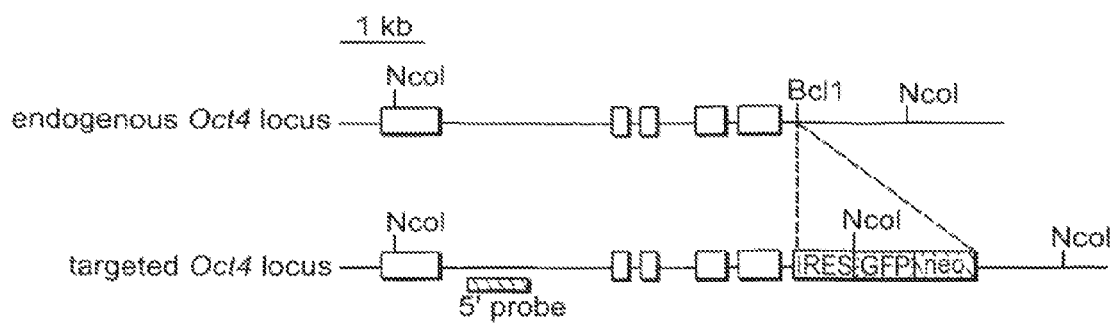
FIGS. 2A-2B show the generation of Oct4- and Nanog-selected iPS cells.
Figure 2B:
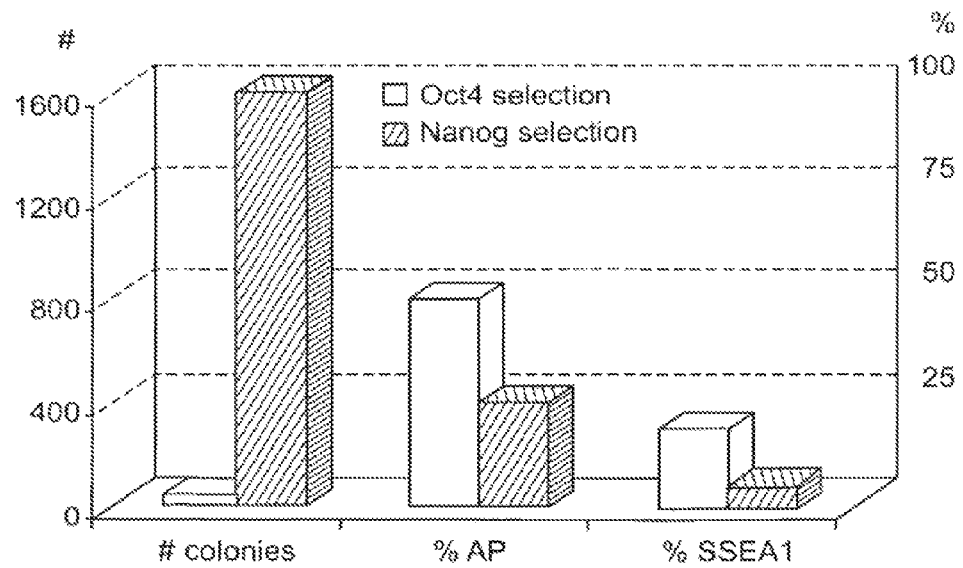

Using homologous recombination in ES cells, we generated mouse embryonic fibroblasts (MEFs) that carried a neomycin resistance marker inserted into either the endogenous Oct4 (Oct4-neo) or Nanog locus (Nanog-neo) (FIG. 2A). These cultures were sensitive to G418, indicating that the Oct4 and Nanog loci were, as expected, silenced in somatic cells. Five days after infection with Oct4-, Sox2-, c-Myc- and Klf4-expressing retroviral vectors the cells were passaged, and G418 was added to the cultures to select for drug resistant cells. Resistant colonies appeared in both the Nanog-neo and the Oct4-neo cultures, though with a very different efficiency: the number of drug resistant colonies in the Nanog-neo cultures was 35 fold higher than in the Oct4-neo cultures (FIG. 2B). When the colonies were stained for alkaline phosphatase (AP) or SSEA1, a significantly higher fraction of the Oct4-neo colonies was positive and showed an ES cell like morphology. This suggests that although the Nanog locus was easier to activate, a higher fraction of the drug resistant colonies in Oct4-neo cultures were reprogrammed to a pluripotent state. Consistent with this notion, out of 12 randomly picked Oct4-neo colonies, ten continued to proliferate and maintain an ES-like phenotype, and three of these displayed strong AP activity and SSEA1 expression. In contrast, all nine continuously proliferating Nanog-neo colonies had a flat or small and round-shaped appearance, and the rare ES cell-resembling colonies were only partially labeled with SSEA1 antibodies. However, after careful morphological selection of colonies from both selection strategies based on criteria known in the art to be characteristic of ES cells, we were able to propagate ES-like clones (designated as iPS cells for "induced pluripotent cells") which displayed homogenous Nanog, SSEA1 and AP expression and formed undifferentiated colonies when seeded at clonal density on gelatin-coated dishes.

Characterization of Gene Expression and DNA Methylation in iPS Cells

To characterize the reprogrammed cells on a molecular level, we used quantitative RT-PCR (qRT-PCR) to measure expression of ES cell and fibroblast-specific genes. Oct4-neo-selected iPS cells expressed endogenous Nanog and Oct4 at similar levels as ES cells, whereas MEFs did not express either gene. Using specific primers to distinguish endogenous from viral Sox2 transcripts showed that the vast majority of Sox2 transcripts originated from the endogenous locus. In contrast, HoxA9 and Zfpm2 were highly expressed in MEFs but at very low levels in iPS or ES cells. Western analysis showed similar Nanog and Oct4 protein levels in iPS and ES cells. Finally, we used microarray technology to compare gene expression patterns on a global level. The iPS cells clustered with ES cells in contrast to wild type or donor MEFs.

To investigate the DNA methylation level of Oct4 and Nanog promoters, we performed bisulfite sequencing and COBRA analysis with DNA isolated from ES cells, iPS cells and MEFs. Both loci were demethylated in ES and iPS cells and fully methylated in MEFs. To assess whether the maintenance of genomic imprinting was compromised, we assessed the methylation status of four imprinted genes H19, Peg1, Peg3 and Snrpn. Bands corresponding to an unmethylated and methylated allele were detected for each gene in MEFs, iPS cells and tail tip fibroblasts. In contrast, EG cells, which have erased all imprints (Labosky et al., *Development* 120(11):3197 (1994)), were unmethylated. Our results indicate that the epigenetic state of the Oct4 and Nanog genes was reprogrammed from a transcriptionally repressed (somatic) state to an active (embryonic) state and that the pattern of somatic imprinting was maintained in iPS cells.

Recently, downstream target genes of Oct4, Nanog and Sox2 have been defined in ES cells by genome wide location analyses (Boyer et al., Nat Genet 38(4):431 (2006)). These targets include many important developmental regulators, a proportion of which are also bound and repressed by the PcG complexes PRC1 and PRC2 (Lee et al., Cell 125(2):301 (2006); Boyer et al., Nature 441(7091):349 (2006)). Notably, the chromatin at many of these non-expressed target genes adopt a bivalent conformation in ES cells, carrying both the "active" histone H3 lysine 4 (H3K4) methylation mark and the "repressive" histone H3 lysine 27 (H3K27) methylation mark (Bernstein et al., Cell 125(2): 315 (2006); Azuara et al., Nat Cell Biol 8(5):532 (2006)). In differentiated cells, those genes tend to instead carry either H3K4 or H3K27 methylation marks depending on their expression state.

We used chromatin immunoprecipitation (ChIP) and real-time PCR to quantify H3K4 and H3K27 methylation for a set of genes reported to be bivalent in pluripotent ES cells (Bernstein et al., Cell 125(2): 315 (2006)). In the MEFs, the expressed genes Zfpm2 and HoxA9 carry strong H3K4 methylation, but weaker or no H3K27 methylation, whereas Nkx2.2, Sox1, Lbx1h, Pax5 and Evx1 predominantly carry H3K27 methylation. When analyzing Oct4-neo iPS cells, however, we found at each of these genes a bivalent conformation with both histone modifications like in normal ES cells (Bernstein et al., Cell 125(2): 315 (2006)). Identical results were obtained in several iPS clones selected from Oct4-neo and Nanog-neo fibroblasts.

iPS Cells are Resistant to Global Demethylation

Tolerance of genomic demethylation is a unique property of ES cells as somatic cells undergo rapid apoptosis upon loss of the methyltransferase. We investigated whether iPS cells would be resistant to global demethylation after Dnmt1 inhibition and would be able to re-establish global methylation patterns after restoration of Dnmt1 activity. To this end, we utilized a conditional lentiviral vector containing a Dnmt1 targeting shRNA and a GFP reporter gene (Ventura at al., Proc Natl Acad Sci USA 101(28):10380 (2004)). Infected iPS cells were plated at low density and GFP-positive colonies were picked and expanded. Southern analysis using HpaII digested genomic DNA showed that global demethylation of infected iPS cells was similar to Dnmt1−/− ES in contrast to uninfected iPS cells or MEFs, which displayed normal methylation levels.

Morphologically, the GFP-positive cells were indistinguishable from the parental line or from uninfected sister subclones indicating that iPS cells tolerate global DNA demethylation. In a second step, the Dnmt1 shRNA was excised through Cre-mediated recombination and normal DNA methylation levels were restored as has been reported previously for ES cells (Holm et al., Cancer Cell 8(4):275 (2005)). These observations show the functional reactivation of the de novo methyltransferases Dnmt3a/b in iPS cells (Okano at al., Cell 99:247 (1999)). As expected, the imprinted genes Snrpn and Peg3 were unmethylated and resistant to remethylation.

Retroviral Vectors are Silenced by De Novo Methylation in iPS Cells

Southern analysis indicated that the Oct4-neo iPS clone 18 carried 4-6 copies of the Oct4, c-Myc and Klf4 and only 1 copy of Sox2 retroviral vectors. Because these four factors were under the control of the constitutively expressed retroviral LTR, it was unclear in a prior study why iPS cells could be induced to differentiate (Takahashi and Yamanaka, Cell 126 (4):663 (2006)). To address this question, we designed primers specific for the 4 viral-encoded factor transcripts and compared expression levels by qRT-PCR in MEFs 2 days after infection, in iPS cells, in embryoid bodies (EB) derived from iPS cells and in demethylated and remethylated iPS cells. Although the MEFs represented a heterogenous population composed of uninfected and infected cells, viral dependent Oct4, Sox2, c-Myc and Klf4 RNA levels were 5-fold lower in iPS cells than in the infected MEFs, suggesting silencing of the viral LTR by de novo methylation upon reprogramming of the MEFs. Consistent with this conclusion is the fact that the total Sox2 and Oct4 RNA levels in iPS cells was similar to that in wild type (wt) ES cells and that the Sox2 transcripts in iPS cells were mostly, if not exclusively, transcribed from the endogenous gene. Upon differentiation to EBs, both viral and endogenous transcripts were downregulated. Importantly, all viral Sox2, Oct4 and Klf4 transcripts were about 2-fold upregulated in Dnmt1 knock down iPS cells and again downregulated following restoration of Dnmt1 activity. In contrast, transcript levels of c-Myc were about 20-fold lower in iPS cells than in infected MEFs and did not change upon differentiation of demethylation. Our results suggest that the retroviral vectors are subject to silencing by de novo methylation upon reprogramming of the fibroblasts.

iPS Cells have Similar Developmental Potential as ES Cells

We determined the developmental potential of iPS cells by teratoma and chimera formation. Histological analysis of tumors formed 3 weeks following subcutaneous injection of iPS cells into SCID mice revealed that the cells had differentiated into various cell types representing all three embryonic germ layers. Importantly, Oct4 and Nanog were only expressed in cells that appeared undifferentiated but were silenced in differentiated cells as in teratomas resulting from the injection of wt ES cells. To more stringently assess the developmental potential of iPS cells, GFP-labeled subclones were injected into diploid (2N) or tetraploid (4N) blastocysts. Injection of cells into 4N blastocysts is the most rigorous test for developmental potency, as the resulting embryo is composed only of the injected donor cells ("all ES embryo"). iPS cells derived from Oct4-neo and Nanog-neo MEFs could generate "all iPS embryos." Injection of iPS cells into 2N blastocysts efficiently generated high-contribution prenatal and viable postnatal chimeras. These findings indicate that iPS cells can contribute to all lineages of the embryo and thus have a similar developmental potential as ES cells.

The results presented in Example 1 confirm that the four transcription factors Oct4, Sox2, c-Myc and Klf4 can induce epigenetic reprogramming of a somatic genome to an embryonic state though with low efficiency. These four factors were initially identified based on their ability to induce expression of the Fbx15 gene in somatic cells. Fbx15 is specifically expressed in mouse ES cells and early embryos but is dispensable for maintenance of pluripotency and mouse development (Takahashi and Yamanaka, Cell 126(4):663 (2006)). In contrast to cells selected based on their expression of Fbx15, fibroblasts that had reactivated the endogenous Oct4 (Oct4-neo) or Nanog (Nanog-neo) loci grew feeder independently, expressed normal Oct4, Nanog and Sox2 RNA and protein levels, were epigenetically identical to ES cells by a number of criteria and were able to generate viable chimeras. Transduction of the 4 factors generated 35-fold more drug resistant cells from Nanog-neo than from Oct4-neo fibroblasts but a higher fraction of Oct4-selected cells exhibited all characteristics of pluripotent ES cells that were assessed.

The data presented above suggests that the pluripotent state of iPS cells is induced by the virally-transduced factors but is largely maintained by the activity of the endogenous pluripotency factors including Oct4, Nanog and Sox2 because the viral controlled transcripts, though expressed highly in MEFs, become mostly silenced in iPS cells. The total levels of Oct4, Nanog and Sox2 were similar in iPS and wt ES cells. Consistent with the conclusion that the pluripotent state is maintained by the endogenous pluripotency genes is the fact that the Oct4 and the Nanog genes become hypomethylated in IFS as in ES, and that the bivalent histone modifications of developmental regulators was reestablished. Importantly, iPS cells were resistant to global demethylation induced by inactivation of Dnmt1 similar to ES cells and in contrast to somatic cells. Re-expression of Dnmt1 in the hypomethylated ES cells resulted in global remethylation indicating that the iPS cells had also reactivated the de novo methyltransferases Dnmt3a/b. All these observations are consistent with the conclusion that the iPS cells have gained an epigenetic state that is similar to that of normal ES cells.

Expression of the 4 factors proved to be a robust method to induce reprogramming of somatic cells to a pluripotent state. One object of the present invention is to provide new ways to identify small molecules that reprogram cells without gene transfer of potentially harmful genetic material.

Example 2

Methods

Cell Culture, MEF Isolation and Viral Infections

ES and iPS cells were cultivated on irradiated MEFs in DME containing 15% fetal calf serum, Leukemia Inhibiting Factor (LIF), penicillin/streptomycin, L-glutamine, beta-mercaptoethanol and non-essential amino acids. All cells were depleted of feeder cells for two passages on 0.2% gelatin before RNA, DNA or protein isolation. $2 \times 10^5$ MEFs at passage 3-4 were infected overnight with pooled viral supernatant generated by transfection of HEK293T cells (Fugene, Roche) with the Moloney-based retroviral vector pLIB (Clontech) containing the cDNAs of Oct4, Sox2, Klf4 and c-Myc together with the packaging plasmid pCL-Eco (Naviaux et al., J Virol 70:5701 (1996)).

Blastocyst Injection

Diploid or tetraploid blastocysts (94-98 hours post HCG injection) were placed in a drop of DMEM with 15% PCS under mineral oil. A flat tip microinjection pipette with an internal diameter of 12-15 mm was used for ES cell injection. A controlled number of ES cells were injected into the blastocyst cavity. After injection, blastocysts were returned to KSOM media and placed at 37° C. until transferred to recipient females.

Recipient Females and Caesarean Sections

Ten to fifteen injected blastocysts were transferred to each uterine horn of 2.5 days postcoitum pseudopregnant B6D2F1 females. To recover full-term ES or chimeric pups, recipient mothers were sacrificed at 19.5 days postcoitum. Surviving pups were fostered to lactating BALE/c mothers.

Viral Integrations

Genomic DNA was digested with SpeI overnight, followed by electrophoresis and transfer. The blots were hybridized to the respective radioactively labeled cDNAS.

Immunohistochemistry

Cells were fixed in 4% paraformaldehyde for 10 min at room temperature, washed 3 times with PBS and blocked for 15 min with 5% FBS in PBS containing 0.1% Triton. After incubation with primary antibodies against Sox2 (monoclonal mouse, R&D Systems), Oct4 (monoclonal mouse, Santa Cruz), c-myc (polyclonal rabbit, Upstate), Nanog (polyclonal rabbit, Bethyl) and SSEA1 (monoclonal mouse, Developmental Studies Hybridoma Bank) for 1 hour cells were washed 3 times with PBS and incubated with fluorophore-labeled appropriate secondary antibodies purchased from Jackson Immunoresearch. Specimen were analyzed on an Olympus Fluorescence microscope and images were acquired with a Zeiss Axiocam camera.

Results

Reprogramming of Somatic Cells without Genetic or Chemical Selection

As described above, in vitro reprogramming of somatic cells into a pluripotent ES cell-like state has been achieved through retroviral transduction of Oct4, Sox2, c-myc and Klf4 into murine fibroblasts. In these experiments the rare "induced Pluripotent Stem" (iPS) cells were isolated by stringent selection for activation of a neomycin resistance gene inserted into the endogenous Oct4 or Nanog loci. Direct isolation of pluripotent cells from cultured somatic cells is of potential therapeutic interest but in order to translate such methods to non-murine, e.g., human, systems it would be desirable to develop alternatives to the requirement for transgenic donors used in the iPS isolation protocol described above. Here we demonstrate for the first time that reprogrammed pluripotent cells can be isolated from genetically unmodified somatic donor cells solely based upon morphological criteria. Thus, for example, genetically unmodified somatic donor cells can be obtained from a mouse, a rat, a rabbit, a farm animal, a companion animal, a primate or a human, and reprogrammed pluripotent cells can be derived from these donor cells.

Somatic cell nuclear transfer and cell fusion with embryonic stem (ES) cells have been well-established approaches to achieve reprogramming of somatic nuclei into a pluripotent state. Direct in vitro isolation of pluripotent ES-like cells from cultured somatic cells was achieved recently by transduction of the four transcription factors Oct4, Sox2, Klf4 and c-myc (below referred to as "factors") into genetically modified fibroblasts. The selection for the rare reprogrammed induced Pluripotent Stem (iPS) cells was based upon the reactivation of the Fbx15 (Takahashi and Yamanaka, Cell 226:663 (2006)) or the Oct4 or Nanog genes, all of which carried a drug resistance marker inserted into the respective endogenous loci by homologous recombination or a transgene containing the Nanog promoter. While iPS cell isolation based upon Fbx15 activation yielded cells that were pluripotent, they differed from ES cells at the molecular level and were unable to generate live chimeras. In these experiments selection was initiated at 3 days after viral transduction. In contrast, selection for Oct4 or Nanog activation produced pluripotent iPS cells that were epigenetically and biologically indistinguishable from normal ES cells. Reprogramming to pluripotency was, however, a slow and gradual process involving the sequential activation of the ES cell markers alkaline phosphatase (AP), SSEA1 and Nanog over a period of 2-4 weeks after factor transduction. Thus, when G418 was added to cultures of Oct4-neo or Nanog-neo fibroblasts at 3 days after factor transduction, no drug resistant colonies were formed, whereas addition of drug at 1 week generated a few and addition at 2 weeks significantly more drug resistant and reprogrammed colonies. The inverse relationship between the time of drug selection after factor transduction and the number of drug resistant iPS cells is consistent with the notion that the process of reprogramming involves multiple stochastic events that convert the epigenetic state of a somatic to that of a pluripotent cell.

In the present Example we show that pluripotent iPS cells can be derived from normal, genetically unmodified donor cells. In the first set of experiments we used a GFP marker inserted into the Oct4 locus to monitor the reprogramming process. Mouse embryonic fibroblasts (MEFs) carrying an IRES-EGFP cassette in the Oct4 locus were transduced with the four factors Oct4, Sox2, c-myc and Klf4 by retrovirus-mediated gene transfer as described before. Three days after infection the fibroblasts became morphologically more diverse than uninfected control cells and foci of increased growth appeared. On day 6, small tightly packed and sharp-edged colonies developed resembling ES cell colonies. During the following days these colonies continued to grow into large and more heterogeneous cell aggregates with some sectors resembling ES cell-like growth while more small and tight colonies continued to appear.

Eight of these large colonies were picked on day 11 and ten additional colonies were picked on day 16 based solely upon their morphology. When examined under the fluorescence microscope no GFP expression was detectable at day 11 and only one of the ten colonies picked on day 16 showed weak GFP expression. One of the eight colonies picked on day 11 and four of the ten colonies picked on day 16 gave rise to homogenous, ES-like cell lines. All five lines initiated Oct4-EGFP expression within 1-3 passages (Table 1) and displayed homogenous AP activity as well as SSEA1 and Nanog expression as would be expected for fully reprogrammed iPS cells.

Of the remaining colonies that had been picked initially based on morphological criteria, ten gave rise to heterogeneous cultures containing mainly fibroblast-like cells interspersed with a few ES-like colonies (Table 1). We investigated whether these heterogeneous cultures would yield additional iPS cell lines upon further passaging. For this we picked three ES-like colonies from each of five mixed cultures derived from the initial outgrowths and successfully established five additional iPS cell lines within 2-3 passages (Tables 1 and 2). In order to test whether the observed heterogeneity was a result of partly incomplete reprogramming or a contamination of not reprogrammed fibroblasts, we FACS-sorted the GFP positive and negative cells from clone #5 and the heterogenous subclone #5.2 and compared proviral integration patterns using southern blot analysis. The results indicated that the two cell populations are derived from the same parental cell indicating the requirement of further epigenetic events. From the picked subclones that did not generate secondary iPS lines, three subclones (6.1, 6.2 and 6.3; see Table 1 and 2) displayed an altered morphology (small cells, tightly grown colonies) but remained Oct4-GFP negative over multiple passages and displayed no staining for AP, SSEA1 or Nanog, suggesting that these cells were not pluripotent. The occurrence of ES marker negative cells was rare and these cells displayed subtle morphological differences from ES or true iPS cells such as the shape of colony boundaries. Because the cells were infected with all four retroviruses, it is possible that the four factors may not have been expressed at the right levels, giving rise to transformed rather than pluripotent cells. For example, high c-myc/Klf4 and insufficient Oct4/Sox2 expression may lead to rapidly growing non-iPS cells consistent with the notion that the role of Oct4 and Sox2 in the reprogramming process may be the suppression of the c-myc and Klf4 transformed phenotype (Yamanaka, Stem Cells 1:39-49 (2007)).

All iPS cell lines tested showed GFP intensity comparable to the Oct4-GFP ES cells consistent with our previous observation that Oct4 protein levels were similar in different iPS cell lines (Wernig, 2007). To analyze whether the iPS cells isolated by morphological criteria remained phenotypically stable over time, GFP fluorescence was monitored after multiple passages. These results show that the iPS cells exhibited non-variable and robust Oct4-GFP expression up to at least nine passages. These data clearly demonstrate that stable iPS lines can be efficiently derived without relying on drug selection.

We used the fraction of virus infected input cells and the number of ES cell-like colonies to estimate the efficiency of reprogramming. In a typical experiment about 100,000 cells were exposed to virus. Using staining for Sox2, Oct4 and c-myc as criterion we estimated about 10.2% of the cells were infected with all four virus generating 115 ES cell-like colonies. The efficiency for deriving iPS cells from the number of picked colonies was 44%. Thus, the overall efficiency of reprogramming was extrapolated to be about 0.5%.

Finally, we evaluated the developmental potency of non-selected iPS cells by teratoma formation, and injections into diploid (2N) and tetraploid (4N) blastocysts (Table 3) (Eggan at al., Proc Natl Acad Sci USA 98:6209-6214 (2001)). Three weeks after subcutaneous injection into SCID mice, lines 8.1 and 14 developed tumors which contained tissue types from all three germ layers determined by histological analysis. Following injection into 2N blastocysts, we generated live postnatal animals with high coat color chimerism. Importantly, when injected into 4N blastocysts, which is the most stringent test for developmental potency, live E14.5 embryos could be recovered (Table 4). These data demonstrate that screening for iPS cells based upon morphological criteria rather than selection for drug resistance can generate pluripotent iPS cells that display a similar biological potency as ES cells.

Derivation of iPS Cells from Genetically Unmodified Donor Cells

In the experiments described above, the Oct4-GFP marker was used to monitor the reprogramming process but not to screen for reprogrammed iPS cells. To assess whether iPS cells can be derived from genetically unmodified donor cells, we generated wild type MEFs from Balb/c and 129SvJae/C57Bl6(F1) mice and adult tailtip fibroblasts from 129SvJae/C57Bl6 (F1) and C57Bl6/DBA (F1) 2-3 month old mice. The cells were infected with retroviruses encoding the four factors and large colonies were picked at day 16 or later as described above. As in the previous experiments ES-like colonies became visible within one passage after picking of the primary colonies. Upon continued passaging or through subcloning we readily established homogenous cell lines with ES cell morphology and growth properties.

Assuming that reprogrammed cells outgrow the donor fibroblasts, we attempted to generate iPS cells by passaging the entire plate instead of picking colonies following morphological criteria. Many small colonies perfectly resembling ES cell colonies appeared within several days after the first passage of infected cell populations and 5 out 6 picked colonies grew into stable iPS lines (Table 3), After 2-3 passages using either direct picking or passaging the whole plate followed by picking of individual colonies we established one or more iPS lines from each background (Table 3). All genetically unmodified iPS lines expressed AP, SSEA1 and Nanog. In addition we generated chimeric embryos from Balb/c and 129/B6 MEF derived iPS lines, demonstrating that iPS cells from genetically unmodified fibroblasts are pluripotent (Table 4). It should be noted, however, that passaging of the factor transduced cell populations, while representing a simplified isolation protocol, cannot exclude that individual iPS cell lines may have been derived from the same reprogrammed parental cell.

Our results suggest that in vitro reprogramming of fibroblasts occurs frequently enough be detected in cultures of non-transgenic donor cells and is stable without selective pressure to express Oct4 or Nanog. Thus, the four factor-induced reprogramming can be applied to wild type cells. Without being bound by any theory, it appears that ectopic expression of Oct4, Sox2, c-myc and Klf4 initiates a gradual reprogramming process in multiple infected cells that ultimately leads to pluripotency over a time period of several weeks. Using Oct4 GFP MEFs to monitor reactivation of the endogenous Oct4 locus we found that all colonies but one were GFP-negative at the time of picking (see Table 2) and became GFP positive only after several passages. This suggests that reprogramming is a slow process involving the sequential activation of ES cell markers such as AP, SSEA1 and Nanog with Oct4 activation representing one of the last epigenetic events in the process. Also, these observations are consistent with our previous finding that the numbers of reprogrammed colonies were lower when drug selection for Oct4 activation was applied early after viral transduction, but was significantly higher when drug selection was initiated later. Finally, the slow reprogramming process induced by factor transduction may explain why the drug selection for Fbx15 activation as early as 3 days after infection as used in the initial iPS isolation protocol yielded only cells that had undergone incomplete epigenetic reprogramming. Our results predict that selection for Fbx15 activation at later times would generate iPS cells that are similar to iPS cells selected for Oct4 activation or isolated based on morphological criteria.

Example 3

Methods

Cell Culture and Viral Infections.

ES and established iPS cells were cultured on irradiated MEFs in DME containing 15% FCS, leukemia inhibiting factor (LIF), penicillin/streptomycin, L-glutamine, beta-mercaptoethanol and nonessential amino acids. MEFs used to derive primary iPS lines by infections with inducible lentiviruses were harvested at 13.5dpc from F1 matings between ROSA26-M2rtTA mice (Beard et al., 2006) and Nanog-GFP mice (Brambrink et al., 2008). Mouse C/EBPα cDNA was cloned into EcoRI cloning site of pLib, MSCV-Neo and pMig retroviral vectors. pMXs vectors encoding ES pluripotency genes were previously described (Takahashi and Yamanaka, 2006). Lentiviral preparation and infection with Doxycycline-inducible lentiviruses encoding Oct4, Klf4, c-Myc and Sox2 cDNA driven by the TetO/CMV promoter were previously described (Brambrink, 2008). Retrovirus stocks were prepared by transient transfection of Phoenix-Eco cells using Fugene (Roche), and supernatants were harvested 48 hr later. For infection, purified B cell subsets were resuspended in IMDM with 15% FCS as well as IL-4, IL-7, Flt-3L, SCF (10 ng/ml each, Peprotech), anti-CD40 (0.1 µg/ml, BD-Biosciences), BPS (10 ng/ml, Sigma-Aldrich) and Dox (4 µg/ml). Then, 2 ml aliquots were plated onto a 24-well plate precoated with retronectin (Takara) followed by 2 ml of retrovirus supernatant to which polybrene (Sigma) was added (8 µg/ml). The plates were incubated at 37° C. for 2 hours, and afterward 1 ml of viral supernatant was replaced with B cells resuspended in the cytokine-conditioned media described above. Plates were centrifuged for 90 min at 900 RPM and than incubated 24 hours at 37° C. 5% $CO_2$. Infected cells were then transferred onto OP9 bone marrow stromal cells line (ATCC) in fresh cytokine and Dox-supplemented media. After 14 days on Dox, colonies were picked and cultured on MEF feeder cells in ES media (without hematopoietic cytokines or Dox) and in the presence of puromycin (2 µg/ml) to eliminate any remaining OP9 cells.

V(D)J Rearrangement Analysis.

IgH, Igκ and Igλ rearrangements were amplified by PCR using degenerate primer sets as previously described (Chang et al., 1992; Cobaleda et al., 2007a; Schlissel at al., 1991) (Table 2). To characterize individual V-DJ rearrangements, the PCR fragments were cloned in TOPO vector, and at least 5 clones corresponding to the same PCR fragment were sequenced. Obtained sequences were analyzed with DNA-PLOT search engine (found at www.dnaplot.de). V-DJ and D-J rearrangements at the Igh locus were detected by Southern blot analysis on genomic DNA of the indicated iPS lines digested with EcoRI and using a 3'JH4 probe (1.6-kb HindIII-EcoRI fragment of plasmid JH4.3) (Alt et al., 1981). Vκ-Jκ rearrangements at the Igk locus were determined by Southern blot analysis of BamHI-digested genomic DNA using a 3'Jκ5 probe (1-kb XbaI-EcoRV fragment of plasmid pBS-JκMAR) (Lewis et al., 1982).

DNA Methylation and Histone Marks Analysis.

For the methylation status of Oct4 and Nanog promoters, bisulphite sequencing analysis was performed as described previously (Wernig et al., 2007). A total of 10-20 clones of each sample was sequenced in both directions. The status of H3K4 and H3K27 bivalent domains was determined by chromatin immunopercipitation followed by quantitative PCR analysis, as previously described (Bernstein et al., 2006).

Blastocyst Injections and Teratoma Formation.

Diploid or tetraploid blastocysts (94-98 h after HCG injection) were placed in a drop of DMEM with 15% FCS under mineral oil. A flat-tip microinjection pipette with an internal diameter of 12-15 mm was used for iPS cell injection (using a Piezo micromanipulator 34). A controlled number of cells was injected into the blastocyst cavity. After injection, blastocysts were returned to KSOM media and placed at 37° C. until transferred to recipient females. Ten to fifteen injected blastocysts were transferred to each uterine horn of 2.5 days post coitum pseudo-pregnant B6D2F1 females. To recover full-term pups, recipient mothers were killed at 19.5 days post coitum. Surviving pups were fostered to lactating BALB/c mothers. For teratoma generation, $2*10^6$ cells were injected subcutaneously into both flanks of recipient SCID mice, and tumors were harvested for sectioning 3-6 weeks after initial injection.

Immunofluorescence Staining.

Cells were fixed in 4% paraformaldehyde for 20 minutes at 25° C., washed 3 times with PBS and blocked for 15 min with 5% FBS in PBS containing 0.1% Triton-X. After incubation with primary antibodies against Nanog (polyclonal rabbit, Bethyl) and SSEA1 (monoclonal mouse, Developmental Studies Hybridoma Bank) for 1 h in 1% FBS in PBS containing 0.1% Triton-X, cells were washed 3 times with PBS and incubated with fluorophore-labeled appropriate secondary antibodies purchased from Jackson Immunoresearch. Specimens were analyzed on an Olympus Fluorescence microscope and images were acquired with a Zeiss Axiocam camera.

Quantitative RT-PCR.

Bone marrow B cells were grown on OP9 cells in media supplemented with IL-7, SCF, Flt3, while spleen B cells were grown with IL-4, anti-CD40 and LPS. OP9 cells were depleted by pre-plating on gelatin-coated plates before the cells were harvested for mRNA preparation. Puromycin was added to fibroblast (2 µg/ml) and B cell (0.3 µg/ml) cultures to eliminate non-transgenic cells. Total RNA was isolated using Rneasy Kit (Qiagen). Three micrograms of total RNA was treated with DNase I to remove potential contamination of genomic DNA using a DNA Free RNA kit (Zymo Research, Orange, Calif.). One microgram of DNase I-treated RNA was reverse transcribed using a First Strand Synthesis kit (Invitrogen) and ultimately resuspended in 100 ul of water. Quantitative PCR analysis was performed in triplicate using 1/50 of the reverse transcription reaction in an ABI Prism 7000 (Applied Biosystems, Foster City, Calif.) with Platinum SYBR green qPCR SuperMix-UDG with ROX (Invitrogen). Primers used for amplification were as follows: c-Myc: F, 5'-ACCTAACTCGAGGAG-GAGCTGG-3' (SEQ ID NO: 1) and R, 5'-TCCA-CATAGCGTAAAAGGAGC-3' (SEQ ID NO: 2); Klf4: F, 5'-ACACTGTCTTCCCACGAGGG-3' (SEQ ID NO: 3) and R, 5'-GGCATTAAAGCAGCGTATCCA-3' (SEQ ID NO: 4); Sox2: F, 5'-CATTAACGGCACACTGCCC-3' (SEQ ID NO: 5) and R, 5'-GGCATTAAAGCAGCGTATCCA-3' (SEQ ID NO: 6); Oct4: F, 5'-AGCCTGGCCTGTCTGT-CACTC-3' (SEQ ID NO: 7) and R, 5'-GGCATTAAAGCA-GCGTATCCA-3' (SEQ ID NO: 8). To ensure equal loading of cDNA into RT reactions, GAPDH mRNA was amplified using the following primers: F, 5'-TTCACCACCATGGA-GAAGGC-3' (SEQ ID NO: 9); and R, 5'-CCCTTTTG-GCTCCACCCT-3' (SEQ ID NO: 10). Data were extracted from the linear range of amplification. All graphs of qRT-PCR data shown represent samples of RNA that were DNase treated, reverse transcribed, and amplified in parallel to avoid variation inherent in these procedures. Gene expression analysis for ES markers was performed by PCR using previously published primers (Takahashi and Yamanaka, 2006).

Flow Cytometry Analysis and Cell Sorting.

The following fluorescently conjugated antibodies (PE, FITC, Cy-Chrome or APC labeled) were used for FACS analysis and cell sorting: anti-SSEA1 (RnD systems), anti-Igκ, anti-Igλ1, 2, 3, anti-CD19, anti-B220, anti-c-Kit, anti-CD25, anti-sIgM, anti-sIgD (all obtained from BD-Biosciences). Cell sorting was performed by using FACS-Aria (BD-Biosciences), and consistently achieved cell sorting purity of >97%. For isolation of mature IgM+IgD+ B cells from spleen and lymph nodes, cells were depleted of Lin+ non-B cells by MACS sorting after staining with lineage markers antibodies (CD3e, CD4, CD8, CD11c, Gr1, c-Kit, Mac1 and Ter119) prior to sorting.

Results

Inducible Expression of Reprogramming Factors in the B Cell Lineage

Initially work described herein sought to determine whether Oct4, Sox2, Klf4 and c-Myc transcription factors, which were shown to be sufficient to reprogram mouse and human fibroblast cultures (Meissner at al., 2007; Okita at al., 2007; Takahashi et al., 2007; Takahashi and Yamanaka, 2006; Wernig at al., 2007) and mouse liver- and stomach-derived cell cultures (Aoi at al., 2008), were capable of reprogramming cells of the B cell lineage. Because of the relatively low infectivity of mouse lymphocytes with viruses, we established a system that allowed inducible transgenic expression of the four reprogramming factors in B cells.

Figure 3:
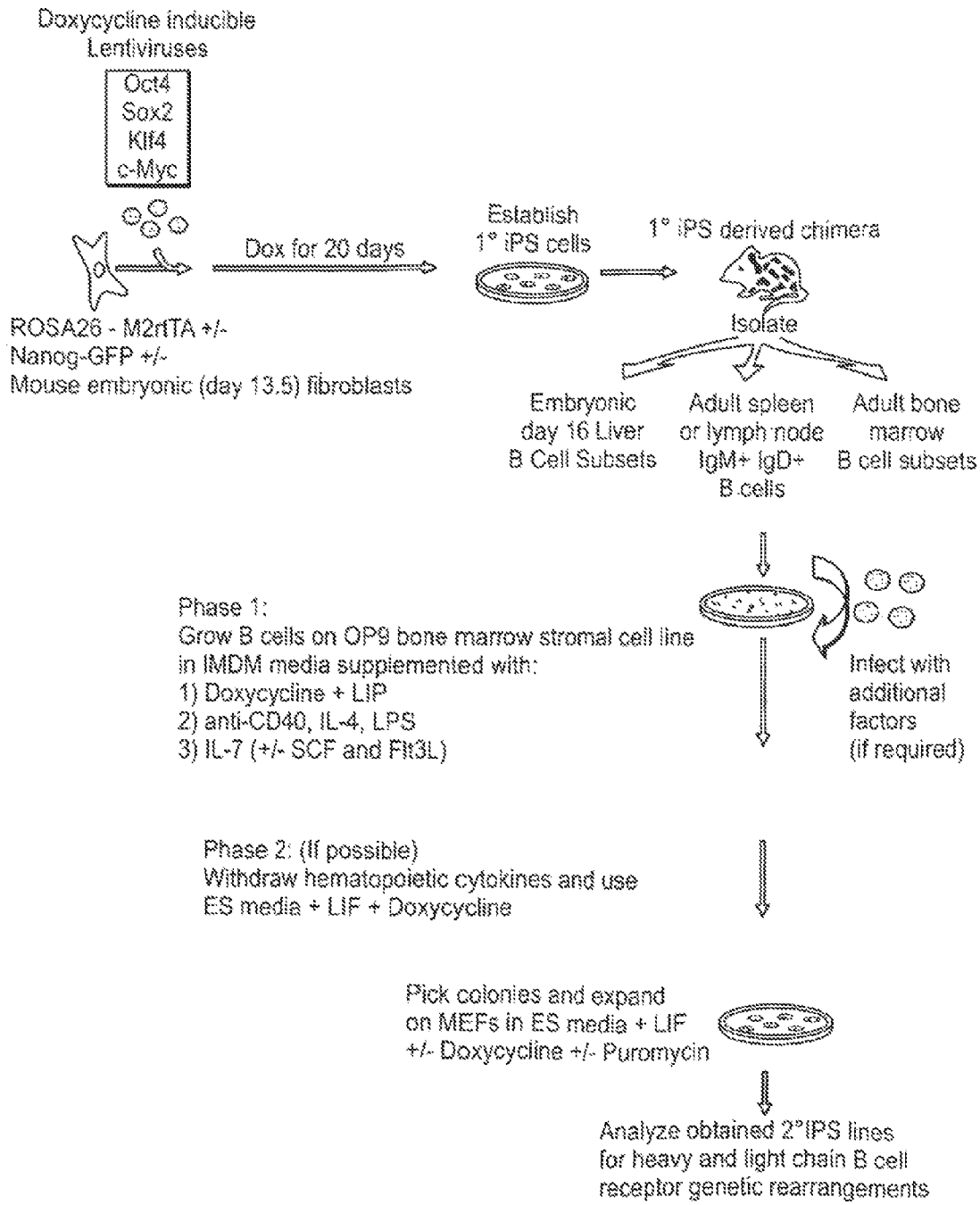
FIG. 3 shows the transgenic inducible expression of OCT4, Sox2, Klf4 and c-Myc in the mouse B cell lineage, in particular a schematic drawing representing the strategy used in this study for reprogramming cells from the B cell lineage.

To this end, we have recently shown that doxycycline-inducible (Dox) lentiviral vectors encoding the Oct4, Sox2, c-Myc and Klf4 transcription factors are able to reprogram mouse embryonic fibroblasts (MEFs) into stable iPS cells that maintain their pluripotency after Dox withdrawal (Brambrink et al., 2008). When injected into blastocysts these cells were capable of generating postnatal chimeras which contain clonal populations of somatic cells carrying the identical proviral copies that generated the "primary" iPS cells (Brambrink et al., 2008). We reasoned that B cells derived from these chimeras, when exposed to Dox under appropriate culture conditions, might activate the proviral copies that induced the primary iPS cells and thus might facilitate reprogramming and the generation of "secondary" iPS cells (FIG. 3).

MEFs carrying a constitutively expressed reverse tetracycline trans-activator driven by the ROSA26 promoter (R26-M2rtTA) and a knock-in of GFP into the endogenous Nanog locus (Nanog-GFP) were infected with the Dox-inducible lentiviral vectors encoding Oct4, Sox2, c-Myc and Klf4 genes (Brambrink et al., 2008). Large macroscopic colonies appearing after 12 days of Dox treatment were picked and propagated without Dox to establish Nanog-GFP+ iPS lines, which expressed pluripotency markers alkaline phosphatase (AP), SSEA1 antigen and Oct4. The MEF-derived primary iPS cells were injected into blastocysts to generate embryonic and adult chimeras. Pro-B (B220+c-Kit+) and Pre-B cells (B220+CD25+) (Cobaleda et al., 2007a) were isolated from the bone marrow, and mature IgM+IgD+ B cells were purified from the spleen of 8 week old adult chimeric mice and grown in media supplemented with hematopoietic cytokines and Dox for 7 days. A functional puromycin resistance gene had been inserted into the ROSA26 locus as part of the targeting strategy of M2rtTA (Brambrink et al., 2008) and allowed elimination of host-derived non-transgenic B cells by puromycin selection (0.3 µg/ml).

Chimeras derived from MEF-iPS-#1 cell line were chosen for further study, as donor B cells from chimeras induced high expression levels of the 4 factors in the presence of Dox. Adult tail tip fibroblasts derived from MEF-iPS #1 line also yielded Nanog-GFP+iPS lines following addition of Dox, though the expression levels of the four factors following addition of Dox were lower than those observed in B cells derived from the same chimera.

Reprogramming of Non-Terminally Differentiated B Cells

Initial attempts failed to reprogram bone marrow-derived B cells and spleen B cells that had been cultured on irradiated feeder cells in ES media supplemented with LIF and Dox, as the cells died within five days in culture. We reasoned that addition of cytokines might be necessary to allow for an initial proliferation of the B cells that would ensure a sufficient number of cell divisions necessary to initiate epigenetic reprogramming by expression of the four factors. Therefore, we optimized culture conditions that would support immature and mature B cell growth as well as that of ES cells to ensure viability during the reprogramming process from B to iPS cells.

Cells were grown on OP9 bone marrow stromal cells in media supplemented with LIF which is required for ES cell growth, with IL-7, SCF and Flt-3L which support B cell development (Milne at al., 2004), and with IL-4, anti-CD40 and LPS which are important for proliferation of mature B cells (Hayashi et al., 2005). In initial experiments we detected AP-positive colonies in cultures of sorted Pre- and Pro-B cell subsets derived from 8 week old adult chimera bone marrow after 14 days of Dox treatment. Small flat colonies appeared 3 days after Dox induction that subsequently underwent robust expansion. Around day 11 after Dox induction smooth ES-like small colonies embedded within the granulated large colonies were observed which became Nanog-GFP+ at day 14. Colonies were picked 14 days after Dox induction from 3 independent experiments and grown on MEF feeders in ES media without Dox. Within 3 passages over 90% of the picked colonies grew into homogenous ES-like Nanog-GFP+ iPS cells. In the following we will refer to these cell lines as iB-iPS cells (for iPS cells derived from "immature" non-fully differentiated B cells including Pre- and Pro-B cells)

Genomic DNA harvested from established iB-iPS cell lines was analyzed by PCR for heavy and light chain rearrangements. We used previously described degenerate primers that recognize the majority of rearrangements involving three major families of V segments of the heavy chain locus ($V_H$Q52, $V_H$7183-DJ, $V_H$Gam3.8), $D_H$-$J_H$ heavy chain rearrangements, and Igκ and Igλ light chain rearrangements (Chang at al., 1992; Cobaleda at al., 2007a) (Table 2). Representative cell lines reprogrammed from the B220+c-Kit+ Pro-B cell subpopulation showed that some iPS lines carried $D_H$-$J_H$ rearrangements (lines #1, 2, 7, 9), whereas others did not show evidence for any IgH rearrangements (lines #3, 4, 6), as would be expected for rearrangements in the donor B cell subset at the Pro-B cell stage of development. Cell lines established from the adult bone marrow-derived B220+CD25+ Pre-B cells carried at least one $V_H$-$DJ_H$ rearrangement and an additional $D_H$-$J_H$ or $V_H$-$DJ_H$ rearrangement (lines #5, 8), both genetic rearrangements of the IgH locus typically observed in such B cell populations (Jung at al., 2006). IgH rearrangements in the iB-iPS were verified by Southern blot analysis.

For subsequent analysis, we focused on cell lines that contained genetic evidence for IgH rearrangements, as only those can be definitively traced to cells committed to the B cell lineage. All iB-iPS cell lines stained positive for the ES markers AP, SSEA1 and Oct4, and all cell lines tested (#5, 7, 8, 9) generated differentiated teratomas when injected into immunodeficient mice. Furthermore, we obtained adult chimeras from several iB-iPS cell lines (Table 1). Representative Southern blots of tail DNA from an iB-iPS#8 cell line-derived chimera showed a heavy chain rearrangement pattern identical to the donor iB-iPS cell line, thus confirming that the chimera was derived from the respective iB-iPS cell line and not from contaminating ES- or MEF-derived iPS cells. A chimera derived from iB-iPS line #9 produced 100% germline transmission as demonstrated by the agouti coat color of all mice obtained. As expected, Southern blot analysis confirmed segregation of the rearranged IgH allele found in the donor iB-iPS line in some of the mice. These results demonstrate that cells committed to the B cell lineage carrying $D_H$-$J_H$ or $V_H$-$DJ_H$ rearrangements, although not fully differentiated, can be reprogrammed to a pluripotent ES-like state by the induction of the 4 transcription factors Oct4, Sox2, Klf4 and c-Myc.

Reprogramming of Terminally Differentiated B Cells

We failed to generate any reprogrammed AP+ colonies from mature spleen IgM+IgD+ cells or bone marrow derived IgK+ cells in 5 independent experiments. This was puzzling given that IgM+IgD+ mature transgenic B cells could be maintained in our culture conditions for up to 6 weeks and continued to express B cell markers. It appeared possible that the transgenic B cells were able to proliferate in conditioned media with Dox for a relatively extended period due to induction of c-Myc, which is known to promote B cell growth and is a key player in B cell transformation (Zhu et al., 2005). We tested, therefore, the hypothesis that additional pluripotency factors might be needed to achieve reprogramming of mature B cells. Adult IgM+IgD+ spleen B cells were infected with combinations of retroviruses encoding 20 different pluripotency factors that were originally generated to screen for fibroblast reprogramming (Takahashi and Yamanaka, 2006). Yet, these experiments repeatedly yielded negative results.

As an alternative approach, we aimed to "sensitize" the B cells to respond to Dox-dependent 4-factor induction by altering their mature B cell identity. It has been shown that over-expression of the myeloid transcription factor CCAAT/enhancer-binding protein-α (C/EBPα) is able to reprogram B cells into macrophage-like cells (Xie et al., 2004) by disrupting the function of Pax5, a transcription factor that is a master regulator of mature B cell development and immunological function (Cobaleda et al., 2007b). In these experiments the C/EBPα transduced B cells had been grown on bone marrow stromal cells in the presence of myeloid cytokines and had differentiated into functional macrophages (Xie at al., 2004). We tested, therefore, whether transduction with C/EBPα would facilitate reprogramming of mature B cells.

Adult spleen B cells derived from 10 week-old chimeras were transduced with a retrovirus encoding C/EBPα and/or the IL7-Rα subunit and cultured on OP9 cells in the presence of Dox to induce the four factors Oct4, Sox2, Klf4 and c-Myc. AP positive colonies appeared after 14 days in culture in cells transduced with C/EBPα or with C/EBPα and IL7-Rα but not in cells transduced with IL7-Rα alone. After 3 days of growth on OP9, small adherent colonies were formed which continued to grow into denser granulated colonies. Similarly to Dox-induced Pre- and Pro-B cell cultures, small round ES-like colonies appeared within the large dense granulated colonies, and Nanog-GFP+ foci were readily detected at approximately day 14.

Plating on OP9 bone marrow stromal cells was critical for recovering iPS cells, as no iPS cells were detected when the cells were cultured on MEF feeders or gelatin coated plates. Colonies isolated at day 14 were passaged on MEF feeder cells without hematopoietic cytokines or Dox and within 3 passages all lines assumed an ES-like morphology and were positive for the Nanog-GFP marker.

We performed FACS analysis to measure kinetics of SSEA1 and Nanog pluripotency marker activation in Dox induced bone marrow B220+ B cell populations and mature spleen IgM+IgD+ B cells infected with C/EBPα retrovirus. This assay showed similar reprogramming kinetics in which SSEA1+ cells were initially detected at day 7 and became abundant at the day 11 after Dox addition. Nanog expression was detected at day 15 similar to the sequential appearance of pluripotency markers during reprogramming of MEFs (Brambrink et al., 2008). Our results suggest that transduction with C/EBPα can sensitize mature B cells to respond to the expression of Oct4, Sox2, c-Myc and Klf4 and re-express pluripotency markers.

We established 120 independent iPS lines that were picked from independent tissue culture wells containing IgM+IgD+ B cells from adult spleen and lymph nodes at 14 days after Dox addition and C/EBPα transduction, and 9 cell lines were randomly selected for in depth characterization (Lines 1-6 obtained from adult spleen and 7-9 from adult lymph nodes). In the following we will refer to these cell lines as "B-iPS" cells (iPS cells derived from mature "B" cells).

Next, we characterized marker expression, DNA methylation and histone marks of the B-iPS cell lines. Immunoflorescence staining showed that all B-iPS cell lines uniformly expressed ES cell markers AP, SSEA1 antigen, Oct4 protein and were positive for Nanog-GFP. Gene expression analysis by RT-PCR showed that B-iPS and ES cells, but not primary B cells, expressed comparable levels of Nanog, Ecat1, Rex1, Zfp296 and GDF3 genes. Bisulphite sequencing was performed to determine the methylation status of Oct4 and Nanog gene promoters for iB-iPS and B-iPS cell lines. As expected, fibroblast and B cell control samples displayed extensive methylation at both promoters, whereas B-iPS and iB-iPS lines showed widespread demethylation of these regions similar to that seen in ES cells.

To assess the chromatin state of the cells, chromatin immunopercipitation (ChIP) and real time PCR were performed to quantify 'active' histone H3 lysine 4 trimethylation (H3K4me3) and 'repressive' histone H3 lysine 27 trimethylation (H3K27me3) methylation marks on a selected set of genes known to be bivalent (carry both active and repressive methylation marks) in ES cells (Bernstein et al., 2006). As cells differentiate, such genes can become) "monovalent" and carry either H3K4me3 or H3K27me3 marks, depending on their expression. The promoter region for the B cell transcription factor gene Pax5 displayed strong enrichment for H3K4me3 methylation in the donor mature B cells, whereas H3K27me3 methylation predominated at the silent genes Zfpm2 and Irx2. Conversely, in B-iPS and ES cells all these genes carry equivalent enrichment for both histone modifications, consistent with the notion that these bivalent domains were re-established during reprogramming.

In summary, our results indicate that the chromatin configuration of the B-iPS cells had been converted from a configuration typical of terminally differentiated adult mature B cells to one that is characteristic for ES cells (Bernstein et al., 2006).

Rearrangements of Immunoglobulin Loci in B-iPS Cells Confirm Mature B Cell Identity of the Donor Cells In order to characterize the genomic rearrangements of the Ig loci in the B-iPS cells, genomic DNA from MEF-depleted iPS cell lines grown on gelatin was analyzed for IgH, Igκ and Igλ rearrangements by complementary approaches that included Southern blotting, PCR and sequencing of individual PCR fragments (Alt et al., 1981; Chang et al., 1992; Cobaleda et al., 2007a; Lewis at al., 1982; Schlissel et al., 1991) (Table 6). All cell lines contained 2 heavy chain rearrangements: one was a productive in-frame V-DJ rearrangement whereas the other was either a frozen D-J rearrangement or a non-productive V-DJ rearrangement. These results are consistent with the well established observation that adult mature B cells in the periphery have 2 rearranged heavy chain loci (Jung et al., 2006).

As predicted for mature B cells, the light chain loci had one productive in-frame Igκ or Igλ light chain rearrangement (Jung et al., 2006). Though 95% of Igλ+ B cells in mice are known to carry unproductive Igκ rearrangements, B-iPS cell line #9 was derived from a minor B cell subpopulation with a rearranged productive Igλ chain and kappa locus that was retained in the germline configuration (Nadel et al., 1990; Oberdoerffer et al., 2003). Finally, sequences obtained from heavy and light chain rearrangements from B-iPS cell line #4 provided conclusive evidence that the donor B cell nucleus that yielded this cell line had undergone somatic hypermutation, a process that occurs after antigen encounter in vivo and involves acquiring a high rate of somatic mutations at "hotspots" located throughout the DNA encoding the immunoglobulin variable region (Teng and Papavasiliou, 2007). This directed hypermutation allows for the selection of B cells that express immunoglobulin receptors possessing an enhanced ability to recognize and bind a specific foreign antigen. The abundance of mostly non-silent mutations in the variable region of the productive rearrangements in this cell line shows that non-naïve B cells that have already encountered antigen in vivo are also amenable to direct reprogramming.

B-iPS#4 cell line likely arose from a contaminating IgM+IgD− cell during the cell sorting process because IgM+IgD+ B cells had been selected for reprogramming and this selection would be expected to yield only naïve mature B cells as cells that undergo antigen encounter and somatic hypermutation downregulate the IgD antigen (Matthias and Rolink, 2005), Finally, the C/EBPα viral transgene was detected in genomic DNA from all B-iPS cell lines analyzed. The genomic analyses described above provide unequivocal evidence that the iPS cell lines were derived from terminally differentiated adult mature B cells which had completed their maturation in the bone marrow, carried the expected functional heavy and light chain rearrangements, and populated peripheral lymphoid organs.

Developmental Potential of B-iPS Cells

As an initial test for developmental potency we injected 8 B-iPS cell lines subcutaneously into the dorsal flanks of immunodeficient (SCID) mice. Six weeks after injection, macroscopic teratomas were observed in all injected mice. Histological examination showed that the teratomas contained cell types representing all three embryonic germ layers, including gut-like epithelial tissues (endoderm), striated muscle (mesoderm), cartilage (mesoderm), neural tissues (ectoderm), and keratin-containing epidermal tissues (ectoderm). To assess more stringently their developmental potential, individual B-iPS cell lines were injected into diploid (2N) blastocysts resulting in the generation of viable, high-contribution chimeras from all 4 B-iPS cell lines tested (Table 5). Southern blot analysis of genomic DNA isolated from B-iPS #4- and #1-derived chimeras revealed the presence of genomic fragments corresponding to rearranged Igκ alleles identical to those observed in the donor injected B-iPS cell lines. Importantly, B-iPS line #1 contributed to the germline as was evident by the derivation of offspring carrying a constitutively expressed lentiviral transgene EGFP vector that was used for transducing B-iPS line #1 prior to blastocyst injections.

The generation of mice by tetraploid complementation, which involves injection of pluripotent cells in 4N host blastocysts, represents the most rigorous test for developmental potency because the resulting embryos are derived only from injected donor cells (Eggan et al., 2001). Both B-iPS lines tested (#4 and #9) were able to generate mid- and late-gestation all B-iPS embryos' after injection into 4N blastocysts. Sensitive PCR analysis for the detection of a 2 Kb germ-line region from the B cell receptor heavy chain locus that is lost upon initiation of genetic rearrangement (Chang et al., 1992) shows that genomic DNA from B-iPS #4 cell line embryos derived by tetraploid complementation had lost the germ line band and carried only the D-J rearrangement as predicted from the repertoire in the donor nucleus. This conclusion was confirmed by Southern blot analysis of genomic DNA from a day E14.5 tetraploid embryo obtained from B-iPS#4 demonstrating two rearranged IgK locus alleles, without any evidence for a germline allele. This is in contrast to DNA obtained from 2N chimeras that yielded the same 2 rearranged IgK alleles and a germline band originating from host blastocyst derived cells.

We next tested the ability of reprogrammed mature B cells to generate monoclonal B cells in vivo as a result of the restrictions imposed by their pre-rearranged IgH and IgL loci (Hochedlinger and Jaenisch, 2002; Inoue et al., 2005; Oberdoerffer at al., 2003). To facilitate the isolation of B-iPS derived cells in chimeric mice, B-iPS lines #4 and 9 were labeled with the GFP marker by lentiviral vector-mediated transduction prior to blastocyst injection. Surface expression of Igκ and Igλ light chain proteins expressed on CD19+ cells purified from peripheral blood was evaluated by FACS staining. All GFP+ B cells in B-iPS #4-derived chimeras expressed Igκ chain, but not Igλ protein, consistent with the genetic analysis that showed a functional Igκ light chain rearrangement in this cell line. In contrast, B-iPS #9 cell line-derived B cells carried only a functional IgA light chain rearrangement.

Finally, we established two B-iPS cell lines that were generated by direct infection of genetically unmodified mature B cells with the Oct-4, Klf4, Sox2, c-Myc and C/EBPα grown in the same culture conditions described in our study and were capable of generating adult chimeras. In summary, our results provide unequivocal molecular and functional proof that mature B cell donor nuclei that contain functional light and heavy chain rearrangements were reprogrammed to pluripotency. The cell lines carried productive heavy and light chain rearrangements, expressed pluripotency markers, generated live chimeras and contributed to the germ line.

Efficiency of Reprogramming Mature Adult B Cells to Pluripotency

Figure 4:
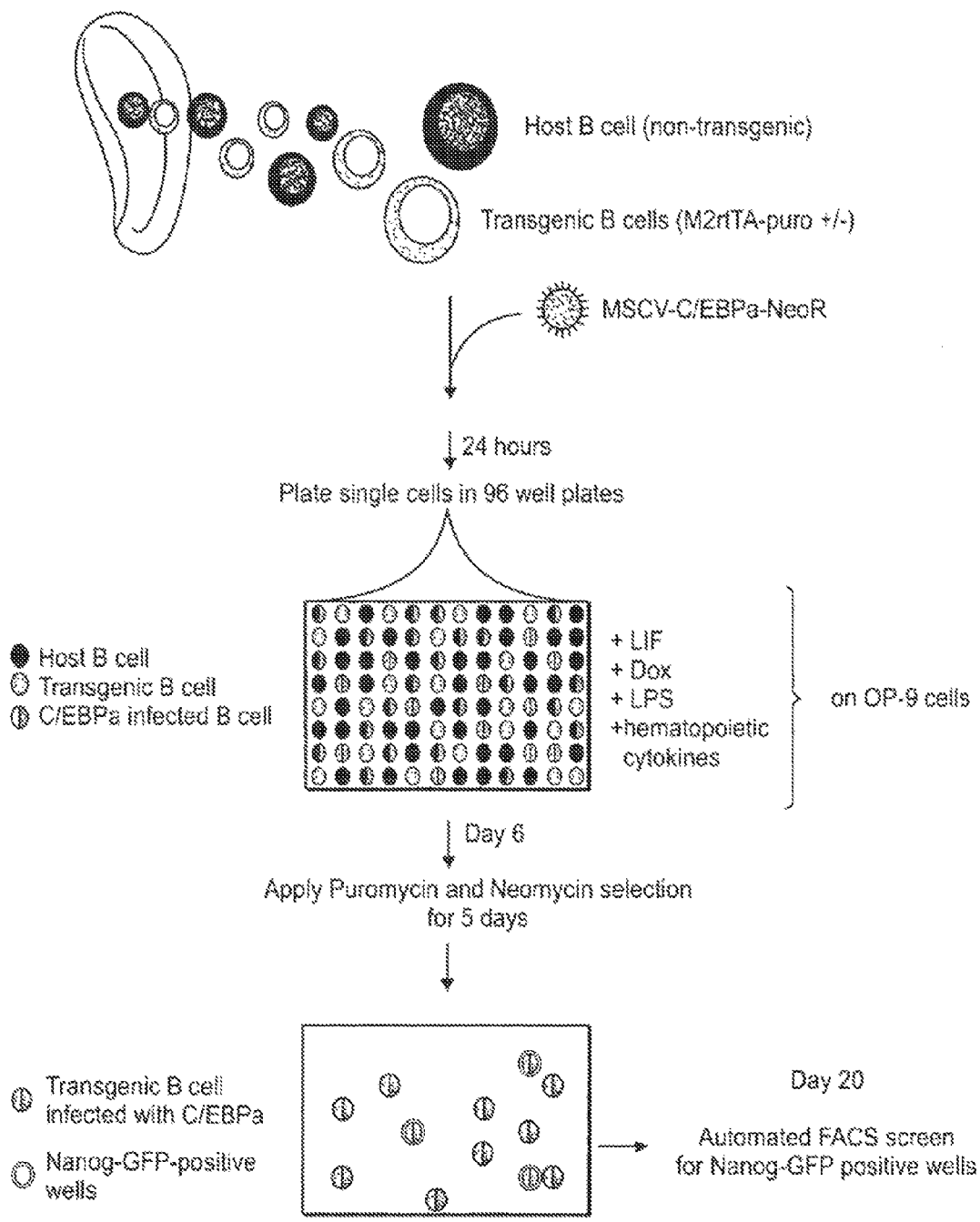
FIG. 4 shows a schematic representation of experiments attempting to measure reprogramming efficiency. $3*10^{-6}$ CD19+ adult B cells were infected with retrovirus encoding C/EBPα-NeoR construct, and after 24 hours we sorted IgM+IgD+ mature adult B cells and plated them as single cells in 96-well plates preplated with OP9 stromal cell line. Cells were grown in conditioned medium+Dox+LIF throughout the experiment. On day 6, culture wells were subjected to puromycin and neomycin selections for 5 days, which allowed only the growth of transgenic B cells infected with C/EBPα. On day 20, the wells containing drug resistant cells were screened for Nanog-GFP expression by FACS analysis. Wells that scored positive were subsequently passaged on MEFs in ES media and grown into iPS cell lines.

To estimate the efficiency of reprogramming of mature adult B cells to pluripotency, a large starting pool ($3*10^{-6}$) of CD19+ B cells isolated from the spleen of adult chimeras was infected with a C/EBPα encoding retrovirus carrying a neomycin resistance gene. After 24 hours, IgM+IgD+ B cells were plated as single cells in 96-well plates on OP9 stromal cells in cytokine conditioned medium in the presence of Dox and LIF. Five days after plating puromycin and neomycin were added to the culture medium in order to select for transgenic B cells that had also been infected with C/EBPα (FIG. 4). At day 20 wells that showed cell growth were screened by FACS for detection of Nanog-GFP+ cells. Wells that scored positive were expanded, and Nanog-GFP iPS cells appeared within 3 passages. PCR analysis of B-iPS lines obtained confirmed that all cell lines obtained from two independent experiments originated from C/EBPα-infected mature B cells that had distinct B cell receptor rearrangements. Based on these data, we were able to calculate the efficiency of reprogramming by dividing the number of GFP+ wells obtained (output) by the number of C/EBPα-infected transgenic B cell-containing wells (puromycin and neomycin double resistant wells=input). This calculation suggested that the relative efficiency for direct reprogramming of mature B cells was approximately 1 in 27-34 cells. We attribute the relatively high efficiency of reprogramming to the strong Dox-mediated induction of 4 out of the 5 ectopically expressed factors that did not rely on retroviral vector infection and random proviral integrations.

TABLE 1

Summary of primary iPS lines.

| Initial outgrowth (day picked) | GFP expression | Growth post picking | primary iPS line | GFP positive |
|---|---|---|---|---|
| 1 (11) | − | + | − | — |
| 2 (11) | − | + | − | — |
| 3 (11) | − | − | | |
| 4 (11) | − | | − | |
| 5 (11) | − | + | − | — |
| 6 (11) | − | + | − | — |
| 7 (11) | − | + | + | 18 |
| 8 (11) | − | + | − | — |
| 9 (16) | − | + | + | 20 |
| 10 (16) | − | + | + | 20 |
| 11 (16) | + | + | + | 18 |
| 12 (16) | − | − | | |
| 13 (16) | − | + | − | — |
| 14 (16) | − | + | + | 26 |
| 15 (16) | − | + | − | — |
| 16 (16) | − | − | | |
| 17 (16) | − | + | − | — |
| 18 (16) | − | + | − | — |

TABLE 2

Summary of secondary iPS lines.

| subclones picked on day 16 | GFP expression | Growth post picking | secondary iPS line | GFP positive |
|---|---|---|---|---|
| 1.1 | − | + | + | 28 |
| 1.2 | − | + | − | — |
| 1.3 | − | + | + | 30 |
| 4.1 | − | + | − | — |
| 4.2 | − | − | | |
| 4.3 | − | + | − | — |
| 5.1 | − | + | + | 32 |
| 5.2 | − | − | | |
| 5.3 | − | − | | |
| 6.1 | − | + | − | —*** |
| 6.2 | − | + | − | —*** |
| 6.3 | − | + | − | —*** |
| 8.1 | − | + | + | 28 |
| 8.2 | − | + | + | 36 |
| 8.3 | − | − | | |

TABLE 3

Summary of genetically unmodified iPS derivation

| Background/type | Picked on day 16 | # expanded | Prim/sec iPS lines |
|---|---|---|---|
| 129/B6 F1/MEFs | 8 | 3 | 2 |
| 129/B6 F1/TT | 8 | 3 | 1 |
| Balb/MEFs | 8 | 3 | 2 |
| B6/DBA F1/TT | 8 | 3 | 1 |
| Whole plate 129/B6 F1/MBF | — | 5 | 5 |

TABLE 4

Summary of blastocyst injections.

| Cell line | 2N injections | | | 4N injections | | |
|---|---|---|---|---|---|---|
| | Injected blast. | Live chimeras | Chimerism (%) | Injected blast. | Dead embryos (arrested) | Live embryos (analyzed) |
| OG-7 | 25 | 2 | 15-60 | 74 | 4 (E11-15)* | — |
| OG-7.3 | 18 | 1 | 40 | — | — | — |
| OG-8.1 | 16 | 3 | 30-60 | — | — | — |
| OG-9 | nd | — | — | 14 | 1 (E12.5)** | — |
| OG-10 | 18 | 3 | 20-40 | — | — | — |
| OG-14 | nd | — | — | 42 | 4 (E11-14) | 3 (E14.5) |
| 129/B6 F1/MEFs | 18 | 1*** | *** | — | — | — |
| Balb/c MEFs | 22 | 3*** | *** | — | — | — |

TABLE 5

Summary of blastocyst injections. The extent of chimerism was estimated on the basis of coat color or EGFP expression.

| Cell line | 2N injections | | | | 4N injections | | |
|---|---|---|---|---|---|---|---|
| | Injected blastocysts | Live chimeras | chimerism | Germline | Injected blastocysts | Dead embryos (arrested) | Live embryos (analyzed) |
| iB-iPS #1 | 36 | 1 | 10-30 | ND | ND | ND | ND |
| iB-iPS #4 | 95 | 5 | 40-70 | Yes | ND | ND | ND |
| iB-iPS #8 | 20 | 2 | 50-70 | No | ND | ND | ND |
| B-iPS #1 | 40 | 3 | 20-60 | Yes | ND | ND | ND |
| B-iPS #2 | 24 | 2 | 30-50 | No | ND | ND | ND |
| B-iPS #4 | 135 | 6 | 30-80 | ND | 115 | 7 (E10-14.5) | 3 (E12.5) 2 (E14.5) |
| B-iPS #9 | 95 | 8 | 30-80 | ND | 90 | 5 (E9-12.5) | 5 (E12.5) |
| B-iPS #121 | 46 | 3 | 30-60 | ND | ND | ND | ND |

ND, not determined.
4N injected blastocysts were analyzed between day E10.5 and E14.5.
'Analyzed' indicates the day of embryonic development analyzed; 'arrested' indicates the estimated stage of development of dead embryos.

TABLE 6

Primers used for PCR analysis of Ig rearrangements.
K: G or T, M: A or C, S: C or G, R: A or G, W: A or T, Y: C or T.

Sense Oligonucleotides

| Igh locus | $V_H$J558 | CGAGCTCTCCARCACAGCCTWCATGCARCTCARC (SEQ ID NO. 38) |
|---|---|---|
| | $V_H$7183 | CGGTACCAAGAASAMCCTGTWCCTGCAAATGASC (SEQ ID NO. 39) |
| | $V_H$Q52 | CGGTACCAGACTGARCATCASCAAGGACAAYTCC (SEQ ID NO. 40) |
| | $V_H$Gam3.8 | CAAGGGACOGTTTGCCTTCTCTTTGGAA (SEQ ID NO. 41) |
| | DSF | AGGGATCCTTGTGAAGGGATCTACTACTGTG (SEQ ID NO. 42) |
| IgL loci | Vλ1 | GCCATTTCCCCAGGCTGTTGTGACTCAGG (SEQ ID NO. 43) |
| | Vκ | GGCTGCAGSTTCAGTGGCAGTGGRTCWGGRAC (SEQ ID NO. 44) |

Antisense Oligonucleotides

| Igh locus | JH4 | TCTCAGCCGGCTCCCTCAGGG (SEQ ID NO. 45) |
|---|---|---|
| | JH4 (used with DSF primer) | AAAGACCTGCAGAGGCCATTCTTACC (SEQ ID NO. 46) |

TABLE 6-continued

Primers used for PCR analysis of Ig rearrangements.
K: G or T, M: A or C, S: C or G, R: A or G, W: A or T, Y: C or T.

| IgL loci | Jλ1,3 | ACTCACCTAGGACAGTCAGCTTGGTTCC (SEQ ID NO. 47) |
| --- | --- | --- |
| | Jκ5 | ATGCGACGTCAACTGATAATGAGCCCTCTCC (SEQ ID NO. 48) |

REFERENCES

The following references are cited herein and their teachings are incorporated by reference for all purposes.

Alt, F., at al., Organization and reorganization of immunoglobulin genes in A-MOLT-transformed cells: rearrangement of heavy but not light chain genes. Cell 27, 381-390 (1981).

Aoi, T., et al., Generation of Pluripotent Stem Cells from Adult Mouse Liver and Stomach Cells. Science. Science Online Express (2008).

Avilion, J., et al., Nat. Biotechnol. 20: 1240-45 (2003).

Azuara, V., et al., Nat Cell Biol 8 (5), 532 (2006).

Bernstein, B. E., et al., A bivalent chromatin structure marks key developmental genes in embryonic stem cells. Cell 125, 315-326 (2006).

Blelloch, R., at al., Reprogramming efficiency following somatic cell nuclear transfer is influenced by the differentiation and methylation state of the donor nucleus. Stem cells (Dayton, Ohio) 24, 2007-2013 (2006).

Boyer, L. A., at al., Core transcriptional regulatory circuitry in human embryonic stem cells. Cell 122, 947-956 (2005).

Boyer, L. A., et al., Nature 441 (7091), 349 (2006).

Brambrink, T., et al., Sequential Expression of Pluripotency Markers during Direct Reprogramming of Mouse Somatic Cells. Cell Stem Cell 2, 151-159 (2008).

Brambrink, T., et al., Proc Natl Acad Sci USA 103 (4), 933 (2006).

Byrne, J. A., at al., Producing primate embryonic stem cells by somatic cell nuclear transfer. Nature 450, 497-502 (2007).

Chang, Y., et al., Enumeration and characterization of DJH structures in mouse fetal liver. The EMBO journal 11, 1891-1899 (1992).

Chapman, V., et al., Nature, 284 (1984).

Cobaleda, C., at al., (2007a). Conversion of mature B cells into T cells by dedifferentiation to uncommitted progenitors. Nature 449, 473-477.

Cobaleda, C., at al., (2007b). Pax5: the guardian of B cell identity and function. Nature immunology 8, 463-470.

Cowan, C. A., et al., Nuclear reprogramming of somatic cells after fusion with human embryonic stem cells. Science (New York, N.Y. 309, 1369-1373 (2005).

Eads, C. A. and P. W. Laird, Methods Mol Biol 200, 71 (2002).

Eggan, K., et al., Hybrid vigor, fetal overgrowth, and viability of mice derived by nuclear cloning and tetraploid embryo complementation. Proceedings of the National Academy of Sciences of the United States of America 98, 6209-6214 (2001).

Eggan, K., et al., Mice cloned from olfactory sensory neurons. Nature 428, 44-49 (2004).

Gossen M. et al., Transcriptional activation by tetracyclines. in mammalian cells, Science 268: 1766-1769 (1995).

Grompe, M. (2005). The origin of hepatocytes. Gastroenterology 128, 2158-2160.

Gurdon, J. B. (2006). From nuclear transfer to nuclear reprogramming: the reversal of cell differentiation. Annual review of cell and developmental biology 22, 1-22.

Hanna, J., et al., (2007). Treatment of sickle cell anemia mouse model with iPS cells generated from autologous skin. Science 318, 1920-1923.

Hanna, L. A., et al., Genes Dev. 16: 2650-61 (2002).

Hayashi, E. A., et al., (2005). Role of TLR in B cell development: signaling through TLR4 promotes B cell maturation and is inhibited by TLR2. J Immunol 174, 6639-6647.

Hochedlinger, K., and Jaenisch, R. (2002). Monoclonal mice generated by nuclear transfer from mature B and T donor cells. Nature 415, 1035-1038.

Hochedlinger, K., and Jaenisch, R., Nature 441 (7097), 1061 (2006).

Hochedlinger, K., et al., Cell 121 (3), 465 (2005).

Hochedlinger, K. & Jaenisch, R. Nuclear reprogramming and pluripotency. Nature 441, 1061-1067 (2006).

Hogan et al., Cold Spring Contain Laboratory Press, Cold Spring Contain, New York, 2003.

Holm, T. M., et al., Cancer Cell 8 (4), 275 (2005).

Ihle, J. H., Cell 84: 331-334 (1996).

Inoue, K., et al., (2005). Generation of cloned mice by direct nuclear transfer from natural killer T cells. Curr Biol 15, 1114-1118.

Jaenisch, R., Young (2008). Stem Cells, the Molecular Circuitry of Pluripotency and Nuclear Reprogramming. Cell 132.

Jaenisch, R., N Engl J Med 351 (27), 2787 (2004).

Jackson-Grusby, L., et al., Nat. Genet. 27 (1), 31 (2001).

Jung, D., et al., (2006). Mechanism and control of V(D)J recombination at the immunoglobulin heavy chain locus. Annual review of immunology 24, 541-570.

Labosky, P. A., et al., Development 120 (11), 3197 (1994).

Laiosa, C. V., et al., (2006). Reprogramming of committed T cell progenitors to macrophages and dendritic cells by C/EBP alpha and PU.1 transcription factors. Immunity 25, 731-744.

Lee, T. I., et al., Cell 125 (2), 301 (2006).

Lengner, C. et al. Oct4 is dispensable for somatic stem cell self-renewal. Cell Stem Cells submitted (2007).

Lewis, S., at al., (1982). Continuing kappa-gene rearrangement in a cell line transformed by Abelson murine leukemia virus. Cell 30, 807-816.

Li, E., at al., Cell 69, 915 (1992).

Li, J., et al., (2007). Mice cloned from skin cells. Proceedings of the National Academy of Sciences of the United States of America 104, 2738-2743.

Li, J., et al., (2004). Odorant receptor gene choice is reset by nuclear transfer from mouse olfactory sensory neurons. Nature 428, 393-399.

Loh, Y. H., et al., (2006). The Oct4 and Nanog transcription network regulates pluripotency in mouse embryonic stem cells. Nature genetics 38, 431-440.

Lucifero, D., et al., Genomics 79 (4), 530 (2002).

Maherali, N. et al. (2007). Directly Reprogrammed Fibroblasts Show Global Epigenetic Remodeling and Widespread Tissue Contribution. Cell Stem Cells 1, 55-70.

(2) Maherali, N. et al. Global epigenetic remodeling in directly reprogrammed fibroblasts. Cell Stem Cells in press (2007).

Matthews, V. B., et al., (2004). Genetic manipulations utilizing albumin and alpha-fetoprotein promoter/enhancers affect both hepatocytes and oval cells. Hepatology 40, 759-760.

Matthias, P., and Rolink, A. G. (2005). Transcriptional networks in developing and mature B cells. Nature reviews 5, 497-508.

Meissner, A., et al., (2007). Direct reprogramming of genetically unmodified fibroblasts into pluripotent stem cells. Nature biotechnology 25, 1177-1181.

Meissner, A. et al., Nucleic Acids Res 33 (18), 5868 (2005).

Milne, C. D., et al., (2004). IL-7 does not prevent pro-B/pre-B cell maturation to the immature/sIgM(+) stage. European journal of immunology 34, 2647-2655.

Mitsui, K., et al., Cell 113 (5), 631 (2003).

Munsie M. J., et al., Curr. Biol. 10: 989 (2000).

Nadel, B., et al., (1990). Murine lambda gene rearrangements: the stochastic model prevails over the ordered model. The EMBO journal 9, 435-440.

Nakagawa, M., et al., (2008). Generation of induced pluripotent stem cells without Myc from mouse and human fibroblasts. Nature biotechnology 26, 101-106.

Naviaux, R. K., et al., The pCL vector system: rapid production of helper-free, high-titer, recombinant retroviruses. J Virol 70, 5701-5705 (1996).

Oberdoerffer, P., et al., (2003). Expression of a targeted lambda 1 light chain gene is developmentally regulated and independent of Ig kappa rearrangements. The Journal of experimental medicine 197, 1165-1172.

Okano, M., et al., Cell 99, 247 (1999).

Okita, K., et al., (2007). Generation of germline-competent induced pluripotent stem cells. Nature 448, 313-317.

Papavasiliou, F., et al., (1997). V(D)J recombination in mature B cells: a mechanism for altering antibody responses. Science 278, 298-301.

Park, I. H., et al., (2008). Reprogramming of human somatic cells to pluripotency with defined factors. Nature 451, 141-146.

Peitz, M., et al., Proc Natl Acad Sci USA 99 (7), 4489 (2002).

Postic, C., et al., (1999). Dual roles for glucokinase in glucose homeostasis as determined by liver and pancreatic beta cell-specific gene knock-outs using Cre recombinase. The Journal of biological chemistry 274, 305-315.

Ramji, D. P., and Foka, P. (2002). CCAAT/enhancer-binding proteins: structure, function and regulation. The Biochemical journal 365, 561-575.

Rountree, C. B., et al., (2007). A CD133-expressing murine liver oval cell population with bilineage potential. Stem cells (Dayton, Ohio) 25, 2419-2429.

Schlissel, M. S. (2003). Regulating antigen-receptor gene assembly. Nature reviews 3, 890-899.

Schlissel, M. S., et al., (1991). Virus-transformed pre-B cells show ordered activation but not inactivation of immunoglobulin gene rearrangement and transcription. The Journal of experimental medicine 173, 711-720.

Shmblott, M. J., at al., Derivation of pluripotent stem cells from cultured human primordial germ cells. Proc. Natl. Acad. Sci. USA 95: 13726-13731 (1998).

Smith A. G., et al. Nature 336: 688-690 (1988).

Stadtfeld, M., et al., (2008). Defining Molecular Cornerstones during Fibroblast to iPS Cell Reprogramming in Mouse. Cell Stem Cell Advance Online Publication.

Tada, M., et al., (2001). Nuclear reprogramming of somatic cells by in vitro hybridization with ES cells. Curr Biol 11, 1553-1558.

Takahashi, K., et al., (2007). Induction of pluripotent stem cells from adult human fibroblasts by defined factors. Cell 131, 861-872.

Takahashi, K., and Yamanaka, S. (2006). Induction of pluripotent stem cells from mouse embryonic and adult fibroblast cultures by defined factors. Cell 126, 663-676.

Tan, D. S., et al., S. L. J. Am. Chem. Soc. 120, 8565-8566 (1998).

Teng, G., and Papavasiliou, F. N. (2007). Immunoglobulin somatic hypermutation. Annual review of genetics 41, 107-120.)

Thomson, J. A., at al., Embryonic stem cell lines derived from human blastocysts. Science, 282: 1145-1147 (1998).

Urlinger S., et al., Proc. Natl. Acad. Sci. USA. 97(14): 7963-8 (2000). Exploring the sequence space for tetracycline-dependent transcriptional activators: novel mutations yield expanded range and sensitivity.

Ventura, A., et al., Proc Natl Acad Sci USA 101 (28), 10380 (2004).

Wakayama, T., and Yanagimachi, R. (2001). Mouse cloning with nucleus donor cells of different age and type. Molecular reproduction and development 58, 376-383.

Walsh, C. P., et al., Nat. Genet. 20 (2), p 116 (1998).

Wang, X., et al., (2003). The origin and liver repopulating capacity of murine oval cells. Proceedings of the National Academy of Sciences of the United States of America 100 Suppl 1, 11881-11888.

Wang, Z. & Jaenisch, R. At most three ES cells contribute to the somatic lineages of chimeric mice and of mice produced by ES-tetraploid complementation. Dev Biol 275, 192-201 (2004).

Wernig, M., et al., (2007). In vitro reprogramming of fibroblasts into a pluripotent ES-cell-like state. Nature 448, 318-324.

Wernig, M. A., et al., (2008). c-Myc Is Dispensable for Direct Reprogramming of Mouse Fibroblasts. Cell Stem Cell 2, 10-12.

Wernig, M., at al., J Neurosci 24 (22), 5258 (2004).

William R. L., et al., Nature 336: 684-687 (1988)

Wilmut, I., et al., (1997). Viable offspring derived from fetal and adult mammalian cells. Nature 385, 810-813.

Xie, H., at al., (2004). Stepwise reprogramming of B cells into macrophages. Cell 117, 663-676.

Yamada, Y., et al., (1990). Regulation of the collagen II gene in vitro and in transgenic mice. Ann. New York Acad. Sci. 580, 81-87.

Yamanaka, S. Strategies and New Developments in the Generation of Patient-Specific Pluripotent Stem Cells. Cell Stem Cells 1, 39-49 (2007).

Yang, X. et al. Nuclear reprogramming of cloned embryos and its implications for therapeutic cloning. Nat Genet 39, 295-302 (2007).

Yu, J., et al. (2007), Induced pluripotent stem cell lines derived from human somatic cells. Science (New York, N.Y. 318, 1917-1920.

Zambrowicz B. P. et al., Disruption of overlapping transcripts in the ROSA bgeo 26 gene trap strain leads to widespread expression of b-galatosidase in mouse embryos and hematopoietic cells. Proc. Natl. Acad. Sci. USA 94: 3789-3794 (1997).

Zhu, D., et al., (2005). Deregulated expression of the Myc cellular oncogene drives development of mouse "Burkitt-like" lymphomas from naive B cells. Blood 105, 2135-2137.

What is claimed is:

1. A method of reprogramming a cell to a pluripotent state comprising: (a) introducing into the cell exogenous factors comprising (i) polynucleotides encoding Oct-4, Sox-2, and Klf-4, but not c-Myc; or (ii) Oct-4, Sox-2, and Klf-4 polypeptides, but not a c-Myc polypeptide, and (b) culturing the cell for a sufficient amount of time to reprogram the cell to the pluripotent state, wherein the reprogrammed cell does not express a selectable marker operably linked to a pluripotency gene.

2. The method of claim 1, wherein the polynucleotides are introduced by transfection or viral infection.

3. The method of claim 1, wherein step (a) comprises introducing said polynucleotides into the cell; and the method further comprising inactivating at least one of the polynucleotides after the cell obtains the pluripotent state, wherein said inactivating optionally comprises excising at least a portion of a coding sequence from the at least one of the polynucleotides, wherein the portion of the coding sequence is flanked by sequences that are recognized by a site-specific recombinase, and wherein said excising comprises introducing or expressing the site-specific recombinase in the cell after the cell obtains the pluripotent state, wherein the site-specific recombinase removes the portion of the coding sequence from the at least one of the polynucleotides.

4. A method of reprogramming a human adult somatic cell to a pluripotent state comprising the steps of: (a) introducing into a human adult somatic cell reprogramming agents that contribute to reprogramming of the cell, wherein the reprogramming agents comprise Oct-4, Sox-2, and Klf-4, but not c-Myc; and (b) culturing the cell in a medium comprising cell proliferation factors and factors that support reprogramming for a period of time sufficient to reprogram the cell to the pluripotent state, wherein the cell does not comprise a selectable marker operably linked to an endogenous pluripotency gene.

5. The method of claim 4, wherein the reprogramming agents are introduced as (i) polynucleotides encoding Oct-4, Sox-2, and Klf-4, but not c-Myc; or (ii) Oct-4, Sox-2, and Klf-4 polypeptides, but not a c-Myc polypeptide.

6. The method of claim 4, wherein the somatic cell is a partially differentiated cell or a fully differentiated cell.

7. A method of generating a reprogrammed human pluripotent cell comprising: introducing into a human somatic cell, exogenous polynucleotides encoding Oct-4, Sox-2, and Klf-4, but not c-Myc; or exogenous Oct-4, Sox-2, and Klf-4 polypeptides, but not a c-Myc polypeptide, culturing said human somatic cell for a sufficient amount of time to obtain a reprogrammed human pluripotent that (i) is resistant to DNA demethylation; (ii) expresses endogenous Oct-4; (iii) differentiates into tissues having the characteristics of endoderm, mesoderm, and ectoderm when injected into SCID mice; and (iv) does not comprise a selectable marker operably linked to an endogenous pluripotency gene.

8. The method of claim 7, wherein the exogenously introduced polynucleotides are introduced into the human somatic cell by transfection or viral infection.

9. The method of claim 7, wherein step (a) comprises introducing said polynucleotides into the human somatic cell; and the method further comprising inactivating at least one of the polynucleotides after the human somatic cell becomes the reprogrammed human pluripotent cell, wherein said inactivating optionally comprises excising at least a portion of a coding sequence from the at least one of the polynucleotides, wherein the portion of the coding sequence is flanked by sequences that are recognized by a site-specific recombinase, and wherein said excising comprises introducing or expressing the site-specific recombinase in the cell after the human somatic cell becomes the reprogrammed human pluripotent cell, wherein the site-specific recombinase removes the portion of the coding sequence from the at least one of the polynucleotides.

\* \* \* \* \*